US008206753B2

(12) United States Patent
Tripp et al.

(10) Patent No.: US 8,206,753 B2
(45) Date of Patent: *Jun. 26, 2012

(54) ANTI-INFLAMMATORY BOTANICAL PRODUCTS FOR THE TREATMENT OF METABOLIC SYNDROME AND DIABETES

(75) Inventors: Matthew L. Tripp, Gig Harbor, WA (US); John G. Babish, Brooktondale, NY (US); Jeffrey S. Bland, Fox Island, WA (US); Amy J. Hall, Gig Harbor, WA (US); Veera Konda, Gig Harbor, WA (US); Linda M. Pacioretty, Brooktondale, NY (US)

(73) Assignee: Metaproteomics, LLC, San Clemente, CA (US)

( * ) Notice: Subject to any disclaimer, the term of this patent is extended or adjusted under 35 U.S.C. 154(b) by 296 days.

This patent is subject to a terminal disclaimer.

(21) Appl. No.: 11/635,305

(22) Filed: Dec. 7, 2006

(65) Prior Publication Data
US 2007/0281045 A1     Dec. 6, 2007

Related U.S. Application Data

(63) Continuation-in-part of application No. 10/689,856, filed on Oct. 20, 2003, now Pat. No. 7,270,835, which is a continuation-in-part of application No. 10/464,410, filed on Jun. 18, 2003, now Pat. No. 8,142,819, which is a continuation-in-part of application No. 10/400,293, filed on Mar. 26, 2003, now abandoned, and a continuation-in-part of application No. 10/401,283, filed on Mar. 26, 2003, now abandoned, and a continuation-in-part of application No. 10/464,834, filed on Jun. 18, 2003, now abandoned, which is a continuation-in-part of application No. 09/885,721, filed on Jun. 20, 2001, now Pat. No. 7,205,151.

(60) Provisional application No. 60/748,907, filed on Dec. 9, 2005, provisional application No. 60/450,237, filed on Feb. 25, 2003, provisional application No. 60/420,383, filed on Oct. 21, 2002.

(51) Int. Cl.
*A01N 65/00*     (2009.01)
(52) U.S. Cl. .................................................... 424/725
(58) Field of Classification Search ....................... None
See application file for complete search history.

(56) References Cited

U.S. PATENT DOCUMENTS 3,451,821 A    6/1969   Todd et al.
(Continued)

FOREIGN PATENT DOCUMENTS
CN      1203268      12/1998
(Continued)

OTHER PUBLICATIONS

International Search Report for related PCT Application No. PCT/US2006/046770, dated Mar. 26, 2008, 8 pages.
(Continued)

*Primary Examiner* — Michael Meller
(74) *Attorney, Agent, or Firm* — McDermott Will & Emery, LLP

(57) ABSTRACT

Disclosed are botanically based compositions and methods useful for the treatment of metabolic syndrome and diabetes type 2. Compositions, kits, and methods are additionally disclosed for means to augment the activity of identified glucose and insulin regulating drugs.

4 Claims, 28 Drawing Sheets

U.S. PATENT DOCUMENTS

| | | |
|---|---|---|
| 3,536,495 A | 10/1970 | Westermann et al. |
| 3,552,975 A | 1/1971 | Worden |
| 3,720,517 A | 3/1973 | Bavisotto et al. |
| 3,932,603 A | 1/1976 | Haas |
| 3,933,919 A | 1/1976 | Wilkinson |
| 3,965,188 A | 6/1976 | Westermann et al. |
| 4,123,561 A | 10/1978 | Grant |
| 4,133,903 A | 1/1979 | Thiele et al. |
| 4,148,873 A | 4/1979 | Owades |
| 4,154,865 A | 5/1979 | Grant |
| 4,170,638 A | 10/1979 | Owades |
| 4,389,421 A | 6/1983 | Palamand |
| 4,401,684 A | 8/1983 | Versluys |
| 4,473,551 A | 9/1984 | Schinitsky |
| 4,554,170 A | 11/1985 | Panzer et al. |
| 4,590,296 A | 5/1986 | Cowles et al. |
| 4,644,084 A | 2/1987 | Cowles et al. |
| 4,692,280 A | 9/1987 | Spinelli |
| 4,758,445 A | 7/1988 | Klusters |
| 4,767,640 A | 8/1988 | Goldstein et al. |
| 4,857,554 A | 8/1989 | Kallimanis |
| 5,006,337 A | 4/1991 | Motitschke et al. |
| 5,013,571 A | 5/1991 | Hay |
| 5,041,300 A | 8/1991 | Todd et al. |
| 5,073,396 A | 12/1991 | Todd, Jr. |
| 5,082,975 A | 1/1992 | Todd, Jr. et al. |
| 5,155,276 A | 10/1992 | Paul |
| 5,166,449 A | 11/1992 | Todd, Jr. et al. |
| 5,264,236 A | 11/1993 | Ogasahara et al. |
| 5,286,506 A | 2/1994 | Millis et al. |
| 5,370,863 A * | 12/1994 | Barney et al. .................... 424/49 |
| 5,387,425 A | 2/1995 | Hsu et al. |
| 5,604,263 A | 2/1997 | Tobe et al. |
| 5,641,517 A | 6/1997 | Eskeland et al. |
| 5,827,895 A | 10/1998 | Nutter et al. |
| 5,866,162 A | 2/1999 | Grattan |
| 5,919,813 A | 7/1999 | De Juan |
| 5,968,539 A | 10/1999 | Beerse et al. |
| 6,020,019 A | 2/2000 | Ting et al. |
| 6,129,907 A | 10/2000 | Sreenivasan et al. |
| 6,200,594 B1 | 3/2001 | Ernest et al. |
| 6,210,701 B1 | 4/2001 | Darland et al. |
| 6,224,871 B1 | 5/2001 | Hastings et al. |
| 6,264,995 B1 | 7/2001 | Newmark et al. |
| 6,291,483 B1 | 9/2001 | Upadhyay et al. |
| 6,303,146 B1 * | 10/2001 | Bonhomme et al. .......... 424/465 |
| 6,383,527 B1 | 5/2002 | Artman et al. |
| 6,391,346 B1 | 5/2002 | Newmark et al. |
| 6,440,465 B1 | 8/2002 | Meisner |
| 6,447,762 B1 | 9/2002 | Galcerá |
| 6,482,456 B1 | 11/2002 | Yokoo et al. |
| 6,492,429 B1 | 12/2002 | Graus et al. |
| 6,583,322 B1 | 6/2003 | Shalai et al. |
| 6,689,388 B2 | 2/2004 | Kuhrts |
| 6,790,459 B1 | 9/2004 | Cheng et al. |
| 6,801,860 B1 | 10/2004 | Dessen et al. |
| 7,078,062 B2 | 7/2006 | Hass |
| 7,144,590 B2 | 12/2006 | Khurts |
| 7,195,785 B2 | 3/2007 | Babish et al. |
| 7,205,151 B2 | 4/2007 | Babish et al. |
| 7,270,835 B2 | 9/2007 | Tripp et al. |
| 7,279,185 B2 | 10/2007 | Babish et al. |
| 7,332,185 B2 | 2/2008 | Babish et al. |
| 7,431,948 B2 | 10/2008 | Tripp et al. |
| 2002/0028852 A1 | 3/2002 | Ghai et al. |
| 2002/0076452 A1 | 6/2002 | Babish et al. |
| 2002/0077299 A1 | 6/2002 | Babish et al. |
| 2002/0086062 A1 | 7/2002 | Kuhrts |
| 2002/0086070 A1 | 7/2002 | Kuhrts |
| 2002/0156087 A1 | 10/2002 | Nuss et al. |
| 2003/0003212 A1 | 1/2003 | Chien et al. |
| 2003/0008021 A1 | 1/2003 | Babish et al. |
| 2003/0035851 A1 | 2/2003 | Chen |
| 2003/0077313 A1 | 4/2003 | Schwartz et al. |
| 2003/0096027 A1 | 5/2003 | Babish et al. |
| 2003/0113393 A1 | 6/2003 | Babish et al. |
| 2003/0133958 A1 | 7/2003 | Kuno et al. |
| 2003/0180402 A1 | 9/2003 | Jia et al. |
| 2003/0228369 A1 | 12/2003 | Kuhrts |
| 2004/0072900 A1 | 4/2004 | Artman et al. |
| 2004/0086580 A1 | 5/2004 | Tripp et al. |
| 2004/0115290 A1 | 6/2004 | Tripp et al. |
| 2004/0137096 A1 | 7/2004 | Kuhrts |
| 2004/0151792 A1 | 8/2004 | Tripp et al. |
| 2004/0186062 A1 | 9/2004 | Burnett et al. |
| 2004/0219240 A1 | 11/2004 | Babish et al. |
| 2005/0042317 A1 | 2/2005 | Babish et al. |
| 2005/0129791 A1 | 6/2005 | Babish et al. |
| 2005/0191375 A1 | 9/2005 | Babish et al. |
| 2005/0192356 A1 | 9/2005 | Babish et al. |
| 2006/0074052 A1 | 4/2006 | Eliaz |
| 2006/0127511 A1 | 6/2006 | Tripp et al. |
| 2006/0127512 A1 | 6/2006 | Tripp et al. |
| 2006/0127513 A1 | 6/2006 | Tripp et al. |
| 2006/0127514 A1 | 6/2006 | Tripp et al. |
| 2006/0127515 A1 | 6/2006 | Tripp et al. |
| 2006/0127516 A1 | 6/2006 | Tripp et al. |
| 2006/0127517 A1 | 6/2006 | Tripp et al. |
| 2006/0193933 A1 | 8/2006 | Tripp et al. |
| 2006/0233902 A1 * | 10/2006 | Yajima et al. ................. 424/778 |
| 2007/0003646 A1 | 1/2007 | Kuhrts |
| 2007/0020352 A1 | 1/2007 | Tripp et al. |
| 2007/0065456 A1 | 3/2007 | Woods |
| 2007/0154576 A1 | 7/2007 | Tripp et al. |
| 2007/0160692 A1 | 7/2007 | Tripp et al. |
| 2007/0166418 A1 | 7/2007 | Tripp et al. |
| 2007/0172532 A1 | 7/2007 | Babish et al. |
| 2007/0184133 A1 | 8/2007 | Tripp et al. |
| 2008/0127720 A1 | 6/2008 | Pauli et al. |
| 2008/0248131 A1 | 10/2008 | Tripp et al. |
| 2009/0118373 A1 | 5/2009 | Tripp et al. |

FOREIGN PATENT DOCUMENTS

| | | |
|---|---|---|
| DE | 1901277 | 8/1970 |
| DE | 2212148 | 9/1972 |
| DE | 3931147 | 3/1991 |
| DE | 19841615 | 3/2000 |
| EP | 0229022 | 7/1987 |
| EP | 0606599 A1 | 7/1994 |
| EP | 0681029 A2 | 11/1995 |
| EP | 1481671 | 12/2004 |
| EP | 1543834 | 6/2005 |
| EP | 1 938 828 | 7/2008 |
| GB | 2330076 | 4/1999 |
| JP | 52145509 | 12/1977 |
| JP | 58009084 | 2/1983 |
| JP | 59059623 | 4/1984 |
| JP | 363211219 | 9/1988 |
| JP | 04202138 | 7/1992 |
| JP | 6312924 | 11/1994 |
| JP | 07165583 | 6/1995 |
| JP | 07194351 | 8/1995 |
| JP | 8073369 | 3/1996 |
| JP | 08073369 | 3/1996 |
| JP | 9067245 | 3/1997 |
| JP | 09502202 | 3/1997 |
| JP | 410025247 | 1/1998 |
| JP | 10152428 | 6/1998 |
| JP | 10179129 | 7/1998 |
| JP | 11246399 | 9/1999 |
| JP | 11513037 | 11/1999 |
| JP | 11335231 | 12/1999 |
| JP | 2000-080044 | 3/2000 |
| JP | 2001161338 | 6/2001 |
| JP | 2002-12550 | 1/2002 |
| JP | 2002-505296 | 2/2002 |
| RU | 2045955 | 10/1995 |
| SU | 1247011 | 7/1986 |
| WO | WO 9507079 | 3/1995 |
| WO | WO 97/31630 | 9/1997 |
| WO | WO 9749405 | 12/1997 |
| WO | WO 99/44623 | 9/1999 |
| WO | WO 99/61038 | 12/1999 |
| WO | WO 00/68356 | 11/2000 |
| WO | WO 00/74696 | 12/2000 |
| WO | WO 02/02582 | 1/2002 |
| WO | WO 02/32234 | 4/2002 |

| | | |
|---|---|---|
| WO | WO 03/000185 | 1/2003 |
| WO | WO 03/035007 | 5/2003 |
| WO | 03/057232 A1 | 7/2003 |
| WO | WO 03/068205 | 8/2003 |
| WO | WO 03068205 * | 8/2003 |
| WO | WO 03/075943 | 9/2003 |
| WO | WO 03/082249 | 10/2003 |
| WO | WO 2004/037180 | 5/2004 |
| WO | 2004/045632 A1 | 6/2004 |
| WO | WO 2004/062611 | 7/2004 |
| WO | WO 2005/039483 | 5/2005 |
| WO | WO 2005/084230 | 9/2005 |
| WO | WO 2006/053249 | 5/2006 |
| WO | WO 2006/062681 | 6/2006 |
| WO | WO 2007/021694 | 2/2007 |
| WO | WO 2007/067812 | 6/2007 |
| ZA | 200000857 | 8/2001 |

OTHER PUBLICATIONS

Written Opinion for related PCT Application No. PCT/US2006/046770, dated Mar. 26, 2008, 7 pages.
Fukuchi, Y., et al. "6-methylsulfinylhexyl isothiocyanate, an antioxidant derived from *Wasabia japonica* MATUM, ameliorates diabetic nephropathy in type 2 diabetic mice." Food Science and Tech. Research, 2004, vol. 10, No. 3, pp. 290-295 (abstract).
Shukla, et al., "In vitro and in vivo would healing activity of asiaticoside isolated from *Centella asiatica*." Journal of Ethnopharmacology. Apr. 1999, vol. 65, No. 1, pp. 1-11.
Incandela, L. et al., "Treatment of Diabetic Microangiopathy and Edema with Total Triterpenic Fraction of *Centella asiatica*: A Prospective, Placebo-Controlled Randomized Study." Angiology. Oct. 2001, vol. 52, suppl. 2, pp. S27-S31.
Parry, J., et al., "Fatty Acid Composition and Antioxidant Properties of Cold-Pressed Marionberry, Boysenberry, Red Raspberry, and Blueberry Seed Oils." Journal of Agriculture and Food Chemistry, Feb. 9, 2005, vol. 53, No. 3, pp. 566-573.
Mallavarapu, G.R., et al,, "Influence of Plant Growth Stage on the Essential Oil Content and Composition in Davana (Artemisia pallens wall.)," Journal of Agricultural and Food Chemistry, Jan. 1999, vol. 47, No. 1, pp. 254-258.
Dorababu, M., et al., "Effect of *Bacopa monniera* and *Azadirachta indica* on gastric ulceration and healing in experimental NIDDM rats." Indian Journal of Experimental Biology, Apr. 2004, vol. 42, No. 4, pp. 389-397 (abstract).
Yajima, H., et al., "Isohumulones, Bitter Acids Derived from Hops, Activate Both Peroxisome Proliferator-activated Receptor α and γ and Reduce Insulin Resistance." The Journal of Biological Chemistry. Aug. 2004, vol. 279, No. 32, pp. 33456-33462.
Yajima, H., et al,, "Prevention of diet-induced obesity by dietary isomerized hop extract containing isohumulones, in rodents." Intl. Journal of Obesity, Aug. 2005, vol, 29, No. 8, pp. 991-997.
Turner, R.C., et al., Glycemic Control With Diet, Sulfonylurea, Metformin, or Insulin in Patients With Type 2 Diabetes Mellitus: Progressive Requirement for Multiple Therapies (UKPDS) Group JAMA Jun. 2, 1999, vol. 281, No. 21, pp. 2005-2012.
Abel-salam et al., Pharmacological Research, England 47(4), pp. 311-340 (Apr. 2003).
Albal, MV., et al., "Clinical evaluation of berberine in mycotic infections." Indian J. Ophthalmol 34:91-2 (1986).
Anto, et al., "Anti-inflammatory Activity of Natural and Synthetic Curcuminoids", Pharmacy and Pharmacology Communications, 4(2), pp. 103-106 (1998).
Baldermann et al., J. Chromatography A 1192(1):191-3 (May 23, 2008) (Epub Apr. 8, 2008); abstract only (1 page).
Bermejo, et al. Rev. Esp. Enferm. Dig. 95(9): 621-624 and 625-628 (2003).
Bolick D et al., Endocrinology 144(12), pp. 5227-5231 (Dec. 2003).
Brown, et al. J. Chem. Soc. 545 (1959).
Buhler et al., Antioxidant Activities of Flavanoids, 3 pages, Nov. 2000.
Byrne, et al. J. Chem. Soc. (C):2810 (1971).
Carroccio, et al. Clin. Chem. 49(6):861-867 (2003).
Carson, J. Am. Chem. Soc. 73:1850-1851 (1951).

Chandra, et al. Indian J. Medical Research 60(1):138-142 (1972).
Charlier, et al. Eur. J. Med. Chem. 38:645-659 (2003).
Chattopadhyay et al., Current Science, 87(1) (Jul. 10, 2004).
Chen Wei-Jen et al., Journal of Agricultural and Food Chemistry 52(1), pp. 55-64 (Jan. 1, 2004).
Chou et al. Eur. J. Biochem. 115:207-216 (1981).
Chou, et al. Adv enzyme regul 22:27-55 (1983).
Chou, et al. Eur. J. Biochem. 115:207-216 (1981).
Chou, et al. J. Biol. Chem. 252(18):6438-6442 (1977).
Chou, et al. J. Theor. Biol. 35:285-297 (1972).
Chou, J. Theor. Biol. 59:253-276 (1976).
Chou, et al., TIPS, pp. 450-454, Nov. 1983.
Cohen, Protein Kinases—the major drug targets of the twenty-first century? Nature Reviews, 1: 309-315 (2002).
Costa, et al. Digest. Liver Dis. 35:642-647 (2003).
Davies, WL. Abstract—Fertiliser, Feeding Stuffs and Farm Supplies J. 11:694 (1926).
De Keukeleire "Fundamentals of Beer and Hop Chemistry" Quimica Nova, 23(1) pp. 108-112 (2000).
Ding, et al. Biochem. Biophy. Res. Comm. 261:218-223 (1999).
European Examination Report for EP App. No. 02748188.6-1216.
European Search Report for EP App. No. 07809709.4.
European Search Report EP 05 723 839.6.
European Search Report EP 10006768.
European Search Report EP 10011254.
European Search Report EP 10013109.
European Search Report EP 10162893.
European Search Report for corresponding EP Application No. 02737562.5 (4 pages).
European Search Report for related European Application No. 02784313.5.
Exercise as Treatment for Arthritis, Rheumatic and Immunologic Diseases, Cleveland Clinic, www.clevelandclinic.org, Mar. 14, 2000.
Extended European Search Report EP 10162893.1.
Extended European Search Report EP 07717798.8.
Extended European Search Report EP 07809708.6.
Foucault et al., J. Chromatography A 808(1-2):3-22 (May 29, 1998); abstract only (3 pages).
Friedman, et al. J. Cutan Med. Surg. 6(5):449-459 (2002).
Gao et al., J. Food Sci. Nutr. vol. 9, pp. 240-244 (2004).
Gerhauser et al., Molecular Cancer Therapeutics vol. 1, No. 11, pp. 959-969 (2002).
Gerhauser, Beer Constituents as Potential Cancer Chemopreventive Agents, EP Journal of Cancer 41; 1941-1954: (2005).
Germany, "The Absolutely German Drink," contents of beer, 2004, 5 pages.
Gilani, "Studies on Antihypertensive and Antispasmodic Activities of Methanol Extract of *Acacia nilotica* Pods", Phytotherapy Research 13: 665-669 (1999).
Goldstein, et al. Am. J. Gastroenterol. 96(4):1019-1027 (2001).
Halter, et al. Gut 49:443-453 (2001).
Hamberg, et al. J. Bio. Chem. 246(22):6713-6721 (1971).
Hariddradilepah 01, TKDL, Aug. 1, 1999, XP003024376, (3 pages).
Huang, et al. Cancer Res. 51:813-819 (1991).
Information on ArthroTrimTM product, downloaded from Internet Aug. 30, 2002.
Information on "Hops and Beer Flavours", IOB Technical Symposium, Apr. 2001, pp. 1-9.
Informatin on "Zyflamend and Zyflamend PM", downloaded from Internet Aug. 30, 2002.
International Search Report for Corresponding PCT Application No. PCT/US05/41018; 2pp.
International Search Report for PCT /US06/30920, Aug. 3, 2007, 3 pages.
International Search Report for PCT/US02/19617.
International Search Report for PCT/US04/16043.
International Search Report for PCT/US06/47196.
Jach, Przegl Dermatol. 65(4):379-381 (1978).
Jafri et al., Pakistan Journal of Science, vol. 61, No. 4, pp. 220-222 (Dec. 2009).
Kaltner, Investigation of formation of Hops Aroma and technological Measures for Products of Hops-Aromatic Beers, Technical University of Munich, 7 pp. corresponding to Kaltner, D., Technische Universitat Munchen, (Nov. 30, 2000), pp. 1-193, plus Tabs. AH1-AH31.
Kanematsu, et al. J Bone Miner Res 12(11):1789-1796 (1997).
Konda, et al., Arthritis & Rheumatism 62(6): 1683-1692, (2010).
Kuo et al., Cancer Letter, 203:127-137 (2004).
Lamy Virginie et al., Apoptosis, an Int'l Journal on Programmed Cell Death, 13(10), pp. 1232-1242 (Aug. 25, 2008).
Lamy Virginie et al., Carcinogenesis, 28(7), pp. 1575-1581 (Jul. 2007).
Lerman et al, FASEB Journal , Fed. of American Soc. for Experimental Biol., vol. 18, No. 4-5 (Jan. 1, 2004).
Lopes, Curr. Med Res Opin. 8(3):145-149 (1982).
Lukaczer et al., Phytotherapy Research, vol. 19, No. 10, pp. 864-869 (2005).
Mannering et al., Food, Nutrition and Chemical Toxicity X(X), pp. 311-323 (Jan. 1, 1993).
Meling, et al. Scand. J. Gastroenterol. 31:339-344 (1996).
Minich et al., Journal of nutrition and Metabolism, vol. 2010, article ID 467316, pp. 1-11, (2010).
Murvadyaghrtam, TKDL, Jan. 1, 2001, XP003024377 (4 pages).
Murvadyaghrtam, TKDL, Jan. 1, 1990, XP003024379 (4 pages).
Newark, et al., "Beyond Aspirin", pp. 147-151, Hohm Press (2000).
Noreen, et al. J. Nat. Prod 61:2-7 (1998).
Office Action issued for U.S. Appl. No. 11/667,614 mailed Apr. 16, 2010.
Office Action issued for U.S. Appl. No. 11/667,615 mailed Mar. 16, 2010.
Office Action issued for U.S. Appl. No. 11/701,583 mailed Feb. 8, 2008.
Office Action issued for U.S. Appl. No. 11/701,583 mailed Jul. 6, 2009.
Office Action issued for U.S. Appl. No. 11/701,583 mailed Nov. 26, 2008.
Office Action issued in U.S. Appl. No. 10/464,834 on Aug. 3, 2010.
Office Action issued in U.S. Appl. No. 10/532,388 on Mar. 26, 2010.
Office Action issued in U.S. Appl. No. 10/532,388 on Jun. 28, 2011.
Office Action issued in U.S. Appl. No. 10/590,301 on Aug. 19, 2010.
Office Action issued in U.S. Appl. No. 10/590,424 on Jun. 29, 2010.
Office Action issued in U.S. Appl. No. 10/789,814 on Jun. 11, 2010.
Office Action issued in U.S. Appl. No. 10/789,814 on Mar. 18, 2011.
Office Action issued in U.S. Appl. No. 11/344,555 on Jan. 19, 2011.
Office Action issued in U.S. Appl. No. 11/344,556 on Sep. 3, 2010.
Office Action issued in U.S. Appl. No. 11/344,556 on Dec. 16, 2009.
Office Action issued in U.S. Appl. No. 11/344,556 on Mar. 27, 2009.
Office Action issued in U.S. Appl. No. 11/344,557 on Mar. 25, 2010.
Office Action issued in U.S. Appl. No. 11/344,557 on Apr. 21, 2008.
Office Action issued in U.S. Appl. No. 11/344,557 on Aug. 28, 2009.
Office Action issued in U.S. Appl. No. 11/344,557 on Jan. 10, 2007.
Office Action issued in U.S. Appl. No. 11/344,557 on Sep. 26, 2007.
Office Action issued in U.S. Appl. No. 11/636,867 on Aug. 30, 2010.
Office Action issued in U.S. Appl. No. 11/636,867 on Mar. 8, 2011.
Office Action issued in U.S. Appl. No. 11/649,584 on Mar. 3, 2010.
Office Action issued in U.S. Appl. No. 11/344,552 on Sep. 8, 2010.
Office Action issued in U.S. Appl. No. 11/501,393 on Aug. 25, 2010.
Office Action issued in U.S. Appl. No. 11/729,696 on Nov. 1, 2010.
Office Action issued in U.S. Appl. No. 11/820,600 on Sep. 30, 2010.
Office Action issued in U.S. Appl. No. 11/820,607 on Oct. 12, 2010.
Office Action issued in U.S. Appl. No. 12/030,335 on Oct. 21, 2010.
Office Action issued in U.S. Appl. No. 12/048,613 on Dec. 8, 2010.
Office Action issued in U.S. Appl. No. 12/754,820 on Mar. 15, 2011.
Office Action issued in U.S. Appl. No. 12/626,392 on Oct. 27, 2010.
Office Action issued in U.S. Appl. No. 11/729,696 on Mar. 25, 2010.
Office Action issued in U.S. Appl. No. 11/729,696 on Jul. 14, 2011.
Office Action issued in U.S. Appl. No. 11/820,755 on Oct. 18, 2010.
Office Action issued in U.S. Appl. No. 11/820,755 on Jun. 1, 2011.
Office Action issued in U.S. Appl. No. 10/464,410 on May 23, 2011.
Office Action issued in U.S. Appl. No. 11/820,607 on May 23, 2011.
Office Action issued in U.S. Appl. No. 11/820,653 on Aug. 8, 2011.
Office Action issued in U.S. Appl. No. 11/820,600 on May 26, 2011.
Office Action issued in U.S. Appl. No. 10/532,388 on Oct. 1, 2010.
Office Action issued in U.S. Appl. No. 11/501,393 on Nov. 9, 2011.
Office Action issued in U.S. Appl. No. 11/636,867 on Oct. 28, 2011.
Office Action issued in U.S. Appl. No. 12/626,392 on Jul. 8, 2011.
Office Action issued in U.S. Appl. No. 12/331,887 on Oct. 12, 2011.
Office Action issued in U.S. Appl. No. 12/754,820 on Nov. 30, 2011.
Ohkura et al., Japanese Joural of Pharmacognosy, 44(3):171-175, (1990).
Pairet, et al. Inflamm. Res 47, Supplement 2S93-S101 (1998).
Panglisch, Monafsschrift fuer Brauwissen Schaft, 43(1), 4-16 (1990).
Parmar et al., Phytochemistry, vol. 28(2):591-593 (1989).
Parts per Million, 1 page, 2004.
Pippa, et al. Scand. J. Gastroenterol. Suppl. 167:32-35 (1989).
Plewig, et al. J Invest. Dermatol. 65(6):532-536 (1975).
Poullis ,et al. J. Gastroenterol. Hepatol. 18:756-762 (2003).
Provital Group, Rosemary-eco Botany, 2007, 9 pages.
Q & A, (what does ppm or ppb mean?) 3 pages, 2004.
Rahman, M.M., et al., "Conjugated linoleic acid inhibits osteoclast differentiation of RAW264.7 cells by modulating RANKL signaling" J. Lipid Res., 47(8): 1739-1748, (2006).
Ringbom, et al. J. Nat Prod 61:1212-1215 (1998).
Røseth, Digest. Liver Dis. 35:607-609 (2003).
Schjerven, et al. Br. J. Dermatol. 149:484-491 (2003).
Schmalreck et al. Canadian Journal of Microbiology, vol. 21:205-212 (1975).
Shah, et al. Gut 48:339-346 (2001).
Shimamura, et al. Biochem. Biophys. Res. Comm. 289:220-224 (2001).
Shureiqi, et al. Cancer Res. 61:6307-6312 (2001).
Sivri, Fundam. Clinic. Pharmacol. 18:23-31 (2004).
Smith, et al., Natural Foam Stabilizing and Bittering Compounds Derived From Hops, Journal of the American Society of Brewing Chemists, vol. 56, No. 2, 1998, pp. 52-57.
Stephan T E et al., Biochemical Pharmacology, 55(4), pp. 505-514, (Feb. 15, 1998).
Stevens, Xanthohumol and related Prenylflavonoids from Hops and Beer: To Your Good Health, Science Direct, 2pp (2004).
Subbaramaiah, et al. Cancer Res. 60:2399-2404 (2000).
Suh, et al. Cancer Res 58:717-723 (1988).
Supplemental European Search Report for EP 07845228.
Supplementary European Search Report form related EP Application No. 05851567, 8PP.
Supplementary Partial European Search Report for related European Patent Application No. 05723895.8, 5 pages (2007).
Supplementary European Search Report for EP Application No. EP 08729724, 9PP.
Supplementary European Search Report for EP Application No. EP 08859091, 5PP.
Tagashira M et al., Bioscience, Biotechnology, and Biochemistry, 59(4), pp. 740-742 (Apr. 1995).
The national. 3 pages (1999).
Tibble, et al. Drugs Today 37(2):85-96 (2001).
Tibble, et al. Gut 45:362-366 (1999).
Tiktakaghrtam, TKDL, Jan. 1, 1922, XP003024378 (1922).
Tobe, et al. Biosci. Biotech. Biochem 61(1):158-159 (1997).
Turmeric: The Ayurvedic Spice of Life, published at www.bioponic.com/pdfs/TurmericAyurveda.pdf (2003).
US News and world report re Palliative Care, 10 pages (2008).
Van Montfrans et al. Inflammatory Signal Transduction in Crohn's Disease and Novel Therapeutic Approaches. Science Direct, Jun. 2, 2002, 20 pages. Biochemical Pharmacology, vol. 64, issues 5-6.
Vanhoecke et al., In Vivo, vol. 19, No. 1, pp. 103-107 (2005).
Vanhoenacker, et al., Journal of Chromatography, vol. 1035, No. 1, (Apr. 30, 2004), pp. 53-61.
Verzele, et al. Chemistry and analysis of hop and beer bitter acids, Developments in food science, 27, pp. 44-51, 88-139 (1991).
Verzele and De Keukeleire (eds.) Chemistry and Analysis of Hop and Beer Bitter Acids; Elsevier, Chapters 5, 20 pages (1991).
Verzele and De Keukeleire (eds.) Chemistry and Analysis of Hop and Beer Bitter Acids; Elsevier, Chapters 6, 8 pages (1991).
Wang, et al. Free Radical Biology & Medicine 27:612-616 (1999).
Ward, et al., Therapeutic Potential of Phosphoinositide 3-Kinase Inhibitors, Chemistry & Biology, vol. 10, 207-210, Mar. 2003.
Warner, et al. Proc Natl Acad Sci USA 96:7563-7568 (1999).

Written Opinion for corresponding PCT Application No. PCT/US05/41018; 3 pp.
Yamamoto, et al. Abstract—Prostaglandins & Other Lipid Mediators 59:1-235 (1999).
Yamamoto, FEBS Letters 465:103-106 (2000).
Yui, et al. Biol. Pharm. Bull. 26(6):753-760 (2003).
Zhao Feng et al., Biological and Pharmaceutical Bulletin, 26(1), pp. 61-65 (Jan. 2003).

* cited by examiner

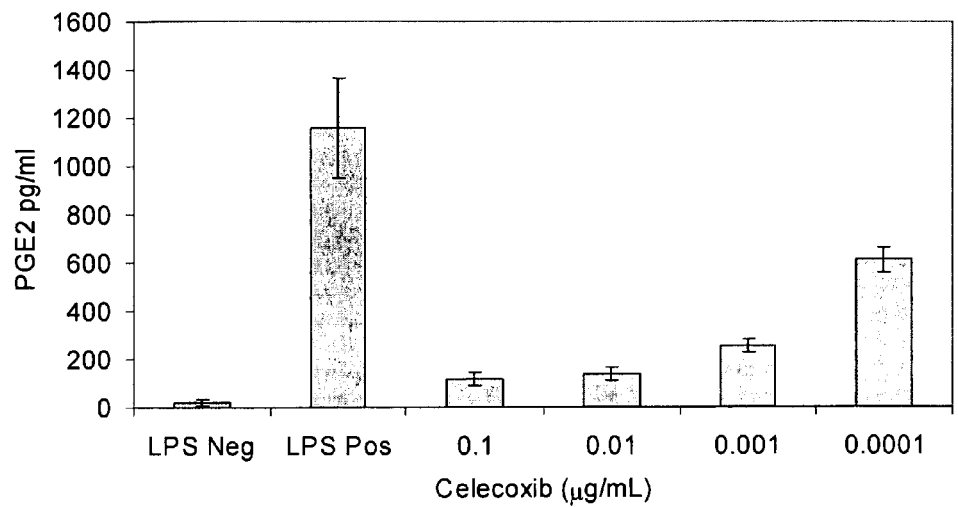
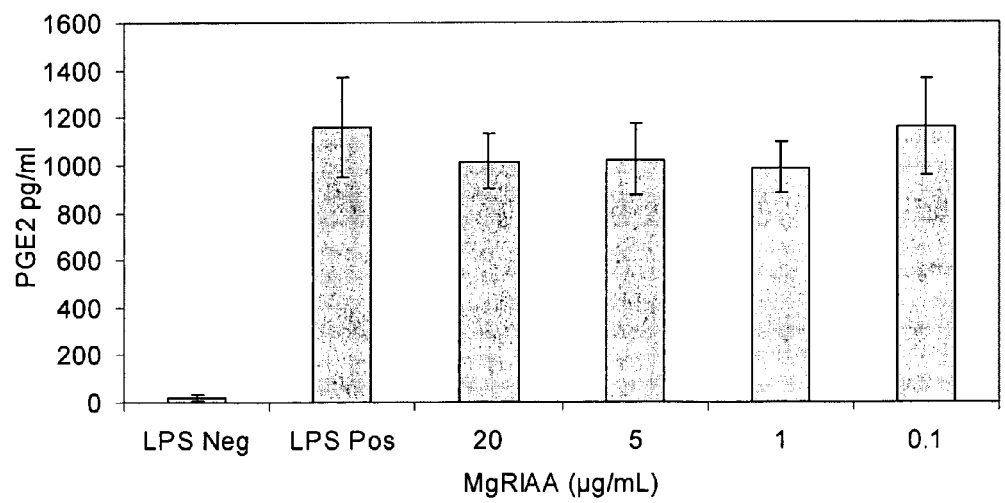
Fig. 5

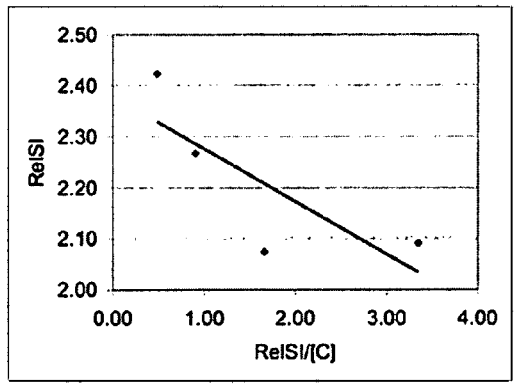
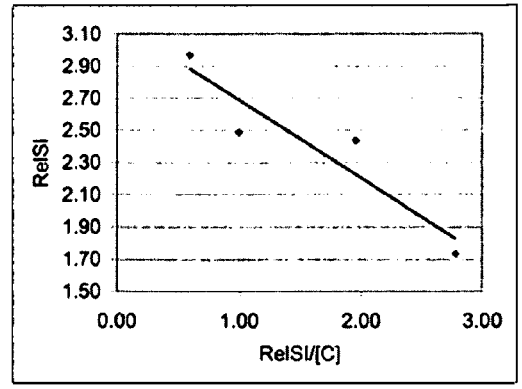
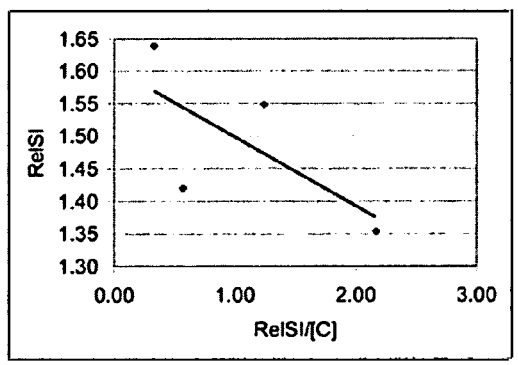
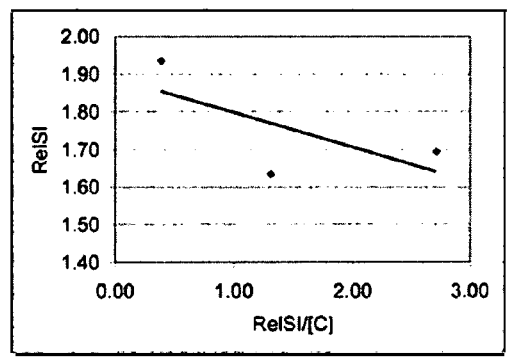
Fig 20 A-D

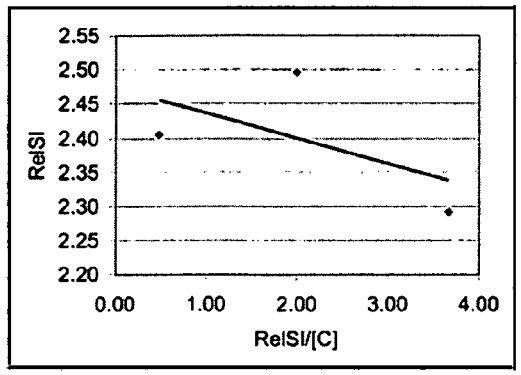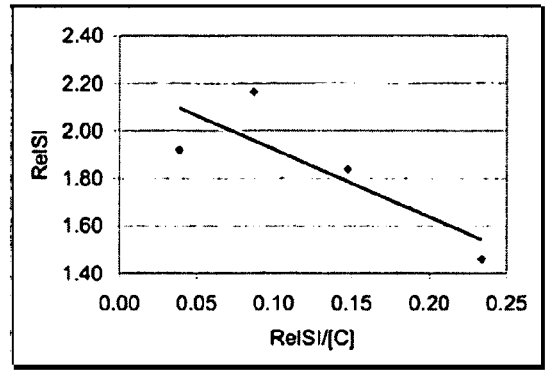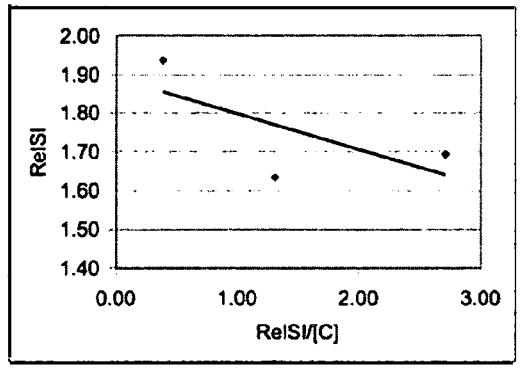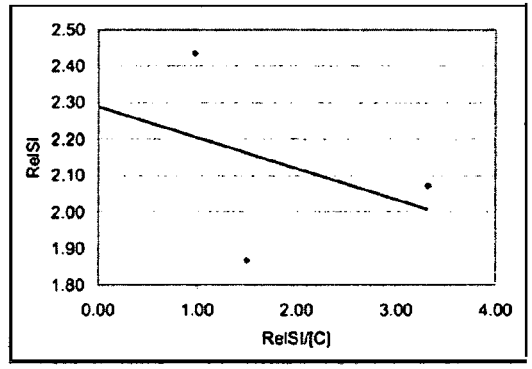
Fig 20 E-H

ANTI-INFLAMMATORY BOTANICAL PRODUCTS FOR THE TREATMENT OF METABOLIC SYNDROME AND DIABETES

CROSS-REFERENCE TO RELATED APPLICATIONS

This patent application claims priority to U.S. provisional application Ser. No. 60/748,907, filed on Dec. 9, 2005. This patent application is a continuation-in-part of U.S. application Ser. No. 10/689,856 filed Oct. 20, 2003 now U.S. Pat. No. 7,270,835, which is a continuation-in-part of U.S. application Ser. No. 10/464,410, filed Jun. 18, 2003 now U.S. Pat. No. 8,142,819, which is a continuation-in-part of U.S. application Ser. No. 10/400,293, filed Mar. 26, 2003 now abandoned, and a continuation-in-part of U.S. application Ser. No. 10/401,283, filed Mar. 26, 2003 now abandoned, both of which claim the benefit under 35 U.S.C. §119(e) to provisional application No. 60/450,237, filed on Feb. 25, 2003, and provisional application No. 60/420,383, filed on Oct. 21, 2002; and is a continuation-in-part of U.S. patent application Ser. No. 10/464,834, filed Jun. 18, 2003 now abandoned, which is a continuation-in-part of U.S. patent application Ser. No. 10/400,293, filed Mar. 26, 2003 now abandoned, and a continuation-in-part of U.S. patent application Ser. No. 10/401,283, filed Mar. 26, 2003 now abandoned, both of which claim the benefit under 35 U.S.C. §119(e) to provisional application No. 60/450,237, filed on Feb. 25, 2003, and provisional application No. 60/420,383, filed on Oct. 21, 2002. This application is also a continuation-in-part of U.S. application Ser. No. 09/885,721, filed Jun. 20, 2001 now U.S. Pat. No. 7,205,151.

BACKGROUND OF THE INVENTION

1. Field of the Invention

The present invention provides compounds, compositions, kits, and methods comprising botanical compounds and extracts for the prevention and treatment of inflammatory and metabolic disorders, in particular, insulin resistance syndromes, diabetes, obesity, weight gain, cardiovascular disease and cancer. More specifically, the invention relates to anti-inflammatory, pharmaceutical compositions and therapeutic methods utilizing such compositions to modify adipocyte physiology to enhance insulin sensitivity.

2. Description of the Related Art

Research has implicated dysregulated inflammatory processes in the pathogenesis of many prevalent, chronic diseases including metabolic syndrome, insulin resistance, diabetes, obesity, dyslipidemia, lipodystrophy and cardiovascular disease. Increased plasma concentrations of tumor necrosis factor alpha (TNFα), interleukin-6 (IL-6), C-reactive protein (CRP) and plasminogen activator inhibitor-1 (PAI-1), which are characteristic of chronic inflammation, are found in varying degrees in all of these pathologies [Dandona, P., et al. Inflammation: the link between insulin resistance, obesity and diabetes. Trends Immunol. 25(1):407, (2004); Dandona, P. Endothelium, inflammation, and diabetes. Curr Diab Rep 2(4):311-315, (2002)]. As such anti-inflammatory directed treatment modalities have the potential to provide therapeutic or palliative benefits for these conditions.

Insulin resistance is now well recognized as a chronic inflammatory state. The interrelationship between inflammation and inflammatory mediators and the diabetic state, whether diabetes type 1 or type 2, has long been noted. For example, insulin dependent diabetes mellitus (IDDM) is characterized by an initial inflammatory response or cellular infiltration in or around the pancreatic islet cells [Gepts, W. Pathologic anatomy of the pancreas in juvenile diabetes mellitus. Diabetes 14: 619-633, (1965); see also Koliopanos, A., et al., Cyclooxygenase 2 expression in chronic pancreatitis: Correlation with stage of the disease and diabetes mellitus. Digestion 64: 240-247, (2001); and Luo, C., et al., Cellular distribution and contribution of cyclooxygenase (COX)-2 to diabetogenesis in NOD mouse. Cell Tissue Res. 310: 169-175, (2002)].

Additionally, Helmersson, et al., demonstrated that type 2 diabetes in elderly men is related to COX-mediated inflammation, as reflected by enhanced prostaglandin formation. The high levels of cytokine-mediated acute-phase proteins observed in men with diabetes appear to be related to obesity and increased fasting insulin. These results reflect the current understanding that the appearance of chronic inflammation is an early process in the pathogenesis of diabetes [Helmersson, J., et al. Association of type 2 diabetes with cyclooxygenase-mediated inflammation and oxidative stress in an elderly population. Circulation 109: 1729-1734, (2004)].

The cyclooxygenase enzymes, which catalyze a critical step in the conversion of arachadonic acid to prostaglandins, are also recognized as important mediators of both acute and chronic inflammation. For example, cyclooxygenase (COX)-2 is overexpressed in chronic pancreatitis, which may play a role in the progression of the disease [Schlosser, W., et al., Cyclooxygenase-2 is overexpressed in chronic pancreatitis. Pancreas 25(1): 26-30, (2002)]. Further, COX-2 inhibition has been shown to prevent IDDM in streptozotocin treated mice [Tabatabai, T., et al., COX-2 inhibition prevents insulin-dependent diabetes in low-dose streptozotocin treated mice. Biochem. And Biophys. Res. Comm. 273: 699-704, (2000)] and in conjunction with other cytokines, such as, for example IL-1β, TNF-α, and IFN-γ, to play a role in cytokine induced β-cell dysfunction in islet inflammation and diabetes [Heitmeier, M. R., et al., Role of cyclooxygenase-2 in cytokine-induced β-cell dysfunction and damage by isolated rat and human islets. J. Bio. Chem. 279(51): 53145-53151, (2004); and McDaniel, M. L., et al., Cytokines and nitric oxide in islet inflammation and diabetes. Proc. Soc. Exp. Biol. Med. 211: 24-32, (1996)].

Corbett and co-workers demonstrated that tyrosine kinase inhibitors prevent IL-1β, TNF-α, and IFN-γ induction of the expression of iNOS and COX-2 by human islet cells and further suggest that the cytokines released during islet inflammation may participate in β-cell destruction in IDDM [Corbett, J. A., et al., Tyrosine kinase inhibitors prevent cytokine-induced expression of iNOS and COX-2 by human islets. Am J. Physiol. 270(6 Pt 1):C1581-7, (June 1996)]. Insofar as IL-1β, TNF-α, and IFN-γ are under NF-κB control, modalities which regulate NF-κB expression may be expected to have a beneficial effect on diabetes through the regulation of iNOS and COX-2 expression and activity. For a review of inflammations and diabetes see Tak, P. P. and Firestein, G. S. INF-κB: a key role in inflammatory diseases. J. Clin. Invest. 107:7-11, (2001) or Yuan, M., et al. Reversal of obesity- and diet-induced insulin resistance with salicylates or targeted disruption of Ikkβ. Science 293: 1673-1677, (2001)].

As previously noted, COX enzymes play a critical role in arachadonic metabolism and prostaglandin synthesis and it has long been known that drugs which inhibit prostaglandin synthesis can improve glucose disposal. Robertson and co-workers have demonstrated a) an in vivo inhibition of insulin secretion by prostaglandin $E_1$, b) a role for prostaglandin $E_2$ in defective insulin secretion and carbohydrate intolerance in diabetes mellitus, and c) that COX-2 is dominant in pancreatic islet prostaglandin synthesis. [Robertson, R. P., et al., Inhibition of in vivo insulin secretion by prostaglandin $E_1$. J. Clin. Invest. 54: 310-315, (1974); Robertson, R. P. and Chen, M. A role for prostaglandin E in defective insulin secretion and carbohydrate intolerance in diabetes mellitus. J. Clin. Invest. 60: 747-753, (1977); and Robertson, R. P. Dominance of cyclooxygenase-2 in the regulation of pancreatic islet prostaglandin synthesis. Diabetes 47: 1379-1383, (1998)]. Additionally, Litherland and co-workers have shown that an antigen presenting T-cell defect in IDDM is defined by aberrant prostaglandin synthase 2 expression [Litherland, S. A., et al., Aberrant prostaglandin synthase 2 expression defines an antigen-presenting cell defect for insulin-dependent diabetes mellitus. J. Clin. Invest. 104: 515-523, (1999)].

Hyperinsulinemia and insulin action were initially proposed as common preceding factors of hypertension, low HDL cholesterol, hypertriglyceridemia, abdominal obesity and altered glucose tolerance, further linking these abnormalities to the development of coronary heart disease in the late 1990s.

The concept of inflammation and adipocyte interaction in relation to these metabolic conditions started with a seminal publication by Hotamisligil et al. in 1993, which demonstrated that adipocytes constitutively express the pro-inflammatory cytokine tumor necrosis factor-α (TNFα), and that TNFα expression in the adipocytes of obese animals (ob/ob mouse, db/db mouse and fa/fa Zucker rat) is markedly increased. Further, neutralization of TNFα by soluble TNFα receptor leads to a decrease in insulin resistance in these animals [Hotamisligil G. S., et al. Adipose expression of tumor necrosis factor-alpha: direct role in obesity-linked insulin resistance. Science 259:87-91, (1993)]. These observations provide a link between an increase in the expression and plasma concentration of a pro-inflammatory cytokine and insulin resistance.

Clinical and experimental data developed since 1993 suggest that all major components of the metabolic syndrome including insulin insensitivity and obesity are associated with inflammatory conditions characterized by increased plasma concentrations of pro-inflammatory cytokines such as TNFα, Interleukin-6 (IL-6), C-reactive protein (CRP) and plasminogen activator inhibitor-1 (PAI-1) [Yudkin, J. S., et al. C-reactive protein in healthy subjects: associations with obesity, insulin resistance, and endothelial dysfunction: a potential role for cytokines originating from adipose tissue? Arterioscler. Thromb. Vasc. Biol. 19:972-978, (1999); Mohamed-Ali, V., et al. Subcutaneous adipose tissue releases interleukin-6, but not tumor necrosis factor-a, in vivo. Endocrinol. Metab. 82:4196-4200, (1997); Lundgren, C. H., et al. Elaboration of type-1 plasminogen activator inhibitor from adipocytes. A potential pathogenetic link between obesity and cardiovascular disease. Circulation 93:106-110, (1996)]. Clinically, it has been shown that human adipose tissue expresses TNFα constitutively and that expression falls after weight loss [Kern, P. A., et al. The expression of tumor necrosis factor in human adipose tissue. Regulation by obesity, weight loss, and relationship to lipoprotein lipase. J. Clin. Invest. 95:2111-2119, (1995)].

The prevalence of diabetes mellitus has increased roughly in parallel with that of obesity, which has itself doubled in the United States in the last twenty years. Some experts have stated that obesity in the United States is an epidemic. In any case, as the population ages, it is likely that the rate of obesity will increase with time. The correlation between obesity and diabetes is manifest, as are the correlations between cardiovascular disease and both obesity and diabetes. A non-obese, type two diabetic is far more likely to suffer from cardiovascular disease than is a non-obese, non-diabetic; and an obese non-diabetic is at an even higher risk for cardiovascular disease than is a non-obese diabetic. Thus, in addition to inflammation, there are apparently causal links between cardiovascular disease and both obesity and diabetes.

It is now generally accepted that adipose tissue acts as an endocrine organ producing a number of biologically active peptides with an important role in the regulation of food intake, energy expenditure and a series of metabolic processes. Adipose tissue secretes a number of bioactive peptides collectively termed adipokines. Through their secretory function, adipocytes lie at the heart of a complex network capable of influencing several physiological processes (FIG. 1). Dysregulation of adipokine production with alteration of adipocyte mass has been implicated in metabolic and cardiovascular complications of obesity. In obese individuals, excessive production of acylation-stimulating protein (ASP), TNFα, IL-6 or resistin deteriorates insulin action in muscles and liver, while increased angiotensinogen and PAI-1 secretion favors hypertension and impaired fibrinolysis. Leptin regulates energy balance and exerts an insulin-sensitizing effect. These beneficial effects are reduced in obesity due to leptin resistance. Adiponectin increases insulin action in muscles and liver and exerts an anti-atherogenic effect. Further, adiponectin is the only known adipokine whose circulating levels are decreased in the obese state. The thiazolidinedione anti-diabetic drugs increase plasma adiponectin, supporting the idea that adipokine-targeted pharmacology represents a promising therapeutic approach to control non-insulin dependent diabetes mellitus (NIDDM), diabetes and cardiovascular diseases in obesity (FIG. 2) [Guerre-Millo, M. Adipose tissue and adipokines: for better or worse. Diabetes Metabolism 30:13-19, (2004)].

Insulin resistance and/or hyperinsulinemia have been postulated to be the cause of the other abnormal metabolic and cardiovascular risk factors that occur in the metabolic syndrome (FIG. 3). These risk factors have been identified as (1) central obesity (including increased visceral fat); (2) a characteristic dyslipidemia that includes an elevated plasma triglyceride, a low plasma high-density lipoprotein (HDL), and a small dense low-density lipoprotein (LDL) cholesterol particle pattern; (3) a procoagulant state made up of elevated plasma fibrinogen and plasminogen activator inhibitor-1; (4) elevated systolic and diastolic blood pressure; (5) hyperuricemia; and (6) microalbuminuria [Lebovitz, H. E., and Banerji, M. A. Insulin resistance and its treatment by thiazolidinediones. Recent Prog Horm Res. 56:265-94, (2001)].

One method for the treatment of insulin resistance is through the use of oral antihyperglycemic agents. Oral antihyperglycemic agents can be classified into six, distinct classes based upon mechanism of action: (1) biguanides, such as metformin, that decrease hepatic glucose production; (2) sulfonylureas such as glipizide, glyburide, and glimepiride, and (3) nonsulfonylureas such as repaglinide and nateglinide that increase pancreatic insulin secretion; (4) α-glucosidase inhibitors, with acarbose being the only representative on the market, that delay intestinal carbohydrate absorption; (5) thiazolidinediones, rosiglitazone and pioglitazone, agents that increase fatty acid uptake of adipocytes as well as glucose uptake in both muscle and fat; and 6) anti-inflammatories (e.g. aspirin (not used due to toxicity associated with the levels necessary to improve glucose control)) [Scheen, A. J. Drug treatment of non-insulin-dependent diabetes mellitus in the 1990s. Achievements and future developments. Drugs 54(3):355-368, (September 1997); Scheen, A. J. and Lefebvre, P. J. Antihyperglycaemic agents. Drug interactions of clinical importance. Drug Saf; 12(1):32-45, (January 1995); Inzucchi, S. E. Oral antihyperglycemic therapy for type 2 diabetes: scientific review. JAMA. 287(3):360-372, (Jan. 16, 2002); and Gao, Z., et al. Aspirin inhibits serine phosphorylation of insulin receptor substrate 1 in tumor necrosis factor-treated cells through targeting multiple serine kinases. J. Bio. Chem. 278(27): 24944-24950, (2003)].

With few exceptions, the available antidiabetic drugs are equally effective at lowering glucose concentrations. Due to their differing mechanisms of action, they appear to have distinct metabolic effects as reflected in their effect on cardiovascular risk and adverse effect profiles. Metformin currently is the only drug associated with weight loss (or no effect on body weight); it has become the most widely prescribed single hyperglycemic drug and is generally regarded as the best first-line agent especially in the obese patient without contraindications for its use.

Failure to maintain adequate blood glucose for extended periods of time, however, is frequently seen independent of choice of drug. For example, sulphonylureas have a secondary failure rate of up to 10% each year. This associated worsening hyperglycemia often necessitates the use of polypharmacy; i.e. three years after diagnosis, approximately half of patients require more than one pharmaceutical agent and within nine years this increases to 75% of all patients [Turner, R. C., Cull, C. A., Frighi, V., and Holman, R. R. Glycemic control with diet, sulfonylurea, metformin, or insulin in patients with type 2 diabetes mellitus: progressive requirement for multiple therapies (UKPDS 49). UK Prospective Diabetes Study (UKPDS) Group. JAMA. 281(21):2005-2012, (Jun. 2, 1999)]. Moreover, despite the use of combination therapy physicians generally do not reach targets for glycemic control [Zinman, B. PPARgamma agonists in type 2 diabetes: how far have we come in preventing the inevitable'? A review of the metabolic effects of rosiglitazone. Diabetes Obes Metab. 3 Suppl 1:34-43, (August 2001)].

Statistics on the increasing incidence of NIDDM and the rate of therapeutic failures in maintaining adequate blood glucose indicate that new approaches in the treatment of NIDDM and its complications are important public health priorities. Although diet, regular exercise and weight control have proven effective for modifying the pathogenesis of insulin resistance and increasing the efficacy of antidiabetic drugs, it can be anticipated that a majority of persons will eschew dietary modifications and exercise and that monotherapy will ultimately fail to adequately control the myriad of metabolic imbalances manifest in NIDDM. In light of the tremendous cost of NIDDM, both in terms of human suffering and monetary resources, it seems highly desirable to have additional agents to support treatment [McCarty, M. F. Nutraceutical resources for diabetes prevention—an update. Med. Hypotheses. 64(1):151-158, (2005); McCarty, M. F. Toward practical prevention of type 2 diabetes. Med Hypotheses. 54(5):786-793, (May 2000)].

In addition to diabetes, obesity and cardiovascular disease, other conditions are now recognized as inflammatory pathologies. These include (1) diseases of the digestive organs such as ulcerative colitis, Crohn's disease, pancreatitis and gastritis; (2) proliferative diseases, such as benign tumors, polyps, hereditary polyposis syndrome, colon cancer, rectal cancer, breast cancer, prostate cancer, and stomach cancer; and (3) ulcerous disease of the digestive organs, and (4) cardiovascular pathologies including stenocardia, atherosclerosis, myocardial infarction, sequelae of stenocardia or myocardial infarction, senile dementia, and cerebrovascular diseases. Thus, it is to be expected that effective anti-inflammatory based methods of improving insulin sensitivity will be useful in the treatment, prevention or delay of onset of one or more of the foregoing inflammatory disorders. Botanical based anti-inflammatory compounds and extracts represent an as yet underutilized source for palliative or preventive treatment modalities.

Folk and herbal medicine, such as for example, Ayurvedic medicine, have ascribed many healing properties to, and resulting from, the use of numerous and varied botanical compounds and extracts. Current research has demonstrated that many of these claims are based on more than a factual grain of truth. Two such botanical sources are hops (members of the genus *Humulus*) and acacia (members of the botanical genus *Acacia*).

Hops, long known to the brewers' art for providing the bitter taste to beers, have had many health benefits ascribed to its use. Such benefits include antioxidant activity, anti-inflammatory effects, anticarcinogenic activity, etc. See, for example, Gerhauser, C. Beer constituents as potential cancer chemopreventative agents. Eur. J. of Cancer, 41(13):1941-54, (2005).

*Acacia* is a genus of leguminous trees and shrubs. The genus *Acacia* includes more than 1000 species belonging to the family Leguminosae and subfamily Mimosoideae. *Acacias* are distributed worldwide in tropical and subtropical areas of central and South America, Africa, parts of Asia, as well as Australia (which has the largest number of endemic species). *Acacias* occur primarily in dry and arid regions, where the forests are often in the nature of open thorny shrubs.

*Acacia catechu* is believed to have antiseptic and astringent qualities. Preparations are usually in the form of an alcohol solution (tincture), which can be taken internally, used in a mouthwash, or painted directly onto inflamed tissues in the mouth. Traditional medicine supports its oral use for the following indications: sore throat, gingivitis, colitis, diarrhea, bleeding, diabetes, skin diseases, cancer, toothaches and inflammation in the mouth. Singh, [Singh, K. N., et al., Hypoglycaemic activity of *Acacia catechu, Acacia suma*, and *Albizzia odoratissima* seed diets in normal albino rats. Ind. J. Med. Res 64: 754-757, (1976)] discloses that a diet of seeds from these *Acacia* plants had hypoglycemic activity in normal rats but not in alloxan induced diabetic rats. Singh however neither teaches nor addresses whether portions of the plants other than the seed meat, for example bark or heartwood, or plant material extracts have any hypoglycemic activity in either normal or diabetic subjects.

*Catechu* is used orally in some parts of the world as an anti-fertility drug. Topically, catechu is used for skin diseases, hemorrhoids, traumatic injuries, to stop bleeding and for dressing wounds. *Catechu* has been included in mouthwashes and gargles for gingivitis, stomatitis, pharyngitis, and oral ulcers. In foods and beverages, it is used as a flavoring agent. However, *Acacia catechu* is not well researched and little is known regarding the full spectrum or identification of potentially pharmaceutically active compounds.

Aqueous infusions of the seed pods or bark of *Acacia nilotica* have been used in folk medicine for gastrointestinal disorders while pulverized seeds and pods have been applied to sores of the mouth or to hasten cicatrisation of syphilitic ulcers [Amos, S., The pharmacological effects of an aqueous extract from *Acacia nilotica* seeds. Phytother. Res. 13: 683-685, (1999), and Al-Mustafa, Z. H. and Dafallah, A. A. A study on the toxicology of *Acacia nilotica*. Am. J. Clin. Med. 28(1): 23-29, (2000)]. Nor are *Acacia* species the only botanicals purportedly to have antidiabetic properties.

Another botanical, *Momordica charantia* (bitter melon), is used primarily as an alternative therapy for diabetes. A member of the Curcurbitaceae family, the plant grows in tropical areas, including parts of the Amazon Basin, Africa, Asia, the Caribbean, and South America. Bitter melon has a long history of use as a hypoglycemic agent in Asia, Africa, and Latin America, where the plant extract has been referred to as vegetable insulin. Other botanicals of interest include African cucumber, balsam-apple, balsambirne, balsam pear, balsamo, betamomorcharin, bitter apple, bitter cucumber, bitter gourd, bittergurke, carilla gourd, charantin, chinli-chih, cundeamor, kakara, kuguazi, k'u-kua, lai margose. Four clinical trials have found bitter melon juice, fruit, and dried powder to have a moderate hypoglycemic effect. Data from in vitro, animal and several human studies do suggest that bitter melon and some of its crude extracts have a moderate hypoglycemic effect. These clinical studies, however, were small and were not randomized or double-blinded. Reported adverse effects of bitter melon include hypoglycemic coma and convulsions in children, reduced fertility in mice, a favism-like syndrome, increases in γ-glutamyltransferase and alkaline phosphatase levels in animals, and headaches [Basch, E., et al. Bitter melon (*Momordica chanantia*): A review of efficacy and safety. Am J Health-Syst Pharm 60:356-359, (2003)]. Thus, compositions or methods to increase the clinical efficacy of bitter melon while decreasing the dose would be useful for the treatment of type 2 diabetes or metabolic syndrome.

Aloe vera has been promoted for a large variety of medical conditions ranging from burns to constipation. Published work in animals combined with the limited clinical research suggests that oral administration of aloe vera might be a useful adjunct for lowering blood glucose in diabetic patients as well as for reducing blood lipid levels in patients with hyperlipidemia [Eshun, K. Aloe vera: a valuable ingredient for the food, pharmaceutical and cosmetic industries—a review. Crit Rev Food Sci Nutr. 44(2):91-96, (2004).]. However, clinical effectiveness of oral or topical aloe vera is not sufficiently defined at present. Ultimately, the most effective use of aloe vera in diabetes or metabolic syndrome may be in combination with other materials.

Germacrene A and Germacrene D are sesquiterpenes found in a wide variety of plants and exhibit anti-ulcer, anti-inflammatory, anti-fungal and anti-bacterial activity. To date no research has demonstrated that these compounds exhibit hypoglycemic or insulin sensitizing properties.

Red raspberry seed oil (*Rubus idaeus*) is an excellent dietary source of potent antioxidants, including gamma-tocopherol, the most active form of Vitamin E plus linoleic, linolenic and palmitic acids. Limited in vitro research has demonstrated that it possesses anti-inflammatory properties. The natural tocopherol content of red raspberry seed oil is very high, which may aid in the prevention of oxidative stress.

Wasabi (*Wasabi japonica*) is used as a spice in daily foodstuffs. Allylisothiocyanate (AIT) is a potent component of wasabi and is formed by plant enzymes following preparation by grating. It is known that AIT shows inhibitory effects on the growth of food poisoning bacteria and fungi. Several functional properties of roots and leaves from wasabi have been examined in vitro. Wasabi has shown peroxidase activity and has also exhibited antioxidative and superoxide scavenging potency. The antimutagenic activity of wasabi was observed toward 2-amino-3,8-dimethylimidazo[4,5-f]quinoxaline, a well-known mutagen/carcinogen in broiled fish and meat. It also decreased His+ revertant colonies of 3-chloro-4-dichloromethyl-5-hydroxy-2(5H)-furanone (MX) in the Ames test with (−)-(R)-7-methylsulfinylheptyl isothiocyanate identified as the anti-mutagen. These data suggest that wasabi might be a potent functional food source for maintaining human health.

Davana oil is obtained from the air-dried, aerial parts of *Artemisia pallens*. The herb grows in the same parts of southern India where sandalwood is grown. Its odor is sharp, penetrating, bitter-green, foliage like and powerfully herbaceous with a sweet balsamic, tenacious undertone. While used primarily in the perfume industry, the essential oil possesses antibacterial and antifungal properties. The oil contains a variety of terpenoids and the germacranolides 4,5β-epoxy-10α-hydroxy-1-en-3-one-trans-germacran-6α,12-olide and 4,5β-Epoxy-10α-hydroxy-1-en-3-one-trans-germacran-6α, 12-olide [Pujar, P. P., et al. A new germacranolide from *Artemisia pallens* Fitoterapia 71:590-592, (2000)].

*Bacopa monniera* (BM), a traditional Ayurvedic medicine, has been used for centuries as a memory enhancing, anti-inflammatory, analgesic, antipyretic, sedative and antiepileptic agent. The plant, plant extracts and isolated bacosideA3 (3beta,16beta,23R)-16,23:16,30-Diepoxy-20-hydroxydammar-24-en-3-yl O-alpha-L-arabinofuranosyl-(1-2)-O-(beta-D-glucopyranosyl-(1-3))-beta-D-glucopyranoside), the major active principle, have been investigated for their neuropharmacological effects and a number of reports are available ascribing their nootropic action. In addition, researchers have evaluated the anti-inflammatory, cardiotonic and other pharmacological effects of BM preparations/extracts.

Oleoresin Fennel is a volatile oil distilled from fennel (the seeds of *Foeniculum vulgare*), used as a flavoring agent for pharmaceuticals and formerly as a carminative. The best varieties of fennel yield from 4 to 5 percent of volatile oil (sp. gr. 0.960 to 0.930), the principal constituents of which are anethol (1-methoxy-4-propenylbenzene, 50 to 60 percent) and fenchone (1,3,3-trimethyl-2-norcamphanone, 18 to 22 percent). Fenchone is a colorless liquid possessing a pungent, camphoraceous odor and taste, and when present gives the disagreeable bitter taste to many of the commercial oils. It has been postulated that this contributes materially to the medicinal properties of the oil, hence only such varieties of fennel as contain a good proportion of fenchone are suitable for medicinal use. There are also present in oil of fennel, d-pinene, phellandrine, anisic acid and anisic aldehyde. Limonene is also at times present as a constituent.

*Centella asiatica*, is a botanical that has wound healing and anti-aging properties. Asiaticoside (2alpha,3beta,23-Trihydroxy-urs-12-en-28-saeure(O-alpha-L-rhamnopyranosyl-(1-4)-O-beta-D-glucopyranosyl-(1-6)-O-beta-D-glucopyranosyl)ester) has been derived from the plant *Centella asiatica* and is known to possess wound healing activity where the enhanced healing activity has been attributed to increased collagen formation and angiogenesis.

For thousands of years the beneficial properties of the neem tree (*Azadirachta indica*) have been recognized in India, and it is perhaps the country's most useful traditional plant. Neem has been "universally" accepted as a wonder tree because of its diverse utility. Over 700 herbal preparations based on neem are found in Ayurveda, Siddha, Unani, Amchi and other local health traditions; over 160 local practices are known in different parts of the country in which neem forms an important or sole ingredient in curing or treating various human ailments or disorders. Aqueous leaf extracts have been shown to reduce hyperglycemia in streptozotocin-induced diabetes, and this effect is possibly due to the presence of a flavonoid, quercetin. A leaf extract of *A. indica* has also been reported to block the effects of epinephrine on glucose metabolism and reduce peripheral glucose utilization in diabetic rats, and to some extent in normal rats; this indicates the antihyperglycemic potential of the plant. The hypoglycemic effects of neem-leaf extract and seed oil in normal and alloxan-induced diabetic rabbits has also been reported. The effect, however, was more pronounced in diabetic animals where administration for four weeks after alloxan-induced diabetes significantly reduced blood glucose levels. The hypoglycemic effect was found to be comparable to that of the sulfonylurea glibenclamide. Pretreatment with an *A. indica* leaf extract or seed oil administration started two weeks prior to alloxan partially prevented the rise in blood glucose levels relative to control diabetic animals. The results suggest that *A. indica* could be of benefit in diabetes mellitus for controlling the blood sugar or may also be helpful in preventing or delaying the onset of the disease [reviewed in Brahmachari, G. Neem—an omnipotent plant: a retrospection. Chembiochem. 5(4):408-421, (Apr. 2, 2004)]. However, since neem contains a plethora of phytochemicals with unknown effects with chronic administration, it would be beneficial to reduce the dose of neem through the combination with a well-defined material.

A yellow, pigmented fraction isolated from the rhizomes of *Curcuma longa* contains curcuminoids belonging to the dicinnamoyl methane group. Curcuminoids are present to the extent of 3 to 5 percent. They are considered the most important active ingredients and are believed to be responsible for the biological activity of *Curcuma longa*. Though their major activity is anti-inflammatory, curcuminoids have been reported to possess antioxidant, anti-allergic, wound healing, antispasmodic, antibacterial, antifungal and antitumor activity as well. Curcumin was isolated in 1815 and structurally defined in 1910. Other curcuminoids isolated from *Curcum longa* include demethoxycurcumin, bisdemethoxycurcumin, a cis-trans geometrical isomer of curcumin, and cyclocurcumin. Curcuminoids may be found in other botanicals in addition to *Curcuma longa*, such as *Curcuma xanthorrhiza* and *Curcuma zedoaria*.

Curcuminoids are well known for their anti-inflammatory activity. Tumeric is one of the oldest anti-inflammatory drugs used in Ayurvedic medicine. The anti-inflammatory activity of curcuminoids has been evaluated in inflammatory reaction models such as chemical or physical irritants like carrageenin, cotton pellets, formaldehyde and the granuloma pouch. A *Curcuma longa* rhizome ethanol extract significantly suppressed an increase in blood glucose level in type 2 diabetic KK-A(y) mice. In an in vitro evaluation, the extract stimulated human adipocyte differentiation in a dose-dependent manner and showed human peroxisome proliferator-activated receptor (PPAR)-gamma ligand-binding activity in a GAL4-PPAR-gamma chimera assay. The main constituents of the extract were identified as curcumin, demethoxycurcumin, bisdemethoxycurcumin, and ar-turmerone, which had also PPAR-gamma ligand-binding activity [Kuroda, M., Mimaki, Y., et al. Hypoglycemic effects of turmeric (*Curcuma longa* L. Rhizomes) on genetically diabetic KK-Ay mice. Biol Pharm Bull 28(5): 937-939, (2005)].

However, chronic dosing of curcuminoids may cause stomach distress and irritation due to the fact that curcuminoids act on prostaglandin production in a manner similar to that of aspirin and aspirin-like anti-inflammatory agents. Thus, it would be desirable to reduce the dose of curcuminoids by having a combination of curcuminoids with other hypoglycemic agents that function synergistically to increase insulin activity.

Conjugated linoleic acid (CLA) is a nonessential fatty acid consisting of approximately 20 closely related fatty acid isomers. CLA refers to a group of polyunsaturated fatty acids that exist as positional and stero-isomers of conjugated dienoic octadecadienoate (18:2). CLA comes in two isomers, the 9,11 isomer which appears responsible for improving muscle growth and the 10,12 isomer which primarily prevents lipogenesis (storage of fat in adipose tissue). Most supplements sold in stores contain a 50/50 mix of both isomers.

Various antioxidant and antitumor properties have been attributed to CLA, however it is suspected that an anti-inflammatory concentration within human tissues may not be attainable via oral consumption. Many studies on CLA in humans include the tendency for reduced body fat, particularly abdominal fat, changes in serum total lipids and decreased whole body glucose uptake. Dietary CLA supplementation shows to be safe and does not seem to have any adverse effects. The maximum response to reduce body fat mass was achieved with a 3.4 g daily dose. Some studies in humans, however, have demonstrated a decrease in insulin sensitivity resulting from high does of CLA. It would be desirable to have combinations of CLA that do not decrease insulin action. Further, it would also be desirable to have combinations of CLA that could extend the usefulness of CLA to other chronic inflammatory diseases such as osteoporosis.

Despite advances in treating diabetes mellitus in recent years, there remains a need for compositions for treatment and prevention of diabetes and diabetes-related conditions and disorders, such as insulin resistance and metabolic syndrome X. With the aforementioned increase in the incidence of obesity, compositions and methods for treatment and prevention of obesity are also needed. There is also a need for effective compositions and methods for preventing and treating cardiovascular disease, including prevention and treatment of atherosclerosis. Additionally, given the identification of multiple conditions that can be envisioned as primarily inflammatory conditions, there is a need for compositions and methods useful in the treatment and prevention of inflammation related to a number of disorders. Finally, there is a pressing need to identify compounds which, in addition to their own activity, can augment, synergize, or otherwise extend the efficacy of current first line treatment modalities for diabetes and diabetes related conditions and disorders. The present invention satisfies these needs and provides related advantages as well.

SUMMARY OF THE INVENTION

The invention provides methods for modifying adipocyte physiology in a subject, comprising administering to the subject a botanical compound or extract, or pharmaceutically acceptable salts or mixtures thereof. The present invention further relates to the unexpected discovery that several botanical compounds and extracts, preferably those from acacia or hops increase adipocyte lipogenesis. Preferred embodiments provide compositions and methods for enhancing adipocyte lipogenesis utilizing either single botanical compounds or mixtures thereof. Compositions and methods of the invention can also increase secretion of adiponectin from adipocytes in the presence of high insulin concentrations or in inflammatory states. Additionally disclosed are methods, kits, and compositions able to synergize and augment the activity of a number of pharmaceutical agents currently used for the treatment of diabetes and diabetes related conditions and disorders.

A first embodiment of the invention discloses methods for adipocyte modification for the treatment of insulin related disorders in a subject in need. These methods comprise administering to the subject a composition comprising a therapeutically effective amount of a pharmaceutically acceptable botanical product, where the botanical product is a compound or extract derived from the group consisting of Germacrene A, Germacrene D, red raspberry seed oil, wasabi powder, Davana oil, *Bacopa monniera*, Oleoresin fennel, and *Centella asiatica*.

Another embodiment is directed to compositions for adipocyte modification for the treatment of insulin related disorders in a subject in need. The compositions employed comprise a therapeutically effective amount of a pharmaceutically acceptable botanical product, where the botanical product is a compound or extract derived from the group consisting of Germacrene A, Germacrene D, red raspberry seed oil, wasabi powder, Davana oil, *Bacopa monniera*, Oleoresin fennel, and *Centella asiatica*.

A further embodiment of the invention discloses methods for adipocyte modification for the treatment of insulin related disorders in a subject in need of such treatment where the methods comprise treating the subject with a composition comprising a therapeutically effective amount of a pharmaceutically acceptable botanical product, where the botanical product is a compound or extract derived from acacia or hops.

In another embodiment, compositions for adipocyte modification for the treatment of insulin related disorders in a subject in need are disclosed. Here the compositions comprise a therapeutically effective amount of a pharmaceutically acceptable botanical product, where the botanical product is a compound or extract derived from acacia or hops, wherein the acacia derived botanical product is derived from *Acacia catechu* or *Acacia nilotica*; and wherein the botanical product derived from hops is selected from the group consisting of prenylflavonoids, chalcones, reduced isoalpha acids, dihydro-isoalpha acids, tetra-hydroisoalpha acids, hexa-hydroisoalpha acids, xanthohumol, isoxanthohumol, 6-prenylnaringen, and 8-prenylnaringenin A further embodiment of the invention is directed to methods for the treatment of insulin related disorders in a subject in need where the method comprises administering to the subject a therapeutically effective amount of a pharmaceutically acceptable botanical product and a drug for regulating insulin levels or sensitivity in a subject.

Another embodiment discloses compositions for the treatment of insulin related disorders in a subject in need. These compositions comprise a therapeutically effective amount of a pharmaceutically acceptable botanical product and a drug for regulating insulin levels or sensitivity in a subject, wherein the botanical product is a compound or extract derived from acacia or hops, and wherein the acacia derived botanical product is derived from *Acacia catechu* or *Acacia nilotica*; and wherein the botanical product derived from hops is selected from the group consisting of prenylflavonoids, chalcones, reduced isoalpha acids, dihydro-isoalpha acids, tetra-hydroisoalpha acids, hexa-hydroisoalpha acids, xanthohumol, isoxanthohumol, 6-prenylnaringen, and 8-prenylnaringenin.

A kit for use in the treatment of insulin related disorders in a subject in need is disclosed in another embodiment. The kit disclosed herein comprises a therapeutically effective amount of a pharmaceutically acceptable botanical product and a drug for regulating insulin levels or sensitivity in a subject, wherein the botanical product is a compound or extract derived from acacia or hops; wherein the acacia derived botanical product is derived from *Acacia catechu* or *Acacia nilotica*; and wherein the botanical product derived from hops is selected from the group consisting of prenylflavonoids, chalcones, reduced isoalpha acids, dihydro-isoalpha acids, tetra-hydroisoalpha acids, hexa-hydroisoalpha acids, xanthohumol, isoxanthohumol, 6-prenylnaringen, and 8-prenylnaringenin.

Another embodiment of the invention discloses a method for adipocyte modification for the treatment of insulin related disorders in a subject in need thereof, said method comprising administering to the subject a composition comprising a therapeutically effective amount of a pharmaceutically acceptable botanical product, wherein the botanical product is a compound or extract derived from acacia or hops, wherein the acacia derived botanical product is derived from *Acacia catechu* or *Acacia nilotica*; and wherein the botanical product derived from hops is selected from the group consisting of prenylflavonoids, chalcones, reduced isoalpha acids, dihydro-isoalpha acids, tetra-hydroisoalpha acids, hexa-hydroisoalpha acids, xanthohumol, isoxanthohumol, 6-prenylnaringen, and 8-prenylnaringenin.

In yet another embodiment, a composition for adipocyte modification for the treatment of insulin related disorders in a subject in need thereof is disclosed. This composition comprises a therapeutically effective amount of a pharmaceutically acceptable botanical product, wherein the botanical product is a compound or extract derived from acacia or hops, wherein the acacia derived botanical product is derived from *Acacia catechu* or *Acacia nilotica*; and wherein the botanical product derived from hops is selected from the group consisting of prenylflavonoids, chalcones, reduced isoalpha acids, dihydro-isoalpha acids, tetra-hydroisoalpha acids, hexa-hydroisoalpha acids, xanthohumol, isoxanthohumol, 6-prenylnaringen, and 8-prenylnaringenin.

BRIEF DESCRIPTION OF THE DRAWINGS

FIG. 5 provides a graphic representation of direct enzymatic inhibition of celecoxib [panel A] and MgRIAA [panel B] on LPS induced COX-2 mediated PGE2 production was analyzed in RAW cells. PGE2 was measured and expressed in pg/ml. The error bars represent the standard deviation (n=8).

FIG. 20 depicts the Hofstee plots for [A] Rho isoalpha acids, [B] isoalpha acids, [C] tetrahydroisoalpha acids, [D] hexahydroisoalpha acids, [E] xanthohumols, [F] spent hops, [G] hexahydrocolupulone and the positive control [H] troglitazone. Maximum adiponectin secretion relative to the solvent control was estimated from the y-intercept, while the concentration of test material necessary for half maximal adiponectin secretion was computed from the negative value of the slope.

DETAILED DESCRIPTION OF THE INVENTION

Figure 1:
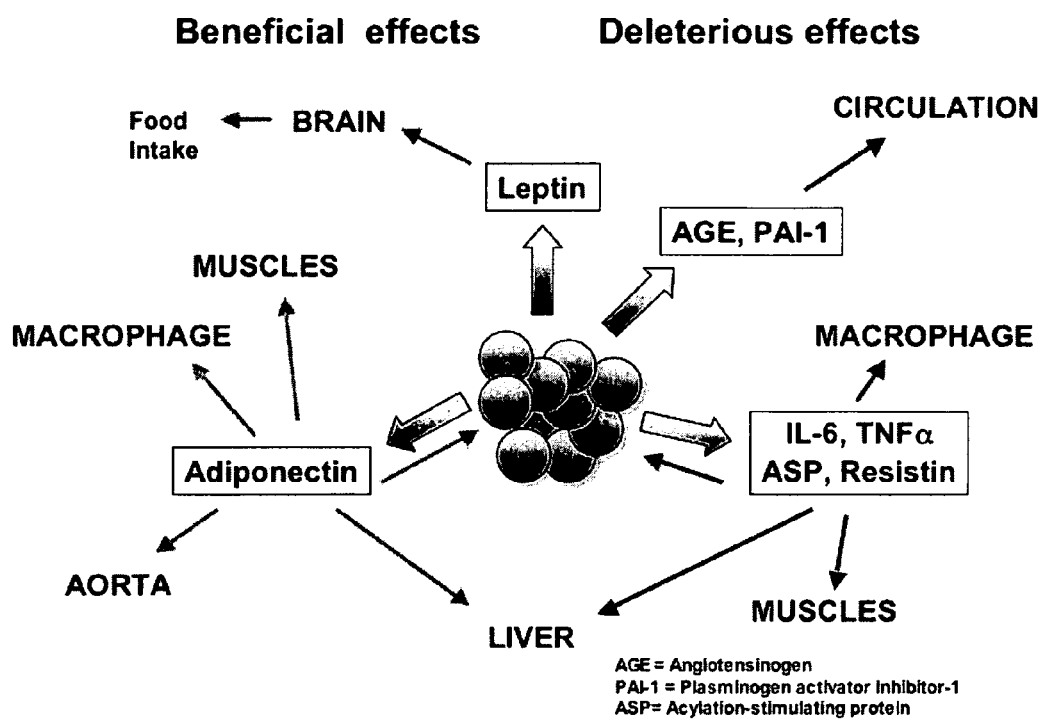
FIG. 1 illustrates the beneficial and deleterious effects of adipose secreted factors implicated in energy homeostasis, insulin sensitivity and vascular homeostasis. Adapted from Guerre-Millo, M. Adipose tissue and adipokines: for better or worse. Diabetes Metabolism 30:13-19, (2004).
Figure 2:
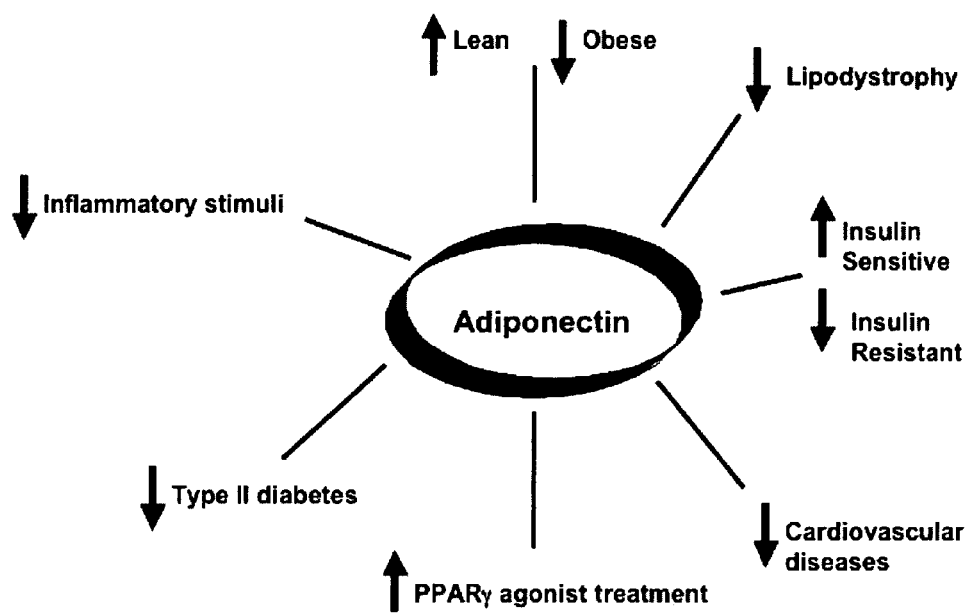
FIG. 2 is a summary of the most important factors and disease states that lead to an up-regulation (upward pointing arrow) or down-regulation (downward pointing arrow) of adiponectin in adipose tissue. Adapted from Trujillo, M. E and Scherer, P. E. Adiponectin—journey from an adipocyte secretory protein to biomarker of the metabolic syndrome. Journal of Internal Medicine 257:167-175, (2005).
Figure 3:
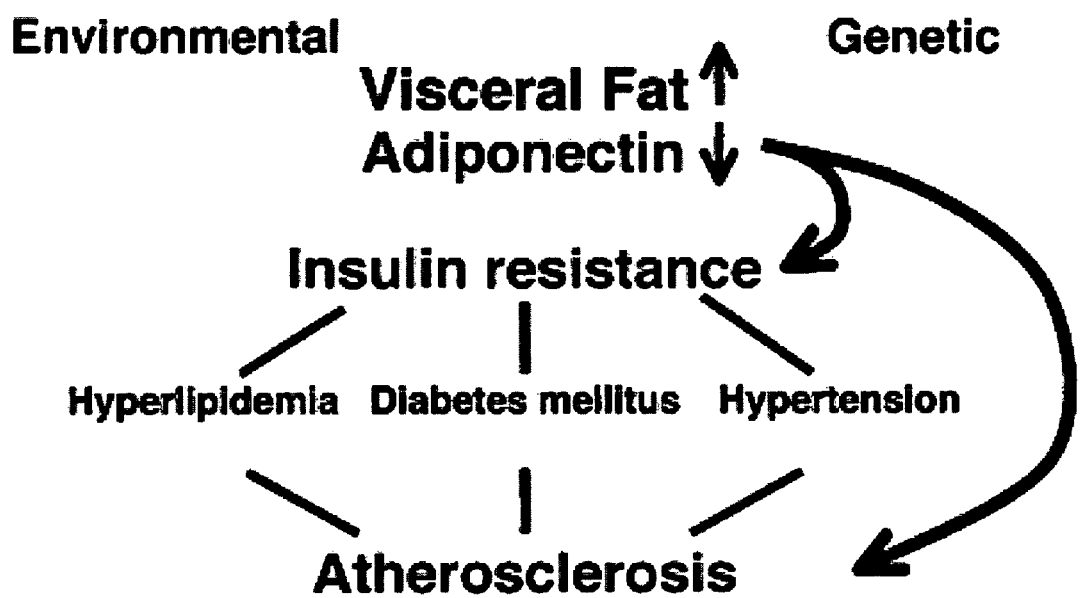
FIG. 3 provides a schematic of the relationship of the pathophysiolgical components of the metabolic syndrome.

The invention provides methods, compounds, compositions, and kits for modifying adipocyte physiology in a subject. The compositions, compounds, and methods comprise administering to the subject a botanical compound or extract, or pharmaceutically acceptable salts or mixtures thereof. The present invention relates to the unexpected discovery that several botanical compounds and extracts, preferably those from acacia or hops increase adipocyte lipogenesis. Preferred embodiments provide compositions and methods for enhancing adipocyte lipogenesis utilizing either single botanical compounds or mixtures thereof. Compositions and methods of the invention can also increase secretion of adiponectin from adipocytes in the presence of high insulin concentrations or in inflammatory states. Additionally disclosed are methods, compositions and kits to synergize and augment the activity of a number of pharmaceutical agents used for the treatment of diabetes.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of recombinant DNA technology include Sambrook et al., Molecular Cloning: A Laboratory Manual, 2nd Ed., Cold Spring Harbor Laboratory Press, New York (1989); Kaufman et al., Eds., Handbook of Molecular and Cellular Methods in Biology in Medicine, CRC Press, Boca Raton (1995); McPherson, Ed., Directed Mutagenesis: A Practical Approach, IRL Press, Oxford (1991). Standard reference works setting forth the general principles of pharmacology include Goodman and Gilman's The Pharmacological Basis of Therapeutics, 10th Ed., McGraw Hill Companies Inc., New York (2001).

In the specification and the appended claims, the singular forms include plural referents unless the context clearly dictates otherwise. As used in this specification, the singular forms "a," "an" and "the" specifically also encompass the plural forms of the terms to which they refer, unless the content clearly dictates otherwise. Additionally, as used herein, unless specifically indicated otherwise, the word "or" is used in the "inclusive" sense of "and/or" and not the "exclusive" sense of "either/or." The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail, in order not to unnecessarily obscure the present invention.

Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

A first embodiment of the invention discloses methods for the treatment of insulin related disorders in a subject in need, this method comprising administering to the subject a composition comprising a therapeutically effective amount of a pharmaceutically acceptable botanical product, wherein the botanical product is a compound or extract derived from the group consisting of acacia, hops, Germacrene A, Germacrene D, red raspberry seed oil, wasabi powder, Davana oil, *Bacopa monniera*, Oleoresin fennel, and *Centella asiatica*.

In some aspects of this embodiment the adipocyte modification is the improved secretion of adiponectin while in other aspects the modification is a modification of adipocyte physiology.

In aspects of this embodiment, the insulin related disorder is selected from the group consisting of diabetes, diabetic complications, insulin sensitivity, hyperglycemia, dyslipidemia, insulin resistance, metabolic syndrome, obesity and body weight gain.

In yet other aspects, the acacia derived botanical product is derived from *Acacia catechu* or *Acacia nilotica*. In those aspects where the acacia derived botanical product is derived from *Acacia catechu* or *Acacia nilotica*, the *Acacia catechu* or *Acacia nilotica* product is selected from the group consisting of gum resin, bark powder, heartwood powder, and an *Acacia catechu* or *Acacia nilotica* extract. In those aspects where the acacia derived botanical product is an *Acacia catechu* or *Acacia nilotica* extract, the extract is selected from acidic, alkaline, polar solvent, nonpolar solvent, and gastric fluid extracts.

In some methods of this embodiment, the composition used comprises a botanical product derived from hops selected from the group consisting of prenylflavonoids, chalcones, reduced isoalpha acids, dihydro-isoalpha acids, tetrahydroisoalpha acids, hexa-hydroisoalpha acids, xanthohumol, isoxanthohumol, 6-prenylnaringen, and 8-prenylnaringenin.

In some aspects, the methods utilize compositions which comprise as a first component a compound or extract derived from the group consisting of acacia, Germacrene A, Germacrene D, red raspberry seed oil, wasabi powder, Davana oil, *Bacopa monniera*, Oleoresin fennel, and *Centella asiatica* and as a second component a compound or extract derived from hops, wherein the ratio of the first component to the second component is from about 0.01:10 to about 10:1. In yet further aspects, the ratio of the first component to the second component provides synergistic activity of adipocyte modification.

In other aspects of this embodiment, the composition further comprises a pharmaceutically acceptable excipient where the pharmaceutically acceptable excipient is selected from the group consisting of coatings, isotonic and absorption delaying agents, binders, adhesives, lubricants, disintegrants, coloring agents, flavoring agents, sweetening agents, absorbants, detergents, and emulsifying agents. In additional aspects, compositions further comprise one or more members selected from the group consisting of antioxidants, vitamins, minerals, proteins, fats, and carbohydrates.

As used herein, "adipocyte modification" means a change in the physical or physiochemical function of the cell from the cell's state prior to treatment. Nonlimiting examples of physical or physiochemical functional changes include altered rates of secretion or amounts of naturally occurring secreted products, the introduction, production and secretion of novel products, the abrogation of secretion of selected compounds, or physical changes in cell morphology and function which may include alterations in membrane permeability or thickness, modification of cell surface receptor numbers or binding efficiency, or the introduction and expression of novel cell surface receptors. The methods of the invention provide for modification of adipocyte physiology in a subject. While modification of adipocyte physiology to enhance lipogenesis or increase adiponectin secretion is desirable in and of itself, it is to be recognized that a modification of adipocyte physiology can have other salutary effects. The present compositions also reduce the inflammatory response and thereby promote healing of, or prevent further damage to, the affected tissue.

As used herein, by "treating" are meant reducing, preventing, and/or reversing the symptoms in the individual to which a compound of the invention has been administered, as compared to the symptoms of an individual not being treated according to the invention. A practitioner will appreciate that the compounds, compositions, and methods described herein are to be used in concomitance with continuous clinical evaluations by a skilled practitioner (physician or veterinarian) to determine subsequent therapy. Such evaluation will aid and inform in evaluating whether to increase, reduce or continue a particular treatment dose, mode of administration, etc.

"Insulin related disorders" refers to those diseases or conditions where the response to insulin is either causative of the disease or has been implicated in the progression or suppression of the disease or condition. Representative examples of insulin related disorders include, without limitation diabetes, diabetic complications, insulin sensitivity, polycystic ovary disease, hyperglycemia, dyslipidemia, insulin resistance, metabolic syndrome, obesity, body weight gain, inflammatory diseases, diseases of the digestive organs, stenocardia, myocardial infarction, sequelae of stenocardia or myocardial infarction, senile dementia, and cerebrovascular dementia. See, *Harrison's Principles of Internal Medicine,* 13th Ed., McGraw Hill Companies Inc., New York (1994). Examples, without limitation, of inflammatory conditions include diseases of the digestive organs (such as ulcerative colitis, Crohn's disease, pancreatitis, gastritis, benign tumor of the digestive organs, digestive polyps, hereditary polyposis syndrome, colon cancer, rectal cancer, stomach cancer and ulcerous diseases of the digestive organs), stenocardia, myocardial infarction, sequelae of stenocardia or myocardial infarction, senile dementia, cerebrovascular dementia, immunological diseases and cancer in general.

As used herein "diabetic complications" include, without limitation, retinopathy, muscle infarction, idiopathic skeletal hyperostosis and bone loss, foot ulcers, neuropathy, arteriosclerosis, respiratory autonomic neuropathy and structural derangement of the thorax and lung parenchyma, left ventricular hypertrophy, cardiovascular morbidity, progressive loss of kidney function, and anemia.

As used herein, the term "hyperlipidemia" refers to a pathognomic condition manifest by elevated serum concentrations of total cholesterol (>200 mg/dL), LDL cholesterol (>130 mg/dL), or triglycerides (>150 mg/dL) or decreased HDL cholesterol (<40 mg/dL). Further, as used herein, the term "fat" refers to serum and adipose triglyceride content and "triglycerides" refers to triacylglyerol esters of fatty acids.

As used herein, the terms "hyperinsulinemia" and "hyperglycemia" refer to a fasting insulin concentration >17 IU/ml) and fasting glucose >125 mg/dL.

As used herein, the term "insulin sensitivity" refers to the ability of a cell, tissue, organ or whole body to absorb glucose in response to insulin. As used in an in vivo context, "insulin sensitivity" refers to the ability of an organism to absorb glucose from the blood stream. An improvement in insulin sensitivity therefore results in an improved ability of the organism to maintain blood glucose levels within a target range. Thus, improved insulin sensitivity may also result in a decreased incidence of hyperglycemia. Improved insulin sensitivity can also treat, prevent or delay the onset of various metabolic conditions, such as diabetes mellitus, syndrome X and diabetic complications. Because of the improved metabolic processing of dietary sugar, improved insulin sensitivity can also treat, prevent or delay the onset of hyperlipidemia and obesity. Additionally, improved insulin sensitivity can lead to treatment, prevention or delayed onset of a variety of inflammatory conditions, such as, for example, diseases of the digestive organs (such as ulcerative colitis, Crohn's disease, pancreatitis, gastritis, benign tumor of the digestive organs, digestive polyps, hereditary polyposis syndrome, colon cancer, rectal cancer, stomach cancer and ulcerous diseases of the digestive organs), stenocardia, myocardial infarction, sequelae of stenocardia or myocardial infarction, senile dementia, cerebrovascular dementia, immunological diseases and cancer in general.

In regard to improvement of insulin sensitivity, then, a subject may be an animal or human who has been diagnosed with insulin resistance or an animal or human, such as an obese or aged animal or human, which is determined to be at risk for insulin resistance. The ordinary clinician will be able to diagnose insulin resistance and, via analysis of a subject's health history, determine whether the subject is at risk for insulin resistance.

The methods of the present invention are intended for use with any subject that may experience the benefits of the methods of the invention. Thus, in accordance with the invention, "subjects" include humans as well as non-human subject, particularly domesticated animals. It will be understood that the subject to which a compound of the invention is administered need not suffer from a specific traumatic state. Indeed, the compounds of the invention may be administered prophylactically, prior to any development of symptoms. The term "therapeutic," "therapeutically," and permutations of these terms are used to encompass therapeutic, palliative as well as prophylactic uses.

As used herein, "improved secretion" means to increase by at least 3%, the rate of secretion or amount of secretion of the referent compound. The invention further provides a method of improving plasma adiponectin concentrations in a subject, comprising administering to the subject an amount of the compound or composition sufficient to increase adiponectin secretion from adipocytes in the subject.

In general, an increase in plasma adiponectin will result in improved insulin sensitivity resulting in improved glucose metabolism, improved blood lipid profiles, and decreased pro-inflammatory adipokine secretion. A decrease in pro-inflammatory adipokine secretion leads to decreased systemic inflammation and disorders associated with inflammation, such as diabetic complications, obesity, inflammatory diseases of the digestive organs, proliferative diseases of the digestive organs, ulcerous diseases of the digestive organs, stenocardia, myocardial infarction, sequelae of stenocardia, sequelae of myocardial infarction, senile dementia, cerebrovascular dementia, immunological diseases and cancer [Guerre-Millo, M. Adipose tissue and adipokines: for better or worse. Diabetes Metabolism 30:13-19, (2004)].

A second embodiment of the invention provides compositions for adipocyte modification for the treatment of insulin related disorders in a subject in need. These compositions comprise a therapeutically effective amount of a pharmaceutically acceptable botanical product, wherein the botanical product is a compound or extract derived from the group consisting of acacia, Germacrene A, Germacrene D, red raspberry seed oil, wasabi powder, Davana oil, *Bacopa monniera*, Oleoresin fennel, and *Centella asiatica.*

In some aspects of this embodiment of the invention, the compositions are useful for adipocyte modification for the improved secretion of adiponectin or, as in other aspects, the modification of adipocyte physiology.

In further aspects of the embodiment, the compositions are used to treat an insulin related disorder selected from the group consisting of diabetes, diabetic complications, insulin sensitivity, hyperglycemia, dyslipidemia, insulin resistance, metabolic syndrome, obesity and body weight gain.

In yet other aspects, the acacia derived botanical product is derived from *Acacia catechu* or *Acacia nilotica*. In those aspects where the acacia derived botanical product is derived from *Acacia catechu* or *Acacia nilotica*, the *Acacia catechu* or *Acacia nilotica* product is selected from the group consisting of gum resin, bark powder, heartwood powder, and an *Acacia catechu* or *Acacia nilotica* extract. In those aspects where the acacia derived botanical product is an *Acacia catechu* or *Acacia nilotica* extract, the extract is selected from acidic, alkaline, polar solvent, nonpolar solvent, and gastric fluid extracts.

In other aspects of this embodiment, compositions further comprise a botanical product derived from hops selected from the group consisting of prenylflavonoids, chalcones, isoalpha acids, reduced isoalpha acids, dihydro-isoalpha acids, tetra-hydroisoalpha acids, hexa-hydroisoalpha acids, xanthohumol, isoxanthohumol, 6-prenylnaringen, and 8-prenylnaringenin. See Verzele, M. and De Keukeleire, D., *Developments in Food Science 27: Chemistry and Analysis of Hop and Beer Bitter Acids*, Elsevier Science Pub. Co., 1991, New York, USA, herein incorporated by reference in its entirety, for a detailed discussion of hops chemistry. As used herein, "Rho" refers to those reduced isoalpha acids wherein the reduction is a reduction of the carbonyl group in the 4-methyl-3-pentenoyl side chain.

In yet other aspects, the composition comprises as a first component a compound or extract derived from the group consisting of acacia, Germacrene A, Germacrene D, red raspberry seed oil, wasabi powder, Davana oil, *Bacopa monniera*, Oleoresin fennel, and *Centella asiatica* and as a second component a compound or extract derived from hops, wherein the ratio of the first component to the second component is from about 0.01:10 to about 10:1. In other aspects, the ratio of the first component to the second component provides synergistic activity of adipocyte modification.

Compositions of this embodiment may further comprises a pharmaceutically acceptable excipient where the pharmaceutically acceptable excipient is selected from the group consisting of coatings, isotonic and absorption delaying agents, binders, adhesives, lubricants, disintergrants, coloring agents, flavoring agents, sweetening agents, absorbants, detergents, and emulsifying agents. Additional compositions may further comprise one or more members selected from the group consisting of antioxidants, vitamins, minerals, proteins, fats, and carbohydrates.

The term "therapeutically effective amount" is used to denote treatments at dosages effective to achieve the therapeutic result sought. Furthermore, one of skill will appreciate that the therapeutically effective amount of the compound of the invention may be lowered or increased by fine tuning and/or by administering more than one compound of the invention, or by administering a compound of the invention with another compound. See, for example, Meiner, C. L., "Clinical Trials: Design, Conduct, and Analysis," Monographs in Epidemiology and Biostatistics, Vol. 8 Oxford University Press, USA (1986). The invention therefore provides a method to tailor the administration/treatment to the particular exigencies specific to a given mammal. As illustrated in the following examples, therapeutically effective amounts may be easily determined, for example, empirically by starting at relatively low amounts and by step-wise increments with concurrent evaluation of beneficial effect.

The term "pharmaceutically acceptable" is used in the sense of being compatible with the other ingredients of the compositions and not deleterious to the recipient thereof.

As used herein, the term "botanical product" is used to denote the complete, unmodified plant or parts thereof, compounds isolated from the plant, or extracts or effusions of the source plant material.

As used herein, "compounds" may be identified either by their chemical structure, chemical name, or common name. When the chemical structure and chemical or common name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated or identified compounds. The compounds described also encompass isotopically labeled compounds where one or more atoms have an atomic mass different from the atomic mass conventionally found in nature. Examples of isotopes that may be incorporated into the compounds of the invention include, but are not limited to, $^{2}H$, $^{3}H$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the invention are congeners, analogs, hydrolysis products, metabolites and precursor or prodrugs of the compound. In general, all physical forms are equivalent for the uses contemplated herein and are intended to be within the scope of the present invention.

Compounds according to the invention may be present as salts. In particular, pharmaceutically acceptable salts of the compounds are contemplated. A "pharmaceutically acceptable salt" of the invention is a combination of a compound of the invention and either an acid or a base that forms a salt (such as, for example, the magnesium salt, denoted herein as "Mg" or "Mag") with the compound and is tolerated by a subject under therapeutic conditions. In general, a pharmaceutically acceptable salt of a compound of the invention will have a therapeutic index (the ratio of the lowest toxic dose to the lowest therapeutically effective dose) of 1 or greater. The person skilled in the art will recognize that the lowest therapeutically effective dose will vary from subject to subject and from indication to indication, and will thus adjust accordingly.

The term "extract" refers to the solid material resulting from (1) exposing a botanical to a solvent, (2) separating the solvent from the plant products, and (3) removing the solvent.

As used herein, the term "solvent" refers to a liquid of aqueous or organic nature possessing the necessary characteristics to extract solid material from the plant material. Examples of solvents in order of decreasing polarity would include, but are not limited to, water, steam, superheated water, glycerin, ethylene glycol, methanol, diethylene glycol, ethanol, acetic acid, 1-propoanol, 1-butanol, acetonitrile, dimethyl sulfoxide, dimethyl formamide, t-butyl alcohol, acetone, 2-butanone, methylene chloride, chloroform, diglyme, dimethoxy ethane, ethyl acetate, tetrahydrofuran, dioxane, methyl t-butyl ether, ether, benzene, toluene, p-xylene, carbon tetrachloride, heptane, hexane, pentane, octanol, cyclohexane, supercritical $CO_2$, liquid $CO_2$, liquid $N_2$ or any combinations of such materials.

As used herein, the term "$CO_2$ extract" refers to the solid material resulting from exposing a plant product to a liquid or supercritical $CO_2$ preparation followed by removal of the $CO_2$.

The term "acacia", as used herein, refers to any member of leguminous trees and shrubs of the genus *Acacia*. Preferably, the botanical product derived from acacia is derived from *Acacia catechu* or *Acacia nilotica*.

As used herein "hop" or "hops" refers to plant cones of the genus *Humulus* which contain a bitter aromatic oil which is used in the brewing industry to prevent bacterial action and add the characteristic bitter taste to beer. More preferably, the hops used are derived from *Humulus lupulus*.

The compounds according to the invention are optionally formulated in a pharmaceutically acceptable vehicle with any of the well known pharmaceutically acceptable carriers, including diluents and excipients (see Remington's Pharmaceutical Sciences, 18th Ed., Gennaro, Mack Publishing Co., Easton, Pa. 1990 and Remington: The Science and Practice of Pharmacy, Lippincott, Williams & Wilkins, 1995). While the type of pharmaceutically acceptable carrier/vehicle employed in generating the compositions of the invention will vary depending upon the mode of administration of the composition to a mammal, generally pharmaceutically acceptable carriers are physiologically inert and non-toxic. Formulations of compositions according to the invention may contain more than one type of compound of the invention), as well any other pharmacologically active ingredient useful for the treatment of the symptom/condition being treated.

The compounds of the present invention may be provided in a pharmaceutically acceptable vehicle using formulation methods known to those of ordinary skill in the art. The compositions of the invention can be administered by standard routes. The compositions of the invention include those suitable for oral, inhalation, rectal, ophthalmic (including intravitreal or intracameral), nasal, topical (including buccal and sublingual), vaginal, or parenteral (including subcutaneous, intramuscular, intravenous, intradermal, and intratracheal). In addition, polymers may be added according to standard methodologies in the art for sustained release of a given compound.

It is contemplated within the scope of the invention that compositions used to treat a disease or condition will use a pharmaceutical grade compound and that the composition will further comprise a pharmaceutically acceptable carrier. It is further contemplated that these compositions of the invention may be prepared in unit dosage forms appropriate to both the route of administration and the disease and patient to be treated. The compositions may conveniently be presented in dosage unit form be prepared by any of the methods well known in the art of pharmacy. All methods include the step of bringing the active ingredient into association with the vehicle which constitutes one or more auxiliary constituents, In general, the compositions are prepared by uniformly and intimately bringing the active ingredient into association with a liquid vehicle or a finely divided solid vehicle or both, and then, if necessary, shaping the product into the desired composition.

The term "dosage unit" is understood to mean a unitary, i.e. a single dose which is capable of being administered to a patient, and which may be readily handled and packed, remaining as a physically and chemically stable unit dose comprising either the active ingredient as such or a mixture of it with solid or liquid pharmaceutical vehicle materials.

Compositions suitable for oral administration may be in the form of discrete units as capsules, sachets, tablets, soft gels or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, gum arabic, dextran, sodium carboxymethylcellulose, gelatin, methylcellulose and polyvinylpyrrolidone. The active ingredient may also be administered in the form of a bolus, electuary or paste.

Transdermal compositions may be in the form of a plaster, microstructured arrays, sometimes called microneedles, iontophoresis (which uses low voltage electrical current to drive charged drugs through the skin), electroporation (which uses short electrical pulses of high voltage to create transient aqueous pores in the skin), sonophoresis (which uses low frequency ultrasonic energy to disrupt the stratum corneum), and thermal energy (which uses heat to make the skin more permeable and to increase the energy of drug molecules), or via polymer patch.

Compositions suitable for ophthalmic administration may be in the form of a sterile aqueous preparation of the active ingredients, which may be in microcrystalline form, for example, in the form of an aqueous microcrystalline suspension. Liposomal compositions or biodegradable polymer systems may also be used to present the active ingredient for ophthalmic administration.

Compositions suitable for topical or ophthalmic administration include liquid or semi-liquid preparations such as liniments, lotions, gels, and oil-in-water or water-in-oil emulsions such as creams, ointments or pastes; or solutions or suspensions such as drops.

In addition to the compositions described above, the compositions of the invention may also be formulated as a depot preparation. Such long-acting compositions may be administered by implantation (e.g. subcutaneously, intraabdominally, or intramuscularly) or by intramuscular injection. Thus, for example, the active ingredient may be formulated with suitable polymeric or hydrophobic materials (for example, as an emulsion in a pharmaceutically acceptable oil), or an ion exchange resin.

For systemic treatment according to the present invention, daily doses of from 0.001-200 mg/kg body weight, preferably from 0.002-20 mg/kg of mammal body weight, for example 0.003-10 mg/kg of a compound or extract are administered, corresponding to a daily dose for an adult human of from 0.2 to 14000 mg of the active ingredient. In the topical treatment of dermatological disorders, ointments, creams or lotions containing from 0.1-750 mg/g, and preferably from 0.1-500 mg/g, of a compound or extract may be administered. For topical use in opthalmological ointments, drops or gels containing from 0.1-750 mg/g, and preferably from 0.1-500 mg/g, of a compound or extract are administered. Oral compositions are formulated, preferably as tablets, capsules, or drops, containing from 0.05-250 mg, preferably from 0.1-1000 mg, of a compound or extract per dosage unit.

The compounds of this invention either alone or in combination with each other or other compounds generally will be administered in a convenient composition. The following representative composition examples are illustrative only and are not intended to limit the scope of the present invention. In the compositions that follow, "active ingredient" means a compound of this invention.

Composition 1: Gelatin Capsules—Hard gelatin capsules are prepared using the following ingredient quantity (mg/capsule) (1) Active ingredient 0.15-1000 (2) Starch, NF 0-650 (3) Starch flowable powder 0-50 (4) Silicone fluid 350 centistokes 0-15.

A tablet composition is prepared using the ingredients below:

Composition 2: Tablets—Ingredient quantity (mg/tablet)—(1) Active ingredient 0.25-500 Cellulose, microcrystalline 200-650 Silicon dioxide, fumed 10-650 Stearate acid 5-15 The components are blended and compressed to form tablets.

Alternatively, tablets each containing 0.25-500 mg of active ingredients are made up as follows:

Composition 3: Tablets Ingredient Quantity (mg/tablet)—(1) Active ingredient 0.25-500, (2) Starch 45 Cellulose, (3) microcrystalline 35 Polyvinylpyrrolidone (as 10% solution in water,) (4) Sodium carboxymethyl cellulose 4.5 (5) Magnesium stearate 0.5 (6) Talc 1 The active ingredients, starch, and cellulose are passed through a No. 45 mesh U.S. sieve and mixed thoroughly. The solution of polyvinylpyrrolidone is mixed with the resultant powders that are then passed through a No. 14 mesh U.S. sieve. The granules so produced are dried at 50-60° C. and passed through a No. 18 mesh U.S. sieve. The sodium carboxymethyl starch, magnesium stearate, and talc, previously passed through a No. 60 U.S. sieve, are then added to the granules that, after mixing, are compressed on a tablet machine to yield tablets.

Suspensions each containing 0.25-500 mg of active ingredient per 5 ml dose are made as follows:

Composition 4: Suspensions Ingredient Quantity (mg/5 ml)—(1) Active ingredient 0.25-500 mg, (2) Sodium carboxymethyl cellulose 50 mg (3) Syrup 1.25 mg Benzoic acid solution 0.10 ml (4) Flavor q.v. Color q.v. (5) Purified Water to 5 ml.

The active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Composition 5: Aerosol Ingredient Quantity (% by weight)—(1) Active ingredient 0.25, (2) ethanol 25.75, (3) Propellant 22 (chlorodifluoromethane) 70.00. The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Composition 6: Suppositories—Ingredient Quantity (mg/suppository)—(1) Active ingredient 250, (2) Saturated fatty acid glycerides 2,000.

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous composition is prepared as follows:

Composition 7: Intravenous Solution—Ingredient Quantity—(1) active ingredient dissolved in ethanol 1% (2) 20 mg Intralipid™ emulsion 1,000 ml.

The solution of the above ingredients is intravenously administered to a patient at a rate of about 1 ml per minute.

The active ingredient above may also be a combination of agents.

An embodiment of the invention provides methods for adipocyte modification for the treatment of insulin related disorders in a subject in need thereof, said method comprising administering to the subject a composition comprising a therapeutically effective amount of a pharmaceutically acceptable botanical product, wherein the botanical product is a compound or extract derived from acacia or hops.

In some aspects of this embodiment the adipocyte modification is the improved secretion of adiponectin while in other aspects the modification is a modification of adipocyte physiology.

In aspects of this embodiment, the insulin related disorder is selected from the group consisting of diabetes, diabetic complications, insulin sensitivity, hyperglycemia, dyslipidemia, insulin resistance, metabolic syndrome, obesity and body weight gain.

In yet other aspects, the acacia derived botanical product is derived from *Acacia catechu* or *Acacia nilotica*. In those aspects where the acacia derived botanical product is derived from *Acacia catechu* or *Acacia nilotica*, the *Acacia catechu* or *Acacia nilotica* product is selected from the group consisting of gum resin, bark powder, heartwood powder, and an *Acacia catechu* or *Acacia nilotica* extract. In those aspects where the acacia derived botanical product is an *Acacia catechu* or *Acacia nilotica* extract, the extract is selected from acidic, alkaline, polar solvent, nonpolar solvent, and gastric fluid extracts.

In some methods of this embodiment, the compositions utilized comprise a botanical product derived from hops which is selected from the group consisting of prenylflavonoids, chalcones, isoalpha acids, reduced isoalpha acids, dihydro-isoalpha acids, tetra-hydroisoalpha acids, hexa-hydroisoalpha acids, xanthohumol, isoxanthohumol, 6-prenylnaringen, and 8-prenylnaringenin.

In yet other methods, the composition employed comprises as a first component a compound or extract derived from acacia and as a second component a compound or extract derived from hops. In other aspects, the ratio of the first component to the second component is from about 0.01:10 to about 10:1. In yet other aspects, the ratio of the first component to the second component provides synergistic activity of adipocyte modification.

In some methods of this embodiment, the composition used further comprises a pharmaceutically acceptable excipient where the pharmaceutically acceptable excipient is selected from the group consisting of coatings, isotonic and absorption delaying agents, binders, adhesives, lubricants, disintergrants, coloring agents, flavoring agents, sweetening agents, absorbants, detergents, and emulsifying agents. In yet other aspects the composition further comprises one or more members selected from the group consisting of antioxidants, vitamins, minerals, proteins, fats, and carbohydrates.

In other methods of this embodiment, the composition used further comprises an extract of bitter melon or aloe vera, or a curcuminoid compound.

Another embodiment of the invention discloses compositions for adipocyte modification for the treatment of insulin related disorders in a subject in need. These compositions comprise a therapeutically effective amount of a pharmaceutically acceptable botanical product, where the botanical product is a compound or extract derived from acacia or hops.

In some aspects, the adipocyte modification is improved secretion of adiponectin or modification of adipocyte physiology.

In other aspects the insulin related disorder is selected from the group consisting of diabetes, diabetic complications, insulin sensitivity, hyperglycemia, dyslipidemia, insulin resistance, metabolic syndrome, obesity and body weight gain.

In some compositions of this embodiment, the acacia derived botanical product is derived from *Acacia catechu* or *Acacia nilotica* where the *Acacia catechu* or *Acacia nilotica* product is selected from the group consisting of gum resin, bark powder, heartwood powder, and an *Acacia catechu* or *Acacia nilotica* extract. In those aspects where the acacia derived botanical product is an *Acacia catechu* or *Acacia nilotica* extract, the *Acacia catechu* or *Acacia nilotica* extract is selected from acidic, alkaline, polar solvent, nonpolar solvent, and gastric fluid extracts.

In the compositions of additional aspects, the botanical product derived from hops is selected from the group consisting of prenylflavonoids, chalcones, isoalpha acids, reduced dihydro-isoalpha acids, tetra-hydroisoalpha acids, hexa-hydroisoalpha acids, xanthohumol, isoxanthohumol, 6-prenylnaringen, and 8-prenylnaringenin.

In yet other aspects the composition comprises as a first component a compound or extract derived from acacia and as a second component a compound or extract derived from hops. In other compositions ratio of the first component to the second component is from about 0.01:10 to about 10:1, while in yet other aspects the ratio of the first component to the second component provides synergistic activity of adipocyte modification.

Compositions of this embodiment may further comprise a pharmaceutically acceptable excipient where the pharmaceutically acceptable excipient is selected from the group consisting of coatings, isotonic and absorption delaying agents, binders, adhesives, lubricants, disintergrants, coloring agents, flavoring agents, sweetening agents, absorbants, detergents, and emulsifying agents. Additional compositions may further comprise one or more members selected from the group consisting of antioxidants, vitamins, minerals, proteins, fats, and carbohydrates.

Other compositions of this embodiment may further comprise an extract of bitter melon or aloe vera, or a curcuminoid compound.

In another embodiment, the invention discloses methods for the treatment of insulin related disorders in a subject in need, such methods comprising administering to the subject a therapeutically effective amount of a pharmaceutically acceptable botanical product and a drug for regulating insulin levels or sensitivity in a subject. In some aspects, the insulin related disorder is selected from the group consisting of diabetes, diabetic complications, insulin sensitivity, hyperglycemia, dyslipidemia, insulin resistance, metabolic syndrome, obesity and body weight gain.

In yet other aspects, the acacia derived botanical product is derived from *Acacia catechu* or *Acacia nilotica*. In those aspects where the acacia derived botanical product is derived from *Acacia catechu* or *Acacia nilotica*, the *Acacia catechu* or *Acacia nilotica* product is selected from the group consisting of gum resin, bark powder, heartwood powder, and an *Acacia catechu* or *Acacia nilotica* extract. In those aspects where the acacia derived botanical product is an *Acacia catechu* or *Acacia nilotica* extract, the extract is selected from acidic, alkaline, polar solvent, nonpolar solvent, and gastric fluid extracts.

In some aspects of this embodiment, the botanical product is derived from hops and is selected from the group consisting of prenylflavonoids, chalcones, isoalpha acids, reduced dihydro-isoalpha acids, tetra-hydroisoalpha acids, hexa-hydroisoalpha acids, xanthohumol, isoxanthohumol, 6-prenylnaringen, and 8-prenylnaringenin.

In methods of this embodiment, the drug for regulating insulin levels is selected from the group consisting of biguanides, sulfonylureas, nonsulfonylureas, α-glucosidase inhibitors, and thiazolidinediones, while in certain aspects the drug for regulating insulin levels is selected from the group consisting of metformin, glipizide, glyburide, glimepiride, rosiglitazone, troglitazone and pioglitazone.

In a preferred aspect, the botanical product is from acacia and the drug for regulating insulin levels is metformin. In another preferred aspect, the botanical product is from acacia and the drug for regulating insulin levels is troglitazone. In yet another preferred aspect, the botanical product is from acacia and the drug for regulating insulin levels is pioglitazone. In another preferred aspect the botanical product is from acacia and the drug for regulating insulin levels is rosiglitazone.

In further preferred aspects the botanical product is reduced isoalpha acids and the drug for regulating insulin levels is metformin, troglitazone, pioglitazone, or rosiglitazone.

In some methods of this embodiment, the botanical product and the drug for regulating insulin levels are given sequentially or simultaneously. In some aspects, the botanical product and the drug for regulating insulin levels are given simultaneously as separate drug forms or as a single composition. In yet other aspects the botanical product and the drug for regulating insulin levels are in a kit.

As used herein, "regulating insulin levels or sensitivity" refers to means for maintaining insulin levels at a particular value or inducing a desired change (either increasing or decreasing) in the level of insulin or in the response to endogenous or exogenous insulin.

As used herein, the terms "sequentially and simultaneously" comprehend the co-administration of the compounds of the invention and the drug for regulating insulin levels within a therapeutically effective time window.

"Co-administration" comprehends administration substantially simultaneously (either less than 0.5 hr. before, less than 0.5 hr. after or together), from about 0.5 to about 24 hr. before the administration of the target agent, or both, i.e., with one or more doses of the botanical product or drug for regulating insulin levels given at least 0.5 hr. before and one dose given substantially simultaneously with (either together with or immediately before of after) the alternate agent. Additionally, "co-administration" comprehends administering more than one dose of the botanical or drug within 24 hrs after a dose of the alternate, in other words, the botanical or drug for regulating insulin levels need not be administered again before or with every administration of the alternate agent, but may be administered intermittently during the course of treatment.

As used herein, "therapeutically effective time window" means the time interval wherein administration of the compounds of the invention to the subject in need thereof reduces or eliminates the deleterious effects or symptoms. In a preferred embodiment, the compound of the invention is administered proximate to the deleterious effects or symptoms.

A further embodiment of the invention provides compositions for the treatment of insulin related disorders in a subject in need, where those compositions comprise a therapeutically effective amount of a pharmaceutically acceptable botanical product and a drug for regulating insulin levels or sensitivity in a subject. In certain aspects of this embodiment the insulin related disorder is selected from the group consisting of diabetes, diabetic complications, insulin sensitivity, hyperglycemia, dyslipidemia, insulin resistance, metabolic syndrome, obesity and body weight gain.

In some aspects the botanical product is a compound or extract derived from acacia or hops. In yet other aspects, the acacia derived botanical product is derived from *Acacia catechu* or *Acacia nilotica*. In those aspects where the acacia derived botanical product is derived from *Acacia catechu* or *Acacia nilotica*, the *Acacia catechu* or *Acacia nilotica* product is selected from the group consisting of gum resin, bark powder, heartwood powder, and an *Acacia catechu* or *Acacia nilotica* extract. In those aspects where the acacia derived botanical product is an *Acacia catechu* or *Acacia nilotica* extract, the extract is selected from acidic, alkaline, polar solvent, nonpolar solvent, and gastric fluid extracts.

In other aspects of this embodiment, the botanical product is derived from hops and is selected from the group consisting of prenylflavonoids, chalcones, isoalpha acids, reduced isoalpha acids, dihydro-isoalpha acids, tetra-hydroisoalpha acids, hexa-hydroisoalpha acids, xanthohumol, isoxanthohumol, 6-prenylnaringen, and 8-prenylnaringenin.

In compositions of yet other aspects the drug for regulating insulin levels is selected from the group consisting of biguanides, sulfonylureas, nonsulfonylureas, a-glucosidase inhibitors, and thiazolidinediones. In other aspects the drug for regulating insulin levels is selected from the group consisting of metformin, glipizide, glyburide, glimepiride, rosiglitazone, troglitazone and pioglitazone.

In a preferred aspect, the botanical product is from acacia and the drug for regulating insulin levels is metformin. In another preferred aspect, the botanical product is from acacia and the drug for regulating insulin levels is troglitazone. In yet another preferred aspect, the botanical product is from acacia and the drug for regulating insulin levels is pioglitazone. In another preferred aspect the botanical product is from acacia and the drug for regulating insulin levels is rosiglitazone.

In further preferred aspects the botanical product is reduced isoalpha acids and the drug for regulating insulin levels is metformin, troglitazone, pioglitazone, or rosiglitazone.

Compositions of this embodiment may further comprise a pharmaceutically acceptable excipient where the pharmaceutically acceptable excipient is selected from the group consisting of coatings, isotonic and absorption delaying agents, binders, adhesives, lubricants, disintergrants, coloring agents, flavoring agents, sweetening agents, absorbants, detergents, and emulsifying agents. Additional compositions may further comprise one or more members selected from the group consisting of antioxidants, vitamins, minerals, proteins, fats, and carbohydrates.

The invention additionally contemplates a kit for use in the treatment of insulin related disorders in a subject in need. The kit comprises a therapeutically effective amount of a pharmaceutically acceptable botanical product and a drug for regulating insulin levels or sensitivity in a subject. In some aspects the components of the kit are used to treat an insulin related disorder where the insulin related disorder is selected from the group consisting of diabetes, diabetic complications, insulin sensitivity, hyperglycemia, dyslipidemia, insulin resistance, metabolic syndrome, obesity and body weight gain. The kit additionally contains instructions as to the use of the components of the kit.

In some aspects of the embodiment, the botanical product of the kit is a compound or extract derived from acacia or hops. In yet other aspects, the acacia derived botanical product is derived from *Acacia catechu* or *Acacia nilotica*. In those aspects where the acacia derived botanical product is derived from *Acacia catechu* or *Acacia nilotica*, the *Acacia catechu* or *Acacia nilotica* product is selected from the group consisting of gum resin, bark powder, heartwood powder, and an *Acacia catechu* or *Acacia nilotica* extract. In those aspects where the acacia derived botanical product is an *Acacia catechu* or *Acacia nilotica* extract, the extract is selected from acidic, alkaline, polar solvent, nonpolar solvent, and gastric fluid extracts.

In some aspects of this embodiment, the botanical product of the kit is derived from hops and is selected from the group consisting of prenylflavonoids, chalcones, reduced isoalpha acids, dihydro-isoalpha acids, tetra-hydroisoalpha acids, hexa-hydroisoalpha acids, xanthohumol, isoxanthohumol, 6-prenylnaringen, and 8-prenylnaringenin.

In other aspects the drug for regulating insulin levels in the kit is selected from the group consisting of biguanides, sulfonylureas, nonsulfonylureas, a-glucosidase inhibitors, and thiazolidinediones. In other aspects the drug for regulating insulin levels is selected from the group consisting of metformin, glipizide, glyburide, glimepiride, rosiglitazone, troglitazone and pioglitazone.

In a preferred aspect, the botanical product of the kit is from acacia and the drug for regulating insulin levels is metformin. In another preferred aspect, the botanical product is from acacia and the drug for regulating insulin levels is troglitazone. In yet another preferred aspect, the botanical product is from acacia and the drug for regulating insulin levels is pioglitazone. In another preferred aspect the botanical product is from acacia and the drug for regulating insulin levels is rosiglitazone.

In further preferred aspects the botanical product of the kit is reduced isoalpha acids and the drug for regulating insulin levels is metformin, troglitazone, pioglitazone, or rosiglitazone.

Compositions used in the kit may further comprise a pharmaceutically acceptable excipient where the pharmaceutically acceptable excipient is selected from the group consisting of coatings, isotonic and absorption delaying agents, binders, adhesives, lubricants, disintergrants, coloring agents, flavoring agents, sweetening agents, absorbants, detergents, and emulsifying agents. Additional compositions may further comprise one or more members selected from the group consisting of antioxidants, vitamins, minerals, proteins, fats, and carbohydrates.

In some aspects, the botanical product of the kit and the drug for regulating insulin levels are given sequentially or simultaneously. In some aspects, the botanical product and the drug for regulating insulin levels are given simultaneously as separate drug forms or as a single composition.

As used herein, the term "CLA isomers" refers to fatty acids (or alcohols) with the same 18-carbon, polyunsaturated structure. In the case of CLA, each isomer is derived from the 18-carbon essential polyunsaturated fat linoleic acid (18:2n–6), which has two cis-double bonds at carbons 9 and 12. CLA isomers also have two double bonds, but they are adjacent to one another, or conjugated, on carbons 7 to 13, and can be cis or trans.

The term "conjugated compound" refers to a compound having at least a portion that is a hydrocarbon, with at least three consecutive carbon-carbon bonds, such that single and double carbon-carbon bonds are found in an alternating manner. Thus, the compound will include the subunit —HC=CH—H$_2$C=CH—. Two preferred categories of conjugated compounds are fatty acids and fatty alcohols. It should be noted that these di- or poly-unsaturated compounds are referred to herein using the common names of the corresponding naturally occurring compounds having the same number of carbons and unsaturations. Although such naturally occurring compounds are not necessarily conjugated, due to the arrangement of their carbon-carbon double bonds, it will be understood in the context of the present invention that only conjugated versions of those compounds are contemplated; i.e., the arrangement of the double bounds will be such that they contain the substructure —C=C—C=C. While compounds having as few as 4, 5, 6, or 7 carbon atoms are contemplated, the preferred conjugated compounds have 8, 9, 10, 12, 14, 16 or more carbon atoms, preferably not more than 32, 30, 28, or 26 carbon atoms.

It should be noted that the phrase "conjugated fatty acid" or "conjugated fatty alcohol", as used herein, also includes isomers of fatty acids and fatty alcohols, as well as any other polyunsaturated compounds. Suitable conjugated fatty acids include, without limitation, conjugated versions of linoleic acid, linolenic acid, gamma linolenic acid, arachidonic acid, mead acid, stearidonic acid, alpha-eleostearic acid, eleostearic acid, pinolenic acid, docosatetraenoic acid, 9,12-octadecadienoic acid, octadecatrienoic acid, eicosatetraenoic acid, eicosapentaenoic acid, docosahexaenoic acid, docosapentaenoic acid, and all other diunsaturated and polyunsaturated fatty acids. In a preferred embodiment, the conjugated fatty acid is CLA in the triglyceride form.

As used herein, the phrase "conjugated fatty alcohols" includes, without limitation, conjugated versions of linoleic alcohol, linolenic alcohol, gamma linolenic alcohol, arachidonic alcohol, mead alcohol, stearidonic alcohol alpha-eleostearic alcohol, eleostearic alcohol, pinolenic alcohol, docosadienic alcohol, docosatetraenoic alcohol, octadecadienoic alcohol, octadecatrienoic alcohol, eicosatetraenoic alcohol, eicosapentaenoic alcohol, docosahexaenoic alcohol, docosapentaenoic alcohol, and all other diunsaturated and polyunsaturated fatty alcohols. Note that the present invention includes alcohols and acids in which one or more of the double bonds result in a cis isomer, as well as those in which one or more of the double bonds result in a trans isomer. In some cases, all the double bonds are cis, while in they are all trans, and in still other cases, they are mixed cis and trans compounds.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

EXAMPLES

Example 1

Screening of Hops Derivatives, Select Phytochemicals and Phytoextracts for Anti-Inflammatory Activity in the LPS-Stimulated Murine Macrophage Model The Model—The murine macrophage cell line RAW 264.7 is a well-established model for assessing anti-inflammatory activity of test agents. Stimulation of RAW 264.7 cells with bacterial lipopolysaccharide induces the expression of COX-2 and production of $PGE_2$. Inhibition of $PGE_2$ synthesis is used as a metric for anti-inflammatory activity of the test agent.

Equipment—Equipment used in this example included an OHAS Model #E01140 analytical balance, a Form a Model #F1214 biosafety cabinet (Marietta, Ohio), various pipettes to deliver 0.1 to 100 µl (VWR, Rochester, N.Y.), a cell hand tally counter (VWR Catalog #23609-102, Rochester, N.Y.), a Form a Model #F3210 $CO_2$ incubator (Marietta, Ohio), a hemocytometer (Hausser Model #1492, Horsham, Pa.), a Leica Model #DM IL inverted microscope (Wetzlar, Germany), a PURELAB Plus Water Polishing System (U.S. Filter, Lowell, Mass.), a 4° C. refrigerator (Form a Model #F3775, Marietta, Ohio), a vortex mixer (VWR Catalog #33994-306, Rochester, N.Y.), and a 37° C. water bath (Shel Lab Model #1203, Cornelius, Oreg.).

Chemicals and Reagents—Bacterial lipopolysaccharide (LPS; B *E. coli* 055:B5) was from Sigma (St. Louis, Mo.). Heat inactivated Fetal Bovine Serum (FBS-HI Cat. #35-011CV), and Dulbeco's Modification of Eagle's Medium (DMEM Cat #10-013CV) was purchased from Mediatech (Herndon, Va.). Hops fractions (1) alpha hop (1% alpha acids; AA), (2) aromahop OE (10% beta acids and 2% isomerized alpha acids, (3) isohop (isomerized alpha acids; IAA), (4) beta acid solution (beta acids BA), (5) hexahop gold (hexahydro isomerized alpha acids; HHIAA), (6) redihop (reduced isomerized-alpha acids; RIAA), (7) tetrahop (tetrahydro-iso-alpha acids THIAA) and (8) spent hops were obtained from Betatech Hops Products (Washington, D.C., U.S.A.). The spent hops were extracted two times with equal volumes of absolute ethanol. The ethanol was removed by heating at 40° C. until a only thick brown residue remained. This residue was dissolved in DMSO for testing in RAW 264.7 cells. A complete description of the hops derivatives is presented in Table 1.

TABLE 1

| Description of hops test materials. | |
|---|---|
| Hops Test Material | Description |
| Alpha acid solution | 82% alpha acids/2.7% beta acids/2.95% isoalpha acids by volume. Alpha acids include humulone, adhumulone, and cohumulone. |
| Rho isoalpha acids (RIAA) | Rho-isohumulone, rho-isoadhumulone, and rho-isocohumulone. |
| Isoalpha acids (IAA) | 25.3% isoalpha acids by volume. Includes cis & trans isohumulone, cis & trans isoadhumulone, and cis & trans isocohumulone. |
| Tetrahydroisoalpha acids (THIAA) | Complex hops - 8.9% THIAA by volume. Includes cis & trans tetrahydro-isohumulone, cis & trans tetrahydro-isoadhumulone and cis & trans tetrahydro-isocohumulone |
| Hexahydroisoalpha acids (HHIAA) | 3.9% THIAA; 4.4% HHIAA by volume. The HHIAA isomers include hexahydro-isohumulone, hexahydro-isoadhumulone and hexahydro-isocohumulone. |

TABLE 1-continued

Description of hops test materials.

| Hops Test Material | Description |
| --- | --- |
| Beta acid solution | 10% beta acids by volume; <2% alpha acids. The beta acids include lupulone, colupulone, adlupulone and prelupulone. |
| Spent hops $CO_2$/Ethanol | Xanthohumol, xanthohumol A, xanthohumol B, xanthohumol C, xanthohumol D, xanthohumol E, xanthohumol G, xanthohumol H, trans-hydroxyxanthohumol, 1",2"-dihydroxyxanthohumol C, desmethylxanthohumol B, desmethylxanthohumol J, xanthohumol I, desmethylxanthohumol, isoxanthohumol, ab dihydroxanthohumol, diprenylxanthohumol, 5"-hydroxyxanthohumol, 5'-prenylxanthohumol, 6,8-diprenylnaringenin, 8-preylnaringenin, 6-prenylnaringen, isoxanthohumol, humulinone, cohumulinone, 4-hydroxybenzaldehyde, and sitosterol-3-O-b-glucopyranoside. |
| Aromahop oil | 25-30% Oil, ~10% beta acids, <.2% Isohop |

Quercetin, oleanolic acid, galangin, genistein, apigenin, luteolin, keampferol, resveratrol, morin, myricetin, naringenin, catechin, fisetin, and rutin were obtained from Sigma (St. Louis, Mo.). Ginger, *Acacia* sample #4909 extract, rosemary, cayenne pepper, curcumin, ipriflavone, lemon bioflavonoid, and sesamin were commercial samples provided by Metagenics (Gig Harbor, Wash.). Berberine was purchased from Garden State Nutritionals (West Caldwell, N.J.). Unless otherwise noted, all standard reagents were obtained from Sigma (St. Louis, Mo.).

Cell culture—RAW 264.7 cells, obtained from American Type Culture Collection (Catalog #TIB-71, Manassas, Va.), were grown in Dulbecco's Modification of Eagle's Medium (DMEM, Mediatech, Herndon, Va.) and maintained in log phase. The DMEM growth medium was made by adding 50 ml of heat inactivated FBS and 5 ml of penicillin/streptomycin to a 500 ml bottle of DMEM and storing at 4° C. The growth medium was warmed to 37° C. in water bath before use.

On day one of the experiment, the log phase RAW 264.7 cells were plated in 0.2 ml growth medium at $8 \times 10^4$ cells per well in a 96-well tissue culture. At the end of the day one (6 to 8 h post plating), 100 µl of growth medium from each well was removed and replaced with 100 µl fresh medium.

A 1.0 mg/ml stock solution of LPS, used to induce the expression of COX-2 in the RAW 264.7 cells, was prepared by dissolving 1.0 mg of LPS in 1 ml DMSO. It was vortexed until dissolved and stored at 4° C. Before use, it was melted at room temperature or in a 37° C. water bath.

On day two of the experiment, test materials were prepared as 1000× stock in DMSO. In 1.7 ml microfuge tubes, 1 ml DMEM without FBS was added for test concentrations of 0.05, 0.10, 0.5, and 1.0 µg/ml or 1.5, 3.0, 6.0 and 12 µg/ml. Two µl of the 1000×DMSO stock of the test material was added to the 1 ml of medium without FBS. The tube contained the final concentration of the test material concentrated 2-fold and the tube placed in an incubator for 10 minutes to equilibrate to 37° C.

For COX-2 associated $PGE_2$ synthesis, 100 µl of medium were removed from each well of the cell plates prepared on day one and replaced with 100 µl of equilibrated 2× final concentration of the test compounds. Cells were then incubated for 90 minutes. Twenty µl of LPS were added to each well of cells to be stimulated to achieve a final concentration of 1 µg LPS/ml and the cells were incubated for 18 hours. Before sampling the media for $PGE_2$ quantification, the appearance of the cells was observed and viability was assessed visually. No apparent toxicity was observed at the highest concentrations tested for any of the compounds.

Twenty-five µl of supernatant medium from each well was then transferred to a clean microfuge tube for the determination of $PGE_2$ released into the medium.

$PGE_2$ assay—A commercial, non-radioactive procedure for quantification of $PGE_2$ was employed (Caymen Chemical, Ann Arbor, Mich.) and the recommended procedure of the manufacturer was used without modification. Briefly, 25 µl of the medium, along with a serial dilution of $PGE_2$ standard samples, were mixed with appropriate amounts of acetylcholinesterase-labeled tracer and $PGE_2$ antiserum, and incubated at room temperature for 18 h. After the wells were emptied and rinsed with wash buffer, 200 PI of Ellman's reagent containing substrate for acetycholinesterase were added. The reaction was maintained on a slow shaker at room temperature for 1 h and the absorbance at 415 nm was determined in a Bio-Tek Instruments (Model #Elx800, Winooski, Vt.) ELISA plate reader. The $PGE_2$ concentration was represented as picograms per ml. The manufacturer's specifications for this assay include an intra-assay coefficient of variation of <10%, cross reactivity with $PGD_2$ and $PGF_2$ of less than 1% and linearity over the range of 10-1000 pg $ml^{-1}$.

Calculations—The median inhibitory concentrations ($IC_{50}$) for $PGE_2$ synthesis were calculated using CalcuSyn (BIOSOFT, Ferguson, Mo.). A minimum of four concentrations of each test material or positive control was used for computation. This statistical package performs multiple drug dose-effect calculations using the Median Effect methods described by T. C Chou and P. Talalay [Chou, T. C. and P. Talalay. Quantitative analysis of dose-effect relationships; the combined effects of multiple drugs or enzyme inhibitors. Adv Enzyme Regul 22: 27-55, (1984)] and is incorporated herein by reference. Experiments were repeated three times on three different dates. The percent inhibition at each dose was averaged over the three independent experiments and used to calculate the median inhibitory concentrations reported.

Median inhibitory concentrations were ranked into four arbitrary categories: (1) highest anti-inflammatory response for those agents with an $IC_{50}$ values within 0.3 µg/ml of 0.1; (2) high anti-inflammatory response for those agents with an $IC_{50}$ value within 0.7 µg/ml of 1.0; (3) intermediate anti-inflammatory response for those agents with $IC_{50}$ values between 2 and 7 µg/ml; and (4) low anti-inflammatory response for those agents with $IC_{50}$ values greater than 12 µg/ml, the highest concentration tested.

Results—Overall, hops derivatives were the most potent natural, anti-inflammatory agents (Table 2). Median inhibitory concentrations ($IC_{50}$) for hops derivatives ranged from 0.08 µg/ml for Rho isoalpha acids to 1.6 µg/ml for aroma hop. Only hops derivatives received the ranking of highest relative anti-inflammatory potency; these included Rho isoalpha acids, isoalpha acids, tetrahydroisoalpha acids, $CO_2$ hop extract, alpha acids, and hexahydroisoalpha acids. Those agents ranked as exhibiting high anti-inflammatory activity included hops beta-acids, quercetin, spent hops $CO_2$/ethanol extract, ginger, *Acacia* sample #4909 extract, oleanolic acid, rosemary, galangin, hops aromahop oil, and genistein. Intermediate anti-inflammatory activity was exhibited by cayenne pepper, apigenin, curcumin, berberine, luteolin, keampferol, resveratrol, and ipriflavone. All other test materials were ranked as having low anti-inflammatory activity with $IC_{50}$ values exceeding 12 µg/ml.

TABLE 2

Relative potency of hops derivatives, phytochemicals and phytoextracts based upon median inhibitory concentrations of $PGE_2$ inhibition

| Test Material | $IC_{50}$ [µg/ml] | Relative $IC_{50}$† | Relative Potency† |
|---|---|---|---|
| Hops: Rho Isoalpha acids | 0.08 | 0.1 | Highest |
| Hops: Isoalpha acids | 0.13 | 0.1 | Highest |
| Hops: Tetrahydro isoalpha acids | 0.20 | 0.1 | Highest |
| Hops: $CO_2$ hop extract | 0.22 | 0.1 | Highest |
| Hops: Alpha acids | 0.22 | 0.1 | Highest |
| Hops: Hexahydro isoalpha acids | 0.29 | 0.1 | Highest |
| Hops: Beta acids | 0.54 | 1.0 | High |
| Quercetin | 0.82 | 1.0 | High |
| Hops: Spent hops $CO_2$/Ethanol | 0.88 | 1.0 | High |
| Ginger | 0.98 | 1.0 | High |
| *Acacia* sample #4909 extract | 1.0 | 1.0 | High |
| Oleanolic acid | 1.2 | 1.0 | High |
| Rosemary | 1.3 | 1.0 | High |
| Galangin | 1.4 | 1.0 | High |
| Hops: Aromahop oil | 1.6 | 1.0 | High |
| Genistein | 1.7 | 1.0 | High |
| Cayenne pepper | 2.6 | 2.0-6.0 | Intermediate |
| Apigenin | 2.8 | 2.0-6.0 | Intermediate |
| Curcumin | 2.8 | 2.0-6.0 | Intermediate |
| Berberine | 3.3 | 2.0-6.0 | Intermediate |
| Luteolin | 3.9 | 2.0-6.0 | Intermediate |
| Keampferol | 4.3 | 2.0-6.0 | Intermediate |
| Resveratrol | 5.8 | 2.0-6.0 | Intermediate |
| Ipriflavone | 6.3 | 2.0-6.0 | Intermediate |
| Lemon bioflavonoid | >12 | >12 | Low |
| Morin | >12 | >12 | Low |
| Myricetin | >12 | >12 | Low |
| Naringenin | >12 | >12 | Low |
| Catechin | >12 | >12 | Low |
| Fisetin | >12 | >12 | Low |
| Rutin | >12 | >12 | Low |
| Sesamin | >12 | >12 | Low |

†Results were assigned to four arbitrary categories of anti-inflammatory activity based upon median inhibitory concentration: (1) highest anti-inflammatory response for those agents with an $IC_{50}$ values within 0.3 µg/ml of 0.1; (2) high anti-inflammatory response for those agents with an $IC_{50}$ value within 0.7 µg/ml of 1.0; (3) intermediate anti-inflammatory response for those agents with $IC_{50}$ values between 2 and 7 µg/ml; and (4) low anti-inflammatory response for those agents with $IC_{50}$ values greater than 12 µg/ml, the highest concentration tested.

Example 2

Inhibition of $PGE_2$ Synthesis in Stimulated and Nonstimmulated Murine Macrophages by Hops Compounds and Derivatives The objective of this example was to assess the extent to which hops derivatives inhibited COX-2 synthesis of $PGE_2$ preferentially over COX-1 synthesis of $PGE_2$ in the murine macrophage model. The RAW 264.7 cell line as described in Example 1 was also used in this example. Equipment, Chemicals and Reagents, $PGE_2$ assay, and calculations were as described in Example 1.

Test materials—Hops derivatives as described in Table 1 were used. The COX-1 selective aspirin and COX-2 selective celecoxib were used as positive controls. Aspirin was obtained from Sigma (St. Louis, Mo.) and the commercial formulation of celecoxib was used (Celebrex™, Searle & Co., Chicago, Ill.).

Cell culture and treatment with test material—RAW 264.7 cells (TIB-71) were obtained from the American Type Culture Collection (Manassas, Va.) and sub-cultured as described in Example 1. For COX-2 associated $PGE_2$ synthesis, 100 µl of medium was removed from each well of the cell plates prepared on day one and replaced with 100 µl of equilibrated 2× final concentration of the test compounds. Cells were then incubated for 90 minutes. Twenty µl of LPS were added to each well of cells to be stimulated to achieve a final concentration of 1 µg LPS/ml and the cells were incubated for 4 h. The cells were further incubated with 5 µM arachadonic acid for 15 minutes. Twenty-five µl of supernatant medium from each well was transferred to a clean microfuge tube for the determination of $PGE_2$ released into the medium.

For COX-1 associated $PGE_2$ synthesis, 100 µl of medium were removed from each well of the cell plates prepared on day one and replaced with 100 µl of equilibrated 2× final concentration of the test compounds. Cells were then incubated for 90 minutes. Next, instead of LPS stimulation, the cells were incubated with 100 µM arachadonic acid for 15 minutes. Twenty-five µl of supernatant medium from each well was transferred to a clean microfuge tube for the determination of $PGE_2$ released into the medium.

The appearance of the cells was observed and viability was determined as described in Example 1. No apparent toxicity was observed at the highest concentrations tested for any of the compounds. Twenty-five µl of supernatant medium from each well was transferred to a clean microfuge tube for the determination of $PGE_2$ released into the medium. $PGE_2$ was determined and reported as previously described in Example 1. The median inhibitory concentrations ($IC_{50}$) for $PGE_2$ synthesis from both COX-2 and COX-1 were calculated as described in Example 1.

Results—The aspirin and celecoxib positive controls demonstrated their respective cyclooxygenase selectivity in this model system (Table 3). While aspirin was approximately 1000-fold more selective for COX-1, celecoxib was 114 times more selective for COX-2. All hops materials were COX-2 selective with Rho isoalpha acids and isoalpha acids demonstrating the highest COX-2 selectivity, 363- and 138-fold respectively. Such high COX-2 selectivity combined with low median inhibitory concentrations, has not been previously reported for natural products from other sources. Of the remaining hops derivatives, only the aromahop oil exhibited a marginal COX-2 selectivity of 3-fold. For extrapolating in vitro data to clinical efficacy, it is generally assumed that a COX-2 selectivity of 5-fold or greater indicates the potential for clinically significant protection of gastric mucosa. Under this criterion, beta acids, $CO_2$ hop extract, spent hops $CO_2$/ethanol, tetrahydro isoalpha acids and hexahydro isoalpha acids displayed potentially clinically relevant COX-2 selectivity.

TABLE 3

COX-2 and COX-1 inhibition in RAW 264.7 cells by hop fractions and derivatives

| Test Material | $IC_{50}$ COX-2 [µg/ml] | $IC_{50}$ COX-1 [µg/ml] | COX-1/COX-2 |
|---|---|---|---|
| Rho Isoalpha acids | 0.08 | 29 | 363 |
| Isoalpha acids | 0.13 | 18 | 138 |
| Beta acids | 0.54 | 29 | 54 |

TABLE 3-continued

COX-2 and COX-1 inhibition in RAW 264.7 cells by hop fractions and derivatives

| Test Material | $IC_{50}$ COX-2 [μg/ml] | $IC_{50}$ COX-1 [μg/ml] | COX-1/COX-2 |
|---|---|---|---|
| $CO_2$ hop extract | 0.22 | 6.3 | 29 |
| Alpha acids | 0.26 | 6.2 | 24 |
| Spent hops $CO_2$/Ethanol | 0.88 | 21 | 24 |
| Tetrahydro isoalpha acids | 0.20 | 4.0 | 20 |
| Hexahydro isoalpha acids | 0.29 | 3.0 | 10 |
| Aromahop Oil | 1.6 | 4.1 | 3.0 |
| Positive Controls | | | |
| Aspirin | 1.16 | 0.0009 | 0.0008 |
| Celecoxib | 0.005 | 0.57 | 114 |

Example 3

Lack of Direct $PGE_2$ Inhibition by Reduced Isomerized Alpha Acids or Isomerized Alpha Acids in LPS-Stimulated Raw 264.7 Cells The objective of this study was to assess the ability of the hops derivatives Rho isoalpha acids and isomerized alpha acids to function independently as direct inhibitors of COX-2 mediated $PGE_2$ biosynthesis in the RAW 264.7 cell model of inflammation. The RAW 264.7 cell line as described in Example 1 was used in this example. Equipment, Chemicals and Reagents, $PGE_2$ assay, and calculations were as described in Example 1.

Test materials—Hops derivatives Rho isoalpha acids and isomerized alpha acids, as described in Table 1, were used. Aspirin, a COX-1 selective positive control, was obtained from Sigma (St. Louis, Mo.).

Cell culture and treatment with test material—RAW 264.7 cells (TIB-71) were obtained from the American Type Culture Collection (Manassas, Va.) and sub-cultured as described in Example 1. Following overnight incubation at 37° C. with 5% $CO_2$, the growth medium was aspirated and replaced with 200 μl DMEM without FBS or penicillin/streptomycin. RAW 264.7 cells were stimulated with LPS and incubated overnight to induce COX-2 expression. Eighteen hours post LPS-stimulation, test materials were added followed 60 minutes later by the addition of the calcium ionophore A23187. Test materials were dissolved in DMSO as a 250-fold stock solution. Four μl of this 250-fold stock test material preparation was added to 1 ml of DMEM and 200 μl of this solution was subsequently added to eight wells for each dose of test material. Supernatant media was sampled for $PGE_2$ determination after 30 minutes. Median inhibitory concentrations were computed from a minimum of four concentrations over two independent experiments as described in Example 1.

Determination of $PGE_2$—A commercial, non-radioactive procedure for quantification of $PGE_2$ was employed (Caymen Chemical, Ann Arbor, Mich.) for the determination of $PGE_2$ and the recommended procedure of the manufacturer was used without modification as described in Example 1.

Cell viability—Cell viability was assessed by microscopic inspection of cells prior to or immediately following sampling of the medium for $PGE_2$ assay. No apparent cell mortality was noted at any of the concentrations tested.

Calculations—Four concentrations 0.10, 1.0, 10 and 100 μg/ml were used to derive dose-response curves and compute medium inhibitory concentrations ($IC_{50s}$) with 95% confidence intervals using CalcuSyn (BIOSOFT, Ferguson, Mo.).

Results—LPS-stimulation of $PGE_2$ production in RAW 264.7 cells ranged from 1.4-fold to 2.1-fold relative to non-stimulated cells. The $IC_{50}$ value of 8.7 μg/ml (95% CL=3.9-19) computed for the aspirin positive control was consistent with published values for direct COX-2 inhibition ranging from 1.4 to 50 μg/ml [Warner, T. D. et al. Nonsteroidal drug selectivities for cyclo-oxygenase-1 rather than cyclo-oxygenase-2 are associated with human gastrointestinal toxicity: A full in vitro analysis. *Proc. Natl. Acad. Sci. USA* 96:7563-7568, (1999)] and historical data of this laboratory of 3.2 μg/ml (95% CL=0.55-19) in the A549 cell line.

When added following COX-2 induction in RAW 264.7 cells by LPS, both RIAA and IAA produced only modest, dose-related inhibition of $PGE_2$. Over the 1000-fold increase in concentration of test material, only a 14 and 10 percent increase in inhibition was noted, respectively, for RIAA and IAA. The shallowness of the dose-response slopes resulted in $IC_{50}$ values (Table 4) in the mg/ml range for RIAA (36 mg/ml) and IAA (>1000 mg/ml). The minimal changes observed in response over three-log units of doses suggests that the observed $PGE_2$ inhibitory effect of the hops derivatives in this cell-based assay may be a secondary effect on the cells and not a direct inhibition of COX-2 enzyme activity.

Figure 4:
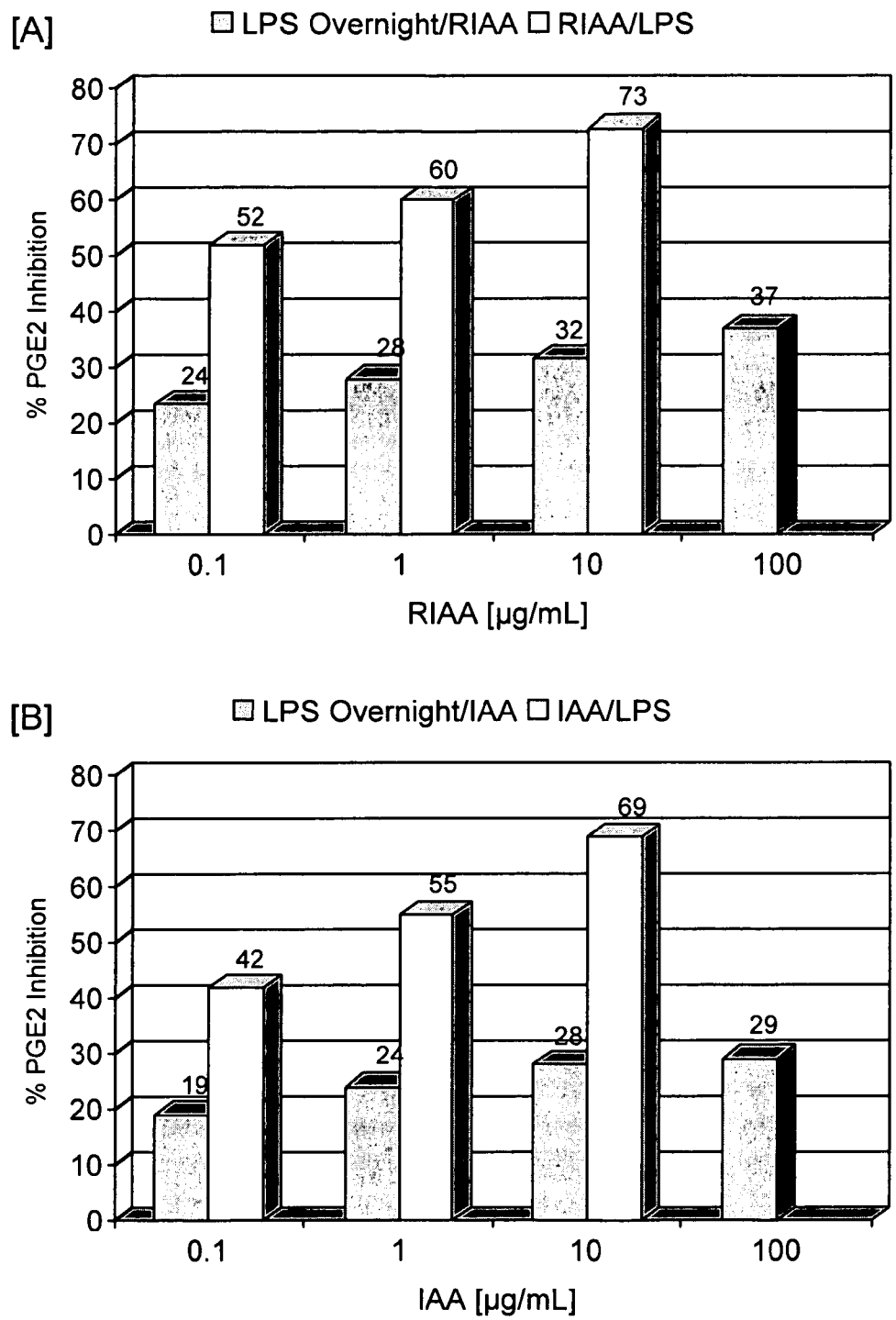
FIG. 4 depicts RIAA [panel A] and IAA [panel B] dose-related inhibition of $PGE_2$ biosynthesis when added before LPS stimulation of COX-2 expression (white bars) or following overnight LPS-stimulation prior to the addition of test material (grey bars).

FIGS. 4A and 4B depict the dose-response data from Example 1, respectively, for RIAA and IAA as white bars and the dose-response data from this example as gray bars. The effect of sequence of addition is clearly seen and supports the inference that RIAA and IAA are not direct COX-2 enzyme inhibitors.

From Examples 1-3, it appears that (1) Hop materials were among the most active, anti-inflammatory natural products tested as assessed by their ability to inhibit $PGE_2$ biosynthesis in vitro; (2) RIAA and IAA do not appear to be direct COX-2 enzyme inhibitors based on their pattern of inhibition with respect to COX-2 induction; and (3) RIAA and IAA have a COX-2 selectively that appears to be based on inhibition of COX-2 expression, not COX-2 enzyme inhibition. This selectivity differs from celecoxib, whose selectivity is based on differential enzyme inhibition.

TABLE 4

Median inhibitory concentrations for RIAA, IAA in RAW 264.7 cells when test material is added post overnight LPS-stimulation.

| Test Material | $IC_{50}$ [μg/ml] | 95% Confidence Interval [μg/ml] |
|---|---|---|
| RIAA | 36,000 | 17,000-79,000 |
| IAA | >1,000,000 | — |
| Positive Control | | |
| Aspirin | 8.7 μg/ml | 3.9-19 |

RAW 264.7 cells were stimulated with LPS and incubated overnight to induce COX-2 expression. Eighteen hours post LPS-stimulation, test material was added followed 60 minutes later by the addition of A23187. Supernatant media was sampled for $PGE_2$ determination after 30 minutes. Median inhibitory concentrations were computed from a minimum of eight replicates at four concentrations over two independent experiments.

Example 4

Hops Compounds and Derivatives are not Direct Cyclooxygenase Enzyme Inhibitors in A549 Pulmonary Epithelial Cells Chemicals—Hops and hops derivatives used in this example were previously described in Example 1. All other chemicals were obtained from suppliers as described in Examples 1 and 2.

Equipment, PGE$_2$ assay, and Calculations were as described in Example 1.

Cells—A549 (human pulmonary epithelial) cells were obtained from the American Type Culture Collection (Manassas, Va.) and sub-cultured according to the instructions of the supplier. The cells were routinely cultured at 37° C. with 5% CO$_2$ in RPMI 1640 containing 10% FBS, with 50 units penicillin/ml, 50 µg streptomycin/ml, 5 mM sodium pyruvate, and 5 mM L-glutamine. On the day of the experiments, exponentially growing cells were harvested and washed with serum-free RPMI 1640.

Log phase A549 cells were plated at 8×10$^4$ cells per well in 0.2 ml growth medium per well in a 96-well tissue culture plate. For the determination of PGE$_2$ inhibition by the test compounds, the procedure of Warner, et al. [Nonsteroid drug selectivities for cyclo-oxygenase-1 rather than cyclo-oxygenase-2 are associated with human gastrointestinal toxicity: a full in vitro analysis. Proc Natl Acad Sci USA 96, 7563-7568, (1999)], also known as the WHMA-COX-2 protocol was followed with no modification. Briefly, 24 hours after plating of the A549 cells, interleukin-1β (10 ng/ml) was added to induce the expression of COX-2. After 24 hr, the cells were washed with serum-free RPMI 1640. Subsequently, the test materials, dissolved in DMSO and serum-free RPMI, were added to the wells to achieve final concentrations of 25, 5.0, 0.5 and 0.05 µg/ml. Each concentration was run in duplicate. DMSO was added to the control wells in an equal volume to that contained in the test wells. Sixty minutes later, A23187 (50 µM) was added to the wells to release arachadonic acid. Twenty-five µl of media were sampled from the wells 30 minutes later for PGE$_2$ determination.

Cell viability was assessed visually and no apparent toxicity was observed at the highest concentrations tested for any of the compounds. PGE$_2$ in the supernatant medium was determined and reported as previously described in Example 1. The median inhibitory concentration (IC$_{50}$) for PGE$_2$ synthesis was calculated as previously described in Example 1.

Results—At the doses tested, the experimental protocol failed to capture a median effective concentration for any of the hops extracts or derivatives. Since the protocol requires the stimulation of COX-2 expression prior to the addition of the test compounds, it is believed that the failure of the test materials to inhibit PGE$_2$ synthesis is that their mechanism of action is to inhibit the expression of the COX-2 isozyme and not activity directly. While some direct inhibition was observed using the WHMA-COX-2 protocol, this procedure appears inappropriate in evaluating the anti-inflammatory properties of hops compounds or derivatives of hops compounds.

Example 5

Hops Derivatives Inhibit Mite Dust Allergen Activation of PGE$_2$ Biosynthesis in A549 Pulmonary Epithelial Cells Chemicals—Hops and hops derivatives, (1) alpha hop (1% alpha acids; AA), (2) aromahop OE (10% beta acids and 2% isomerized alpha acids, (3) isohop (isomerized alpha acids; IAA), (4) beta acid solution (beta acids BA), (5) hexahop gold (hexahydro isomerized alpha acids; HHIAA), (6) redihop (reduced isomerized-alpha acids; RIAA), and (7) tetrahop (tetrahydro-iso-alpha acids THIAA), used in this example were previously described in Example 1. All other chemicals were obtained from suppliers as described in Examples 1 and 2. Test materials at a final concentration of 10 µg/ml were added 60 minutes prior to the addition of the mite dust allergen.

Equipment, PGE$_2$ assay, and Calculations were as described in Example 1.

Mite dust allergen isolation—*Dermatophagoides farinae* are the American house dust mite. *D. farinae* were raised on a 1:1 ratio of Purina Laboratory Chow (Ralston Purina, Co, St. Louis, Mo.) and Fleischmann's granulated dry yeast (Standard Brands, Inc. New York, N.Y.) at room temperature and 75% humidity. Live mites were aspirated from the culture container as they migrated from the medium, killed by freezing, desiccated and stored at 0% humidity. The allergenic component of the mite dust was extracted with water at ambient temperature. Five-hundred mg of mite powder were added to 5 ml of water (1:10 w/v) in a 15 ml conical centrifuge tube (VWR, Rochester, N.Y.), shaken for one minute and allowed to stand overnight at ambient temperature. The next day, the aqueous phase was filtered using a 0.2 µm disposable syringe filter (Nalgene, Rochester, N.Y.). The filtrate was termed mite dust allergen and used to test for induction of PGE$_2$ biosynthesis in A549 pulmonary epithelial cells.

Cell culture and treatment—The human airway epithelial cell line, A549 (American Type Culture Collection, Bethesda, Md.) was cultured and treated as previously described in Example 4. Mite allergen was added to the culture medium to achieve a final concentration of 1000 ng/ml. Eighteen hours later, the media were sampled for PGE$_2$ determination.

Results—Table 5 depicts the extent of inhibition by hops derivatives of PGE$_2$ biosynthesis in A549 pulmonary cells stimulated by mite dust allergen. All hops derivatives tested were capable of significantly inhibiting the stimulatory effects of mite dust allergens.

TABLE 5

PGE$_2$ inhibition by hops derivatives in A549 pulmonary epithelial cells stimulated by mite dust allergen.

| Test Material | Percent PGE$_2$ Inhibition |
|---|---|
| Alpha hop (AA) | 81 |
| Aromahop OE | 84 |
| Isohop (IAA) | 78 |
| Beta acids (BA) | 83 |
| Hexahop (HHIAA) | 82 |
| Redihop (RIAA) | 81 |
| Tetrahop (THIAA) | 76 |

This example illustrates that hops derivatives are capable of inhibiting the PGE$_2$ stimulatory effects of mite dust allergens in A549 pulmonary cells.

Example 6

Inhibition of 5-lipoxygease Activity by Derivatives of Alpha-Acids from Hops (*Humulus lupulus*)

Test Materials and Reagents—Standardized (see Table 1) aqueous solutions of fractions isolated or derived from hops (*Humulus lupulus*) were obtained from BetaTech (Washington, D.C.). The solutions were diluted into DMSO to contain 1 mg/ml of the reference compounds. If necessary, the sample was clarified by centrifugation at 12000×g for 5 minutes. For testing, serial dilutions were made in DMSO. The Lipoxygenase Inhibitor Screening Assay Kit (LISAK) from Cayman (#760700, Chicago, Ill.) was used to assess the effects of test material on lipoxygenase activity. Included with the kit were soybean 15-lipoxygenase (#60700), and linoleic acid. Potato 5-lipoxygenase (#60401) was purchased from Cayman separately. Positive control compounds included caffeic acid (Cayman #70602), Trolox (Sigma 238813) and Rev 5901 (Sigma R5523); these were of the highest purity commercially available. Boswellin (RM07781) was provided by Metagenics, Inc., Gig Harbor, Wash.).

Assay—The 5-lipoxygenase (5-LOX) assay and calculations were performed in accordance with the manufacturer's protocol. Briefly, assay buffer was prepared by diluting the contents of LISAK vial #1 with nine parts of HPLC grade water to yield a final concentration of 0.1M Tris-HCl (pH 7.4). 5-LOX was diluted into assay buffer so that the final reaction rate was approximately 10 nmol min$^{-1}$ ml$^{-1}$.

The substrate solution was prepared adding 25 ml of an ethanolic solution of linoleic acid (LISAK vial#6) to 25 ml of 0.1 M KOH (LISAK vial#7) and diluting with 950 ml of HPLC grade water. The final substrate concentration was 1 mM.

The 5-LOX reaction was initiated by adding 10 ml linoleic acid to a reaction mixture consisting of 90 ml of diluted enzyme (or assay buffer for the reaction blank), 10 ml assay buffer and 10 ml of test inhibitor or DMSO. After 5 minutes at room temperature, the reaction was terminated by the addition of 100 ml of the proprietary LISAK chromagen, prepared by mixing equal amounts of LISAK vials 2 and 3. The absorbance was measured with a 492 nm (8 nm bandwidth) filter in a Victor™ Multilabel Counter equipped with an absorbance package (Perkin Elmer #1420-042, #1420-115; Boston, Mass.). The reaction rate was determined as follows:

$$DA\ min^{-1} = (Abs_{rx} - Abs_{enzyme\ blank})/5\ minutes$$

$$nmol\ min^{-1}\ ml^{-1} = DA\ min^{-1}/9.47\ mM^{-1},$$

where the extinction coefficient has been adjusted for the path length created by a volume of 210 ml in a 0.3 cm$^2$ microtiter well.

Calculations—Dose-response curves were generated using CalcuSyn (BIOSOFT, Ferguson, Mo.). A minimum of four concentrations of each test material or positive control was used for computation.

Results—The results demonstrate that the chemically modified acids from hops inhibit the activity of potato 5-LOX (Table 6). Unexpectedly, while neither of the native alpha or beta acids affected the enzyme at the highest concentration tested, the reduced and/or isomerized alpha acids showed significant at inhibition at concentrations as low as 5 mg/ml, in line with the potent positive control Trilox. In order of apparent effectiveness Isohop (consisting of 25% w/w iso-alpha acids) and HexaHop Gold were the most effective for inhibiting the enzyme at a concentration of 5 μg/ml. Redihop and Tetrahop were slightly less effective but exhibited substantial inhibition at the 10 μg/ml concentration.

TABLE 6

The inhibitory effect of hops-derived compounds on potato 5-lipoxygenase activity.†

| | Percent Inhibition (SEM) | | | |
|---|---|---|---|---|
| | 1 μg/ml | 5 μg/ml | 10 μg/ml | 50 μg/ml |
| Test Material | | | | |
| Alpha Hop | 6.7 (0.9) | 6.5 (2.5) | 4.7 (5.8) | 10.6 (5.8) |
| Beta Stab | −1.2 (2.5) | 0.0 (1.3) | 2.7 (0.8) | 8.6 (0.9) |
| Aromahop OE | 5.2 (2.4) | 13.0 (2.9) | 16.9 (6.0) | 41.5 (17.8) |
| Isohop | 3.3 (1.0) | 9.8 (0.4)‡ | 16.9 (0.8) | 35.8 (0.3) |
| Redihop | 2.9 (2.0) | 8.2 (0.7) | 15.0 (0.9)‡ | 31.4 (0.6) |
| Tetrahop Gold | 3.3 (1.9) | 12.4 (1.7) | 21.0 (2.0) | 43.2 (1.6)‡ |
| Hexahop Gold | 3.7 (0.6) | 11.2 (0.2)‡ | 20.8 (0.1) | 40.2 (0.7) |
| Positive Controls | | | | |
| Caffeic acid | −1.1 (1.8) | −2.1 (0.7) | −6.1 (1.8) | 0.9 (6.2) |
| Boswellin | 2.8 (1.5) | 2.2 (1.4) | 2.4 (1.7) | 15.7 (4.9) |
| Rev5901 | 2.2 (1.7) | 0.8 (1.6) | −0.4 (1.6) | 1.8 (1.0) |
| Trolox | 0.5 (1.6) | 13.0 (1.4)‡ | 26.6 (2.0) | 96.8 (0.3) |

†Relative to control activity of 13, 6, 15.5 and 15.4 nmol/min/ml, respectively, for the three sets of experiments.
‡The lowest concentration at which inhibition was significantly (p < 0.05) greater than the solvent control.

A ranking of the ingredients is provided in Table 7. The IC$_{25}$ values were calculated using the median Effect Model in CalcuSyn. When ranked in this method Hexahop Gold, Tetrahop Gold and Isohop are roughly equivalent, IC$_{25}$=16, 18 and 23 μg/ml, respectively, followed by Redihop with and IC$_{25}$ of 30 μg/ml.

These unexpected results suggest that these derivatives of hops bitter acids may have utility in treating the myriad of diseases associated with inflammatory states characterize by hyperactivity of 5-LOX.

TABLE 7

Concentrations of hops compounds and positive controls estimated to inhibit 5-LOX activity by twenty-five percent (IC$_{25}$).

| Test Material | Expt | IC$_{25}$† [μg/ml] |
|---|---|---|
| Redihop | 158 | 32 (21-47) |
| | 160 | 27 (16-45) |
| Hexahop | 158 | 17 (14-21) |
| | 160 | 18 (13-24) |
| Isohop | 158 | 23 (19-27) |
| | 160 | 23 (18-29) |
| Alphahop | 158 | >50 |
| | 160 | >50 |
| Beta Stab | 159 | >50 |
| | 161 | >50 |
| Aromahop | 159 | 49 (27-92) |
| | 161 | 9 (6-12) |
| Tetrahop | 159 | 13 (12-15) |
| | 161 | 18 (12-27) |
| Trolox | 238 | 8 (6-12) |
| | 239 | 6 (4-9) |
| | 240 | 6 (4-9) |
| Boswellin | 238 | >50 |
| | 239 | >50 |
| | 240 | >50 |

TABLE 7-continued

Concentrations of hops compounds and positive controls estimated to inhibit 5-LOX activity by twenty-five percent ($IC_{25}$).

| Test Material | Expt | $IC_{25}$† [µg/ml] |
|---|---|---|
| Caffeic acid | 159 | >50 |
| | 161 | >50 |

†values presented as µg/ml wherein the parenthetic values represent 95% confidence intervals.

Example 7

Lack of Direct COX-2 Inhibition by Reduced Isoalpha Acids

The objective of this example was to determine whether magnesium reduced isoalpha acids can act as a direct inhibitor of COX-2 enzymatic activity.

Materials—Test compounds were prepared in dimethyl sufoxide (DMSO) and stored at −20° C. LPS was purchased from Sigma-Aldrich (St. Louis, Mo.). MgRIAA was supplied by Metagenics (San Clemente, Calif.), and the commercial formulation of celecoxib was used (Celebrex™, Searle & Co., Chicago, Ill.).

Cell Culture—The murine macrophage RAW 264.7 cell line was purchased from ATCC (Manassas, Va.) and maintained according to their instructions. Cells were subcultured in 96-well plates at a density of $8\times10^4$ cells per well and allowed to reach 90% confluence, approximately 2 days. LPS (1 µg/ml) or PBS alone was added to the cell media and incubated for 12 hrs. The media was removed from the wells and LPS (1 µg/ml) with the test compounds dissolved in DMSO and serum-free RPMI, were added to the wells to achieve final concentrations of MgRIAA at 20, 5.0, 1.0 and 0.1 µg/ml and celecoxib at 100, 10, 1 and 0.1 ng/ml. Each concentration was run in 8 duplicates. Following 1 hr of incubation with the test compounds, the cell media were removed and replaced with fresh media with test compounds with LPS (1 µg/ml) and incubated for 1 hr. The media were removed from the wells and analyzed for the PGE2 synthesis. $PGE_2$ assay—A commercial, non-radioactive procedure for quantification of $PGE_2$ was employed (Cayman Chemical, Ann Arbor, Mich.). Samples were diluted 10 times in EIA buffer and the recommended procedure of the manufacturer was used without modification. The $PGE_2$ concentration was represented as picograms per ml. The manufacturer's specifications for this assay include an intra-assay coefficient of variation of <10%, cross reactivity with $PGD_2$ and $PGF_2$ of less than 1% and linearity over the range of 10-1000 pg $ml^{-1}$.

COX-2 specific inhibitor celecoxib dose-dependently inhibited COX-2 mediated $PGE_2$ synthesis (100, 10, 1 and 0.1 ng/ml) while no significant $PGE_2$ inhibition was observed with MgRIAA. The data suggest that MgRIAA is not a direct COX-2 enzymatic inhibitor like celocoxib (FIG. 5)

Example 8

Inhibition of iNOS and COX-2 Protein Expression by MgRIAA

Cellular extracts from RAW 264.7 cells treated with MgRIAA and stimulated with LPS were assayed for iNOS and COX-2 protein by Western blot.

Materials—Test compounds were prepared in dimethyl sufoxide (DMSO) and stored at −20° C. MgRIAA was supplied by Metagenics (San Clemente, Calif.). Parthenolide was purchased from Sigma-Aldrich (St. Louis, Mo.). The PI3K inhibitors Wortmannin and LY294002 were purchased from EMD Biosciences (San Diego, Calif.). Antibodies generated against COX-2 and iNOS were purchased from Cayman Chemical (Ann Arbor, Mich.). Antibodies generated against GAPDH were purchased from Novus Biological (Littleton, Colo.). Secondary antibodies coupled to horseradish peroxidase were purchased from Amersham Biosciences (Piscataway, N.J.).

Cell Culture—The murine macrophage RAW 264.7 cell line was purchased from ATCC (Manassas, Va.) and maintained according to their instructions. Cells were grown and subcultured in 24-well plates at a density of $3\times10^5$ cells per well and allowed to reach 90% confluence, approximately 2 days. Test compounds were added to the cells in serum free medium at a final concentration of 0.4% DMSO. Following 1 hr of incubation with the test compounds, LPS (1 µg/ml) or phosphate buffered saline alone was added to the cell wells and incubation continued for the indicated times.

Western Blot—Cell extracts were prepared in Buffer E (50 mM HEPES, pH 7.0; 150 mM NaCl; 1% triton X-100; 1 mM sodium orthovanadate; aprotinin 5 µg/ml; pepstatin A 1 µg/ml; leupeptin 5 µg/ml; phenylmethanesulfonyl fluoride 1 mM). Briefly, cells were washed twice with cold PBS and Buffer E was added. Cells were scraped into a clean tube, following the centrifugation at 14,000 rpm for 10 minutes at 4° C., the supernatant was taken as total cell extract. Cell extracts (50 µg) were electrophoresed through a pre-cast 4%-20% Tris-HCl Criterion gel (Bio-Rad, Hercules, Calif.) until the front migration dye reached 5 mm from the bottom of the gel. The proteins were transferred to nitrocellulose membrane using a semi-dry system from Bio-Rad (Hercules, Calif.). The membrane was washed and blocked with 5% dried milk powder for 1 hour at room temperature. Incubation with the primary antibody followed by the secondary antibody was each for one hour at room temperature. Chemiluminescence was performed using the SuperSignal West Femto Maximum Sensitivity Substrate from Pierce Biotechnology (Rockford, Ill.) by incubation of equal volume of luminol/enhancer solution and stable peroxide solution for 5 minutes at room temperature. The Western blot image was captured using a cooled CCD Kodak® (Rochester, N.Y.) IS1000 imaging system. Densitometry was performed using Kodak® software.

Figure 6:
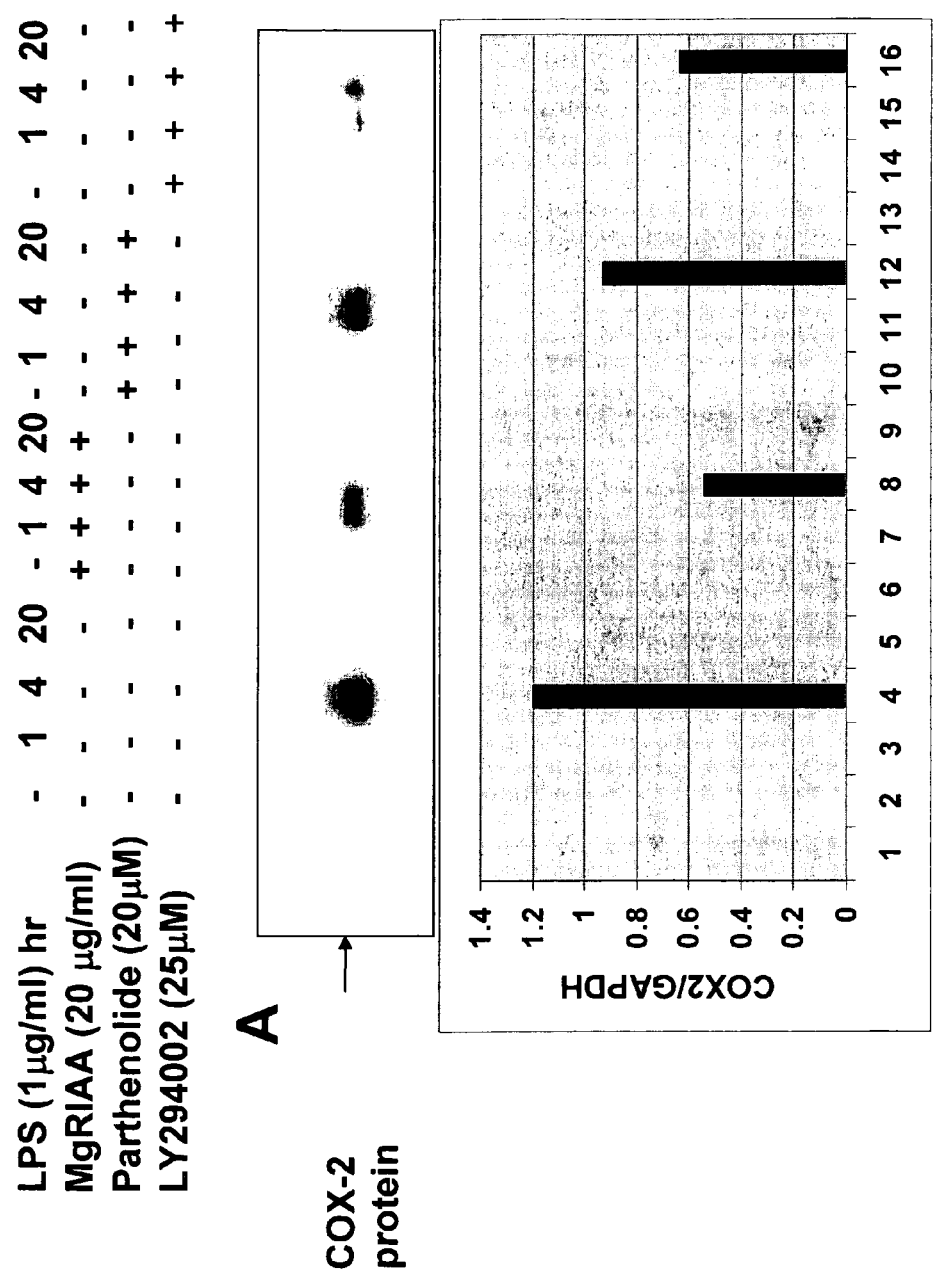
FIG. 6 provides Western blot detection of COX-2 protein expression. RAW 264.7 cells were stimulated with LPS for the indicated times, after which total cell extract was visualized by western blot [panel A]. Densitometry of the COX-2 and GAPDH bands was performed. The graph [panel B] represents the ratio of COX-2 to GAPDH.
Figure 7:
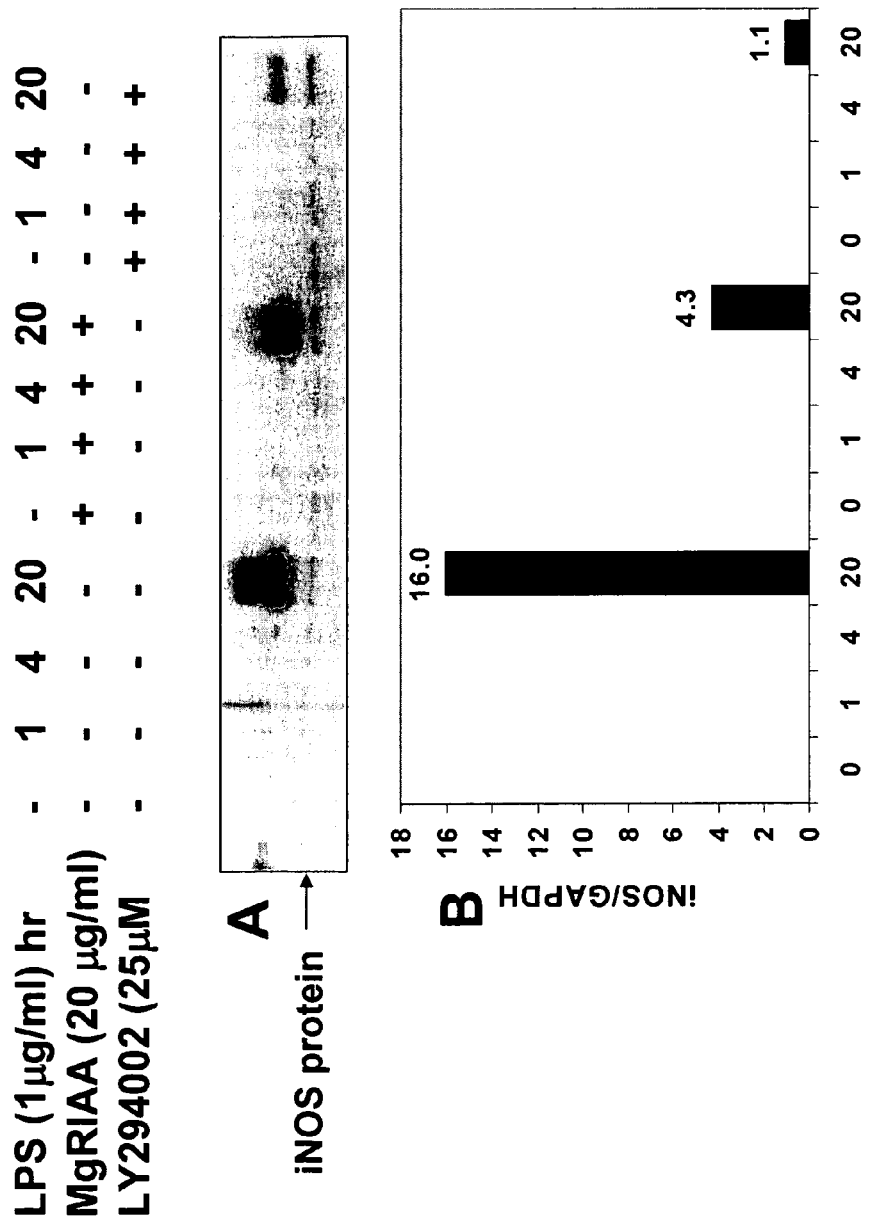
FIG. 7 provides Western blot detection of iNOS protein expression. RAW 264.7 cells were stimulated with LPS for the indicated times, after which total cell extract was visualized by western blot [panel A]. Densitometry of the iNOS and GAPDH bands was performed. The graph [panel B] represents the ratio of iNOS to GAPDH.

The percent of COX-2 and iNOS protein expression was assessed using Western blot detection. The expression of COX-2 was observed after 20 hours stimulation with LPS. As compared to the solvent control of DMSO, a reduction of 55% was seen in COX-2 protein expression by MgRIAA (FIG. 6). A specific NF-kB inhibitor parthenolide, inhibited protein expression 22.5%, while the PI3-kinase inhibitor ideceased COX-2 expression about 47% (FIG. 6). Additionally, a reduction of 73% of iNOS protein expression was observed after 20 hr stimulation with LPS (FIG. 7) by MgRIAA.

Example 9

NF-κB Nuclear Translocation and DNA Binding

Nuclear extracts from RAW 264.7 cells treated with MgRIAA and stimulated with LPS for 4 hours were assayed for NF-κB binding to DNA.

Materials—Test compounds were prepared in dimethyl sufoxide (DMSO) and stored at −20° C. MgRIAA was supplied by Metagenics (San Clemente, Calif.). Parthenolide, a specific inhibitor for NF-kB activation was purchased from Sigma-Aldrich (St. Louis, Mo.). The PI3K inhibitor LY294002 was purchased from EMD Biosciences (San Diego, Calif.).

Cell Culture—The murine macrophage RAW 264.7 cell line was purchased from ATCC (Manassas, Va.) and maintained according to their instructions. Cells were subcultured in 6-well plates at a density of $1.5 \times 10^6$ cells per well and allowed to reach 90% confluence, approximately 2 days. Test compounds MgRIAA (55 and 14 µg/ml), parthenolide (80 µM) and LY294002 (25 µM) were added to the cells in serum free media at a final concentration of 0.4% DMSO. Following 1 hr of incubation with the test compounds, LPS (1 µg/ml) or PBS alone was added to the cell media and incubation continued for an additional four hours.

Figure 8:
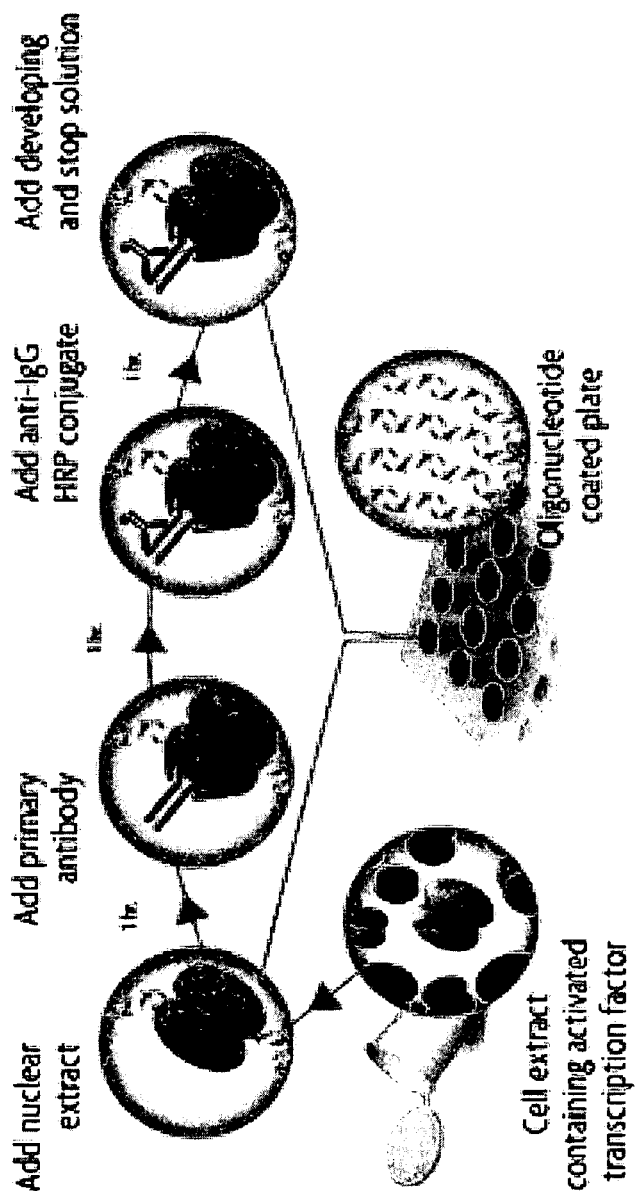
FIG. 8 provides a representative schematic of the TransAM NF-κB kit utilizing a 96-well format. The oligonucleotide bound to the plate contains the consensus binding site for NF-κB. The primary antibody detected the p50 subunit of NF-κB.

NF-κB-DNA binding—Nuclear extracts were prepared essentially as described by Dignam, et al [Nucl Acids Res 11:1475-1489, (1983)]. Briefly, cells were washed twice with cold PBS, then Buffer A (10 mM HEPES, pH 7.0; 1.5 mM $MgCl_2$; 10 mM KCl; 0.1% NP-40; aprotinin 5 µg/ml; pepstatin A 1 µg/ml; leupeptin 5 µg/ml; phenylmethanesulfonyl fluoride 1 mM) was added and allowed to sit on ice for 15 minutes. Cells were then scraped into a clean tube and processed through three cycles of freeze/thaw. The supernatant layer following centrifugation at 10,000×g for 5 min at 4° C. was the cytoplasmic fraction. The remaining pellet was resuspended in Buffer C (20 mM HEPES, pH 7.0; 1.5 mM KCl; 420 mM KCl; 25% glycerol; 0.2 M EDTA; aprotinin 5 µg/ml; pepstatin A 1 µg/ml; leupeptin 5 µg/ml; phenylmethanesulfonyl fluoride 1 mM) and allowed to sit on ice for 15 minutes. The nuclear extract fraction was collected as the supernatant layer following centrifugation at 10,000×g for 5 min at 4° C. NF-kB DNA binding of the nuclear extracts was assessed using the TransAM NF-κB kit from Active Motif (Carlsbad, Calif.) as per manufacturer's instructions. As seen in FIG. 8, the TransAM kit detected the p50 subunit of NF-κB binding to the consensus sequence in a 96-well format. Protein concentration was measured (Bio-Rad assay) and 10 µg of nuclear protein extracts were assayed in duplicate.

Figure 9:
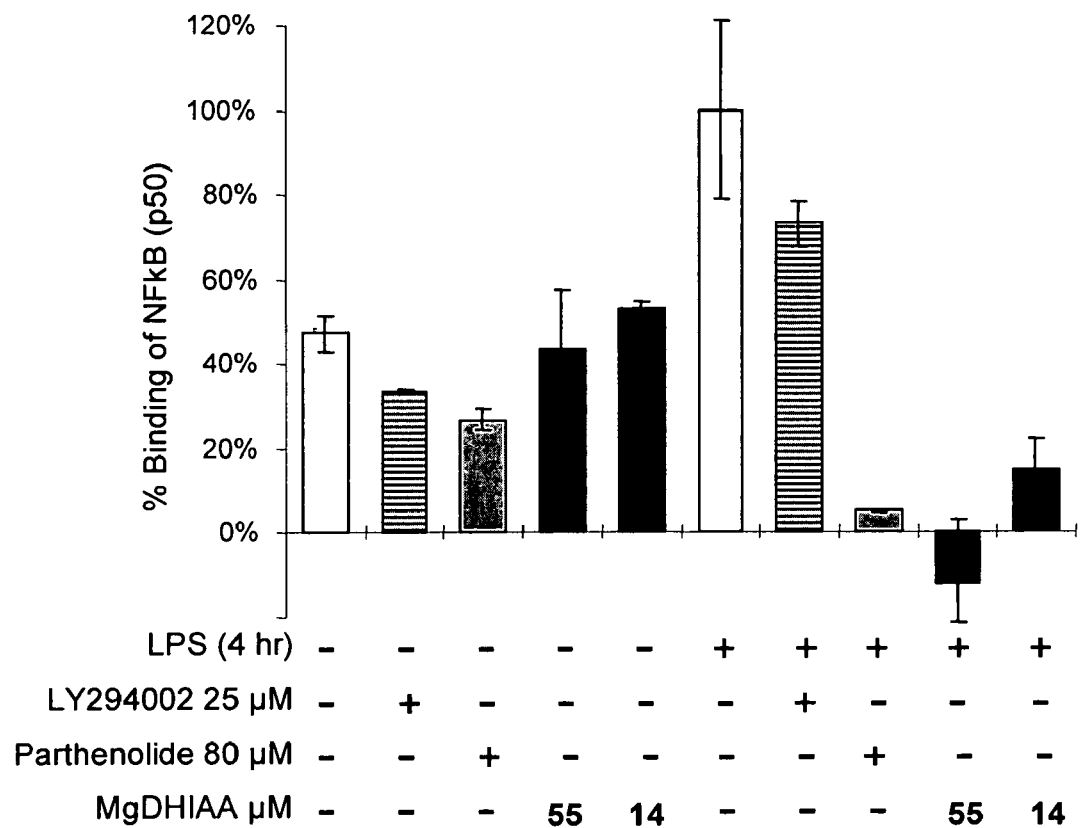
FIG. 9 provides representative binding activity of NF-κB as determined by the TransAM NF-κB kit. The percent of DNA binding was calculated relative to the LPS control (100%). The error bars represent the standard deviation (n=2). RAW 264.7 cells were treated with test compounds and LPS for 4 hr as described in the Examples section.

Analysis of nuclear extracts (10 µg) was performed in duplicate and the results are graphed in FIG. 9. Stimulation with LPS (1 µg/ml) resulted in a two-fold increase in NF-κB DNA binding. Treatment with LY294002 (a PI3 kinase inhibitor) resulted in a modest decrease of NF-κB binding as expected from previous literature reports. Parthenolide also resulted in a significant reduction in NF-κB binding as expected. A large reduction of NF-κB binding was observed with MgRIAA. The effect was observed in a dose-response manner. The reduction in NF-κB binding may result in reduced transcriptional activation of target genes, including COX-2, iNOS and TNFα.

The results suggest that the decreased NF-κB binding observed with MgDHIAA may result in decreased COX-2 protein expression, ultimately leading to a decrease in $PGE_2$ production.

Example 10

Increased Lipogenesis in 3T3-L1 Adipocytes Elicited by a Dimethyl Sulfoxide-Soluble Fraction of an Aqueous Extract of *Acacia* Bark The Model—The 3T3-L1 murine fibroblast model is used to study the potential effects of compounds on adipocyte differentiation and adipogenesis. This cell line allows investigation of stimuli and mechanisms that regulate preadipocytes replication separately from those that regulate differentiation to adipocytes [Fasshauer, M., Klein, J., Neumann, S., Eszlinger, M., and Paschke, R. Hormonal regulation of adiponectin gene expression in 3T3-L1 adipocytes. Biochem Biophys Res Commun, 290: 1084-1089, (2002); Li, Y. and Lazar, M. A. Differential gene regulation by PPARgamma agonist and constitutively active PPARgamma2. Mol Endocrinol, 16: 1040-1048, (2002)] as well as insulin-sensitizing and triglyceride-lowering ability of the test agent [Raz, I., Eldor, R., Cernea, S., and Shafrir, E. Diabetes: insulin resistance and derangements in lipid metabolism. Cure through intervention in fat transport and storage. Diabetes Metab Res Rev, 21: 3-14, (2005)].

As preadipocytes, 3T3-L1 cells have a fibroblastic appearance. They replicate in culture until they form a confluent monolayer, after which cell-cell contact triggers $G_o/G_1$ growth arrest. Terminal differentiation of 3T3-L1 cells to adipocytes depends on proliferation of both pre- and post-confluent preadipocytes. Subsequent stimulation with 3-isobutyl-1-methylxanthane, dexamethasone, and high does of insulin (MDI) for two days prompts these cells to undergo post-confluent mitotic clonal expansion, exit the cell cycle, and begin to express adipocyte-specific genes. Approximately five days after induction of differentiation, more than 90% of the cells display the characteristic lipid-filled adipocyte phenotype. Assessing triglyceride synthesis of 3T3-L1 cells provides a validated model of the insulin-sensitizing ability of the test agent.

It appears paradoxical that an agent that promotes lipid uptake in fat cells should improve insulin sensitivity. Several hypotheses have been proposed in an attempt to explain this contradiction. One premise that has continued to gain research support is the concept of "fatty acid steal" or the incorporation of fatty acids into the adipocyte from the plasma causing a relative depletion of fatty acids in the muscle with a concomitant improvement of glucose uptake [Martin, G., K. Schoonjans, et al. PPARgamma activators improve glucose homeostasis by stimulating fatty acid uptake in the adipocytes. Atherosclerosis 137 Suppl: S75-80, (1998)]. Thiazolidinediones, such as troglitazone and pioglitazone, have been shown to selectively stimulate lipogenic activities in fat cells resulting in greater insulin suppression of lipolysis or release of fatty acids into the plasma [Yamauchi, T., J. Kamon, et al. The mechanisms by which both heterozygous peroxisome proliferator-activated receptor gamma (PPARgamma) deficiency and PPARgamma agonist improve insulin resistance. J Biol Chem 276(44): 41245-54, (2001); Oakes, N. D., P. G. Thalen, et al. Thiazolidinediones increase plasma-adipose tissue FFA exchange capacity and enhance insulin-mediated control of systemic FFA availability. Diabetes 50(5): 1158-65, (2001)]. This action would leave less free fatty acids available for other tissues [Yang, W. S., W. J. Lee, et al. Weight reduction increases plasma levels of an adipose-derived anti-inflammatory protein, adiponectin. J Clin Endocrinol Metab 86(8): 3815-9, (2001)]. Thus, insulin desensitizing effects of free fatty acids in muscle and liver would be reduced as a consequence of thiazolidinedione treatment. These in vitro results have been confirmed clinically [Boden, G. Role of fatty acids in the pathogenesis of insulin resistance and NIDDM. Diabetes 46(1): 3-10, (1997); Stumvoll, M. and H. U. Haring Glitazones: clinical effects and molecular mechanisms. Ann Med 34(3): 217-24, (2002)].

Test Materials—Troglitazone, methylisobutylxanthine, dexamethasone, indomethacin, Oil red 0 and insulin were obtained from Sigma (St. Louis, Mo.). The test material was a dark brown powder produced from a 50:50 (v/v) water/alcohol extract of the gum resin of *Acacia* (AcE) sample #4909 and was obtained from Bayir Chemicals (No. 68, South Cross Road, Basavanagudi, India). The extract was standardized to contain not less than 20% apecatechin. Batch No. A Cat/2304 used in this example contained 20.8% apecatechin as determined by UV analysis. Penicillin, streptomycin, Dulbecco's modified Eagle's medium (DMEM) was from Mediatech (Herndon, Va.) and 10% FBS-HI (fetal bovine serum-heat inactivated) from Mediatech and Hyclone (Logan, Utah). All other standard reagents, unless otherwise indicted, were purchased from Sigma.

Cell culture and Treatment—The murine fibroblast cell line 3T3-L1 was purchased from the American Type Culture Collection (Manassas, Va.) and sub-cultured according to instructions from the supplier. Prior to experiments, cells were cultured in DMEM containing 10% FBS-HI added 50 units penicillin/ml and 50 µg streptomycin/ml, and maintained in log phase prior to experimental setup. Cells were grown in a 5% $CO_2$ humidified incubator at 37° C. Components of the pre-confluent medium included (1) 10% FBS/DMEM containing 4.5 g glucose/L; (2) 50 U/ml penicillin; and (3) 50 µg/ml streptomycin. Growth medium was made by adding 50 ml of heat inactivated FBS and 5 ml of penicillin/streptomycin to 500 ml DMEM. This medium was stored at 4° C. Before use, the medium was warmed to 37° C. in a water bath.

T3-T1 cells were seeded at an initial density of $6 \times 10^4$ cells/cm$^2$ in 24-well plates. For two days, the cells were allowed grow to reach confluence. Following confluence, the cells were forced to differentiate into adipocytes by the addition of differentiation medium; this medium consisted of (1) 10% FBS/DMEM (high glucose); (2) 0.5 mM methylisobutylxanthine; (3) 0.5 µM dexamethasone and (4) 10 µg/ml insulin (MDI medium). After three days, the medium was changed to post-differentiation medium consisting of 10 µg/ml insulin in 10% FBS/DMEM.

Figure 10:
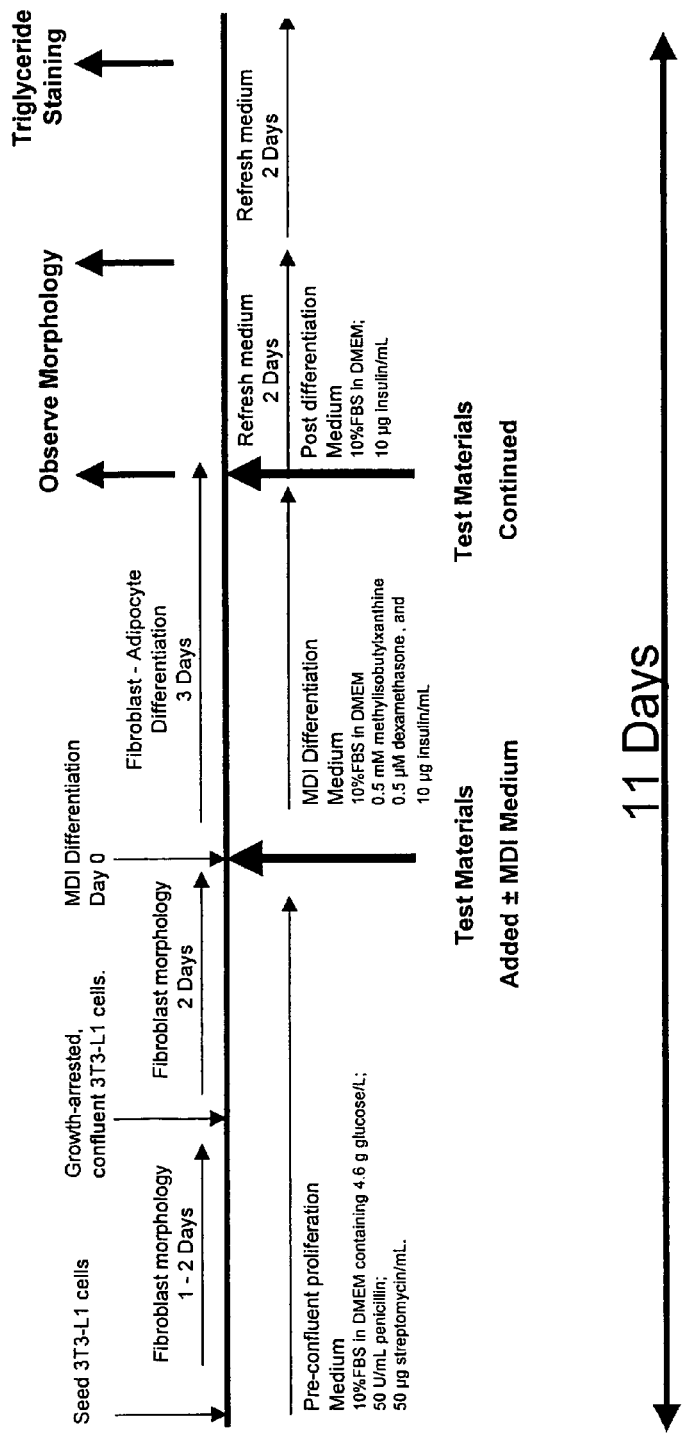
FIG. 10 is a schematic of a representative testing procedure for assessing lipogenic effect of an *Acacia* sample #4909 extract on developing and mature adipocytes. The 3T3-L1 murine fibroblast model was used to study the potential effects of the test compounds on adipocyte adipogenesis.

AcE was partially dissolved in dimethyl sulfoxide (DMSO) and added to the culture medium to achieve a concentration of 50 µg/ml at Day 0 of differentiation and throughout the maturation phase (Days 6 or 7). Whenever fresh media were added, fresh test material was also added. DMSO was chosen for its polarity and the fact that it is miscible with the aqueous cell culture media. As positive controls, indomethacin and troglitazone were added, respectively, to achieve final concentrations of 5.0 and 4.4 µg/ml. Differentiated, D6/D7 3T3-L1 cells were stained with 0.36% Oil Red 0 or 0.001% BODIPY. The complete procedure for differentiation and treatment of cells with test materials is outlined schematically in FIG. 10.

Oil Red O Staining—Triglyceride content of D6/D7-differentiated 3T3-L1 cells was estimated with Oil Red O according to the method of Kasturi and Joshi [Kasturi, R. and Joshi, V. C. Hormonal regulation of stearoyl coenzyme A desaturase activity and lipogenesis during adipose conversion of 3T3-L1 cells. J Biol Chem, 257: 12224-12230, 1982]. Monolayer cells were washed with PBS (phosphate buffered saline, Mediatech) and fixed with 10% formaldehyde for ten minutes. Fixed cells were stained with an Oil Red O working solution of three parts 0.6% Oil Red O/isopropanol stock solution and two parts water for one hour and the excess stain was washed once with water. The resulting stained oil droplets were extracted from the cell with isopropanol and quantified by spectrophotometric analysis at 540 nm (MEL312e BIO-KINETICS READER, Bio-Tek Instruments, Winooski, Vt.). Results for test materials and the positive controls indomethacin and troglitazone were represented relative to the 540 nm absorbance of the solvent controls.

BODIPY Staining—4,4-Difluoro-1,3,5,7,8-penta-methyl-4-bora-3a,4a-diaza-s-indacene (BODIPY 493/503; Molecular Probes, Eugene, Oreg.) was used for quantification of cellular neutral and nonpolar lipids. Briefly, media were removed and cells were washed once with non-sterile PBS. A stock 1000× BODIPY/DMSO solution was made by dissolving 1 mg BODIPY in 1 ml DMSO (1,000 µg BODIPY/ml). A working BODIPY solution was then made by adding 10 µl of the stock solution to 990 µl PBS for a final BODIPY concentration in the working solution of 0.01 µg/µl. One-hundred µl of this working solution (1 µg BODIPY) was added to each well of a 96-well microtiter plate. After 15 min on an orbital shaker (DS-500, VWR Scientific Products, South Plainfield, N.J.) at ambient temperature, the cells were washed with 100 µl PBS followed by the addition of 100 µl PBS for reading for spectrofluorometric determination of BODIPY incorporation into the cells. A Packard Fluorocount spectrofluorometer (Model#BF10000, Meridan, Conn.) set at 485 nm excitation and 530 nm emission was used for quantification of BODIPY fluorescence. Results for test materials, indomethacin, and troglitazone were reported relative to the fluorescence of the solvent controls.

A chi-square analysis of the relationship between the BODIPY quantification of all neutral and nonpolar lipids and the Oil Red O determination of triglyceride content in 3T3-L1 cells on D7 indicated a significant relationship between the two methods with p<0.001 and Odds Ratio of 4.64.

Statistical Calculations and Interpretation—AcE and indomethacin were assayed a minimum of three times in duplicate. Solvent and troglitazone controls were replicated eight times also in duplicate. Nonpolar lipid incorporation was represented relative to the nonpolar lipid accumulation of fully differentiated cells in the solvent controls. A positive response was defined as an increase in lipid accumulation assessed by Oil Red O or BODIPY staining greater than the respective upper 95% confidence interval of the solvent control (one-tail, Excel; Microsoft, Redmond, Wash.). AcE was further characterized as increasing adipogenesis better than or equal to the troglitazone positive control relative to the solvent response; the student t-test function of Excel was used for this evaluation.

Figure 11:
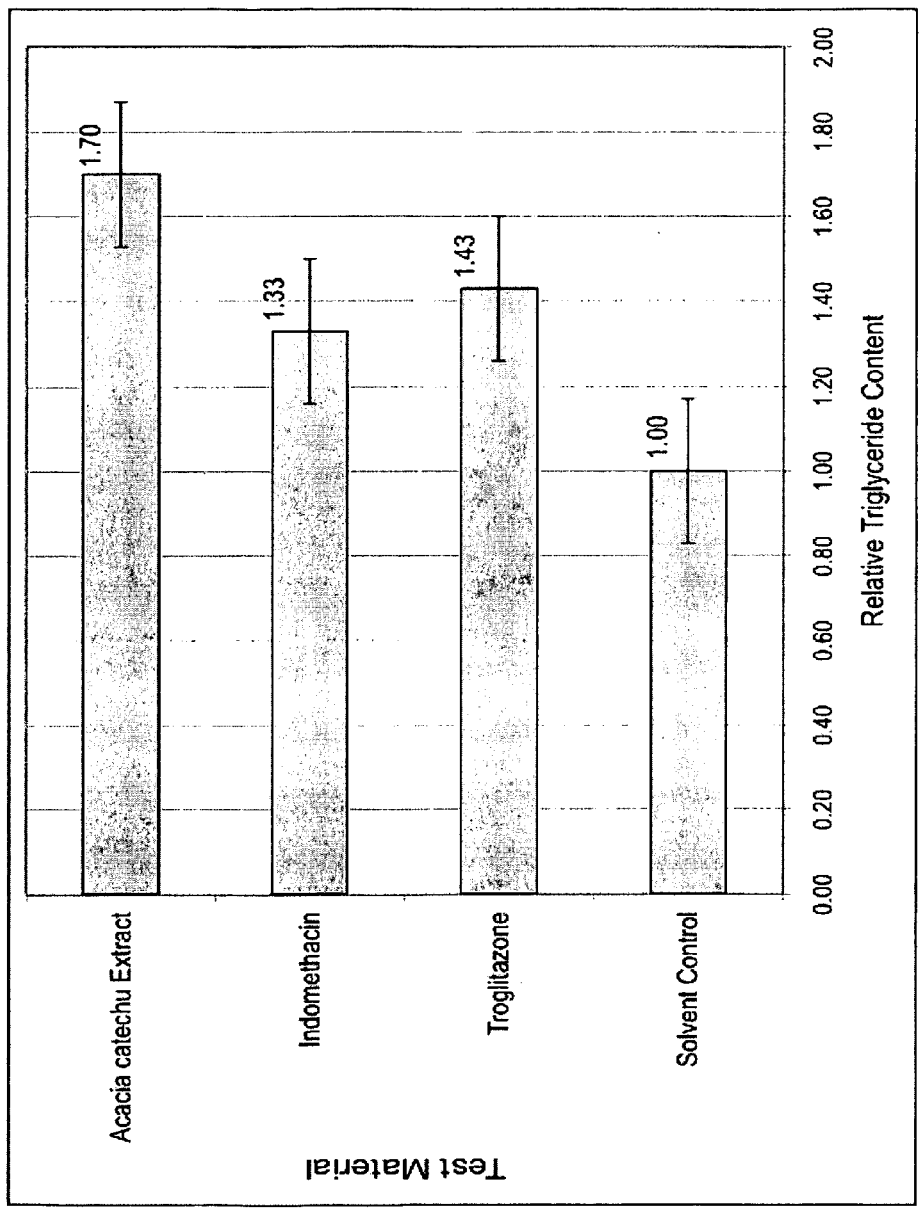
FIG. 11 is a graphic representation depicting the nonpolar lipid content of 3T3-L1 adipocytes treated with an *Acacia* sample #4909 extract or the positive controls indomethacin and troglitazone relative to the solvent control. Error bars represent the 95% confidence limits (one-tail).

Results—The positive controls indomethacin and troglitazone induced lipogenesis to a similar extent in 3T3-L1 cells (FIG. 11). Unexpectedly, the AcE produced an adipogenic response greater than either of the positive controls indomethacin and troglitazone.

The lipogenic potential demonstrated in 3T3-L1 cells, dimethyl sulfoxide-soluble components of an aqueous *Acacia* sample #4909 extract demonstrates a potential to increase insulin sensitivity in humans or other animals exhibiting signs or symptoms of insensitivity to insulin.

Example 11

Increased Adiponectin Secretion from Insulin-Resistant 3T3-L1 Adipocytes Elicited by a Dimethyl Sulfoxide-Soluble Fraction of an Aqueous Extract of *Acacia*

The Model—The 3T3-L1 murine fibroblast model as described in Example 10 was used in these experiments.

Test Materials—Troglitazone was purchased from Cayman Chemical (Ann Arbor, Mich.) while methylisobutylxanthine, dexamethasone, and insulin were obtained from Sigma (St. Louis, Mo.). The test material was a dark brown powder produced from a 50:50 (v/v) water/alcohol extract of the gum resin of *Acacia* sample #4909 and was obtained from Bayir Chemicals (No. 68, South Cross Road, Basavanagudi, India). The extract was standardized to contain not less than 20% apecatechin. Batch No. A Cat/2304 used in this example contained 20.8% apecatechin as determined by UV analysis. Penicillin, streptomycin, Dulbecco's modified Eagle's medium (DMEM) was from Mediatech (Herndon, Va.) and 10% FBS-HI (fetal bovine serum-heat inactivated from Mediatech and Hyclone (Logan, Utah). All other standard reagents, unless otherwise indicted, were purchased from Sigma.

Cell culture and Treatment—Culture of the murine fibroblast cell line 3T3-L1 to produce Day 6 differentiated adipocytes was performed as described in Example 10. 3T3-L1 cells were seeded at an initial density of $1\times10^4$ cells/cm$^2$ in 96-well plates. For two days, the cells were allowed grow to reach confluence. Following confluence, the cells were forced to differentiate into adipocytes by the addition of differentiation medium; this medium consisted of (1) 10% FBS/DMEM (high glucose); (2) 0.5 mM methylisobutylxanthine; (3) 0.5 µM dexamethasone and (4) 10 µg/ml insulin (MDI medium). From Day 3 through Day 5, the medium was changed to post-differentiation medium consisting of 10 µg/ml insulin in 10% FBS/DMEM.

Figure 12:
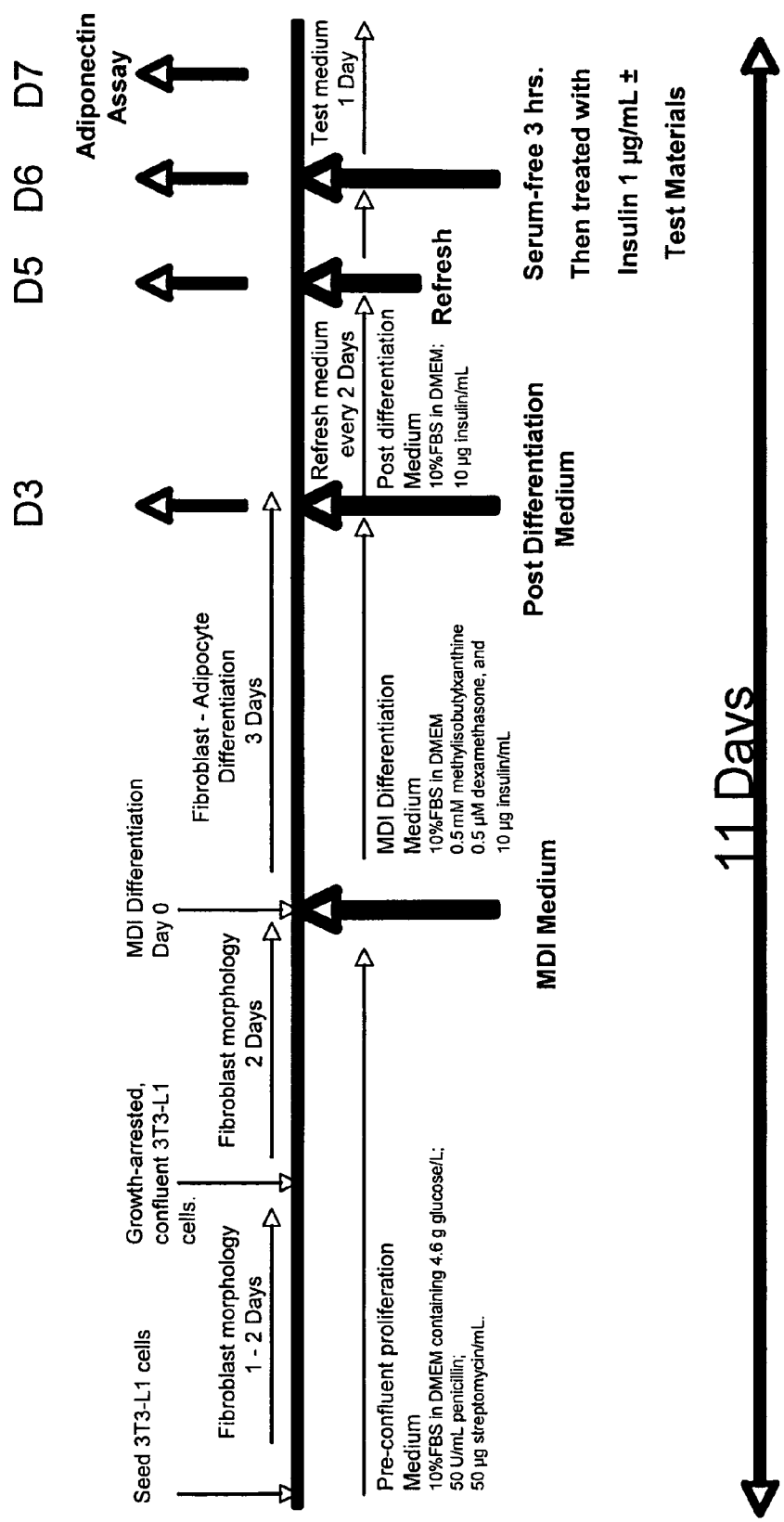
FIG. 12 is a schematic of a representative testing procedure for assessing the effect of a dimethyl sulfoxide-soluble fraction of an aqueous extract of *Acacia* sample #4909 on the secretion of adiponectin from insulin-resistant 3T3-L1 adipocytes.

Assessing the effect of *Acacia* on insulin-resistant, mature 3T3-L1 cells was performed using a modification of the procedure described by Fasshauer et al. [Fasshauer, et al. Hormonal regulation of adiponectin gene expression in 3T3-L1 adipocytes. BBRC 290:1084-1089, (2002)]. Briefly, on Day 6, cells were maintained in serum-free media containing 0.5% bovine serum albumin (BSA) for three hours and then treated with 1 µg insulin/ml plus solvent or insulin plus test material. Troglitazone was dissolved in dimethyl sulfoxide and added to achieve concentrations of 5, 2.5, 1.25 and 0.625 µg/ml. The *Acacia* extract was tested at 50, 25, 12.5 and 6.25 µg/ml. Twenty-four hours later, the supernatant medium was sampled for adiponectin determination. The complete procedure for differentiation and treatment of cells with test materials is outlined schematically in FIG. 12.

Adiponectin Assay—The adiponectin secreted into the medium was quantified using the Mouse Adiponectin Quantikine® Immunoassay kit with no modifications (R&D Systems, Minneapolis, Minn.). Information supplied by the manufacturer indicated that recovery of adiponectin spiked in mouse cell culture media averaged 103% and the minimum detectable adiponectin concentration ranged from 0.001 to 0.007 ng/ml.

Statistical Calculations and Interpretation—All assays were preformed in duplicate. For statistical analysis, the effect of *Acacia* on adiponectin secretion was computed relative to the solvent control. Differences between the doses were determined using the student's t-test without correction for multiple comparisons; the nominal five percent probability of a type I error was selected.

Potency of the test materials was estimated using a modification of the method of Hofstee [Hofstee, B. H. Non-inverted versus inverted plots in enzyme kinetics. Nature 184: 1296-1298, (1959)] for determination of the apparent Michaelis constants and maximum velocities. Substituting {relative adiponectin secretion/[concentration]} for the independent variable v/[S] and {relative adiponectin secretion} for the dependant variable {v}, produced a relationship of the form y=mx+b. Maximum adiponectin secretion relative to the solvent control was estimated from the y-intercept, while the concentration of test material necessary for half maximal adiponectin secretion was computed from the negative value of the slope.

Figure 13:
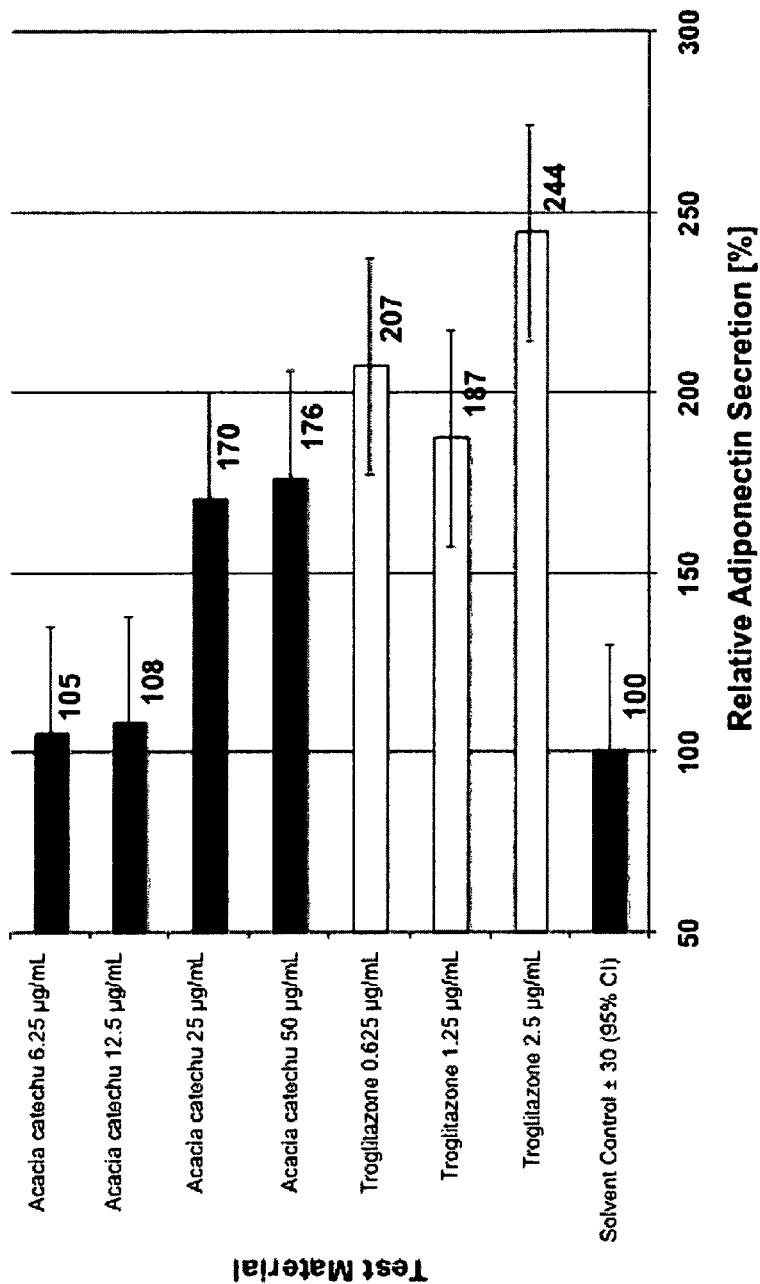
FIG. 13 is a representative bar graph depicting maximum adiponectin secretion by insulin-resistant 3T3-L1 cells in 24 hr elicited by three doses of troglitazone and four doses of a dimethyl sulfoxide-soluble fraction of an aqueous extract of *Acacia* sample #4909. Values presented are percent relative to the solvent control; error bars represent 95% confidence intervals.

Results—All concentrations tested for the positive control troglitazone enhanced adiponectin secretion with maximal stimulation of 2.44-fold at 2.5 µg/ml relative to the solvent control in insulin-resistant 3T3-L1 cells (FIG. 13). Both the 50 and 25 µg *Acacia*/ml concentrations increased adiponectin secretion relative to the solvent controls 1.76- and 1.70-fold respectively. While neither of these concentrations of *Acacia* was equal to the maximal adiponectin secretion observed with troglitazone, they were comparable to the 1.25 and 0.625 µg/ml concentrations of troglitazone.

Estimates of maximal adiponectin secretion derived from modified Hofstee plots indicated a comparable relative increase in adiponectin secretion with a large difference in concentrations required for half maximal stimulation. Maximum adiponectin secretion estimated from the y-intercept for troglitazone and *Acacia catechu* was, respectively, 2.29- and 1.88-fold relative to the solvent control. However, the concentration required for stimulation of half maximal adiponectin secretion in insulin-resistant 3T3-L1 cells was 0.085 µg/ml for troglitazone and 5.38 µg/ml for *Acacia*. Computed upon minimum apecatechin content of 20%, this latter figure for *Acacia* becomes approximately 1.0 µg/ml.

Based upon its ability to enhance adiponectin secretion in insulin-resistant 3T3-L1 cells, *Acacia*, and/or apecatechin, may be expected to have a positive effect on clinical pathologies in which plasma adiponectin concentrations are depressed.

Example 12

Increased Adiponectin Secretion from TNFα-Treated 3T3-L1 Adipocytes Elicited by a Dimethyl Sulfoxide-Soluble Fraction of an Aqueous Extract of *Acacia*

The Model—The 3T3-L1 murine fibroblast model as described in Example 10 was used in these experiments.

Test Materials—Indomethacin, methylisobutylxanthine, dexamethasone, and insulin were obtained from Sigma (St. Louis, Mo.). The test material was a dark brown powder produced from a 50:50 (v/v) water/alcohol extract of the gum resin of *Acacia* sample #4909 and was obtained from Bayir Chemicals (No. 68, South Cross Road, Basavanagudi, India). The extract was standardized to contain not less than 20% apecatechin. Batch No. A Cat/2304 used in this example contained 20.8% apecatechin as determined by UV analysis. Penicillin, streptomycin, Dulbecco's modified Eagle's medium (DMEM) was from Mediatech (Herndon, Va.) and 10% FBS (fetal bovine serum) characterized from Mediatech and Hyclone (Logan, Utah). All other standard reagents, unless otherwise indicted, were purchased from Sigma.

Figure 14:
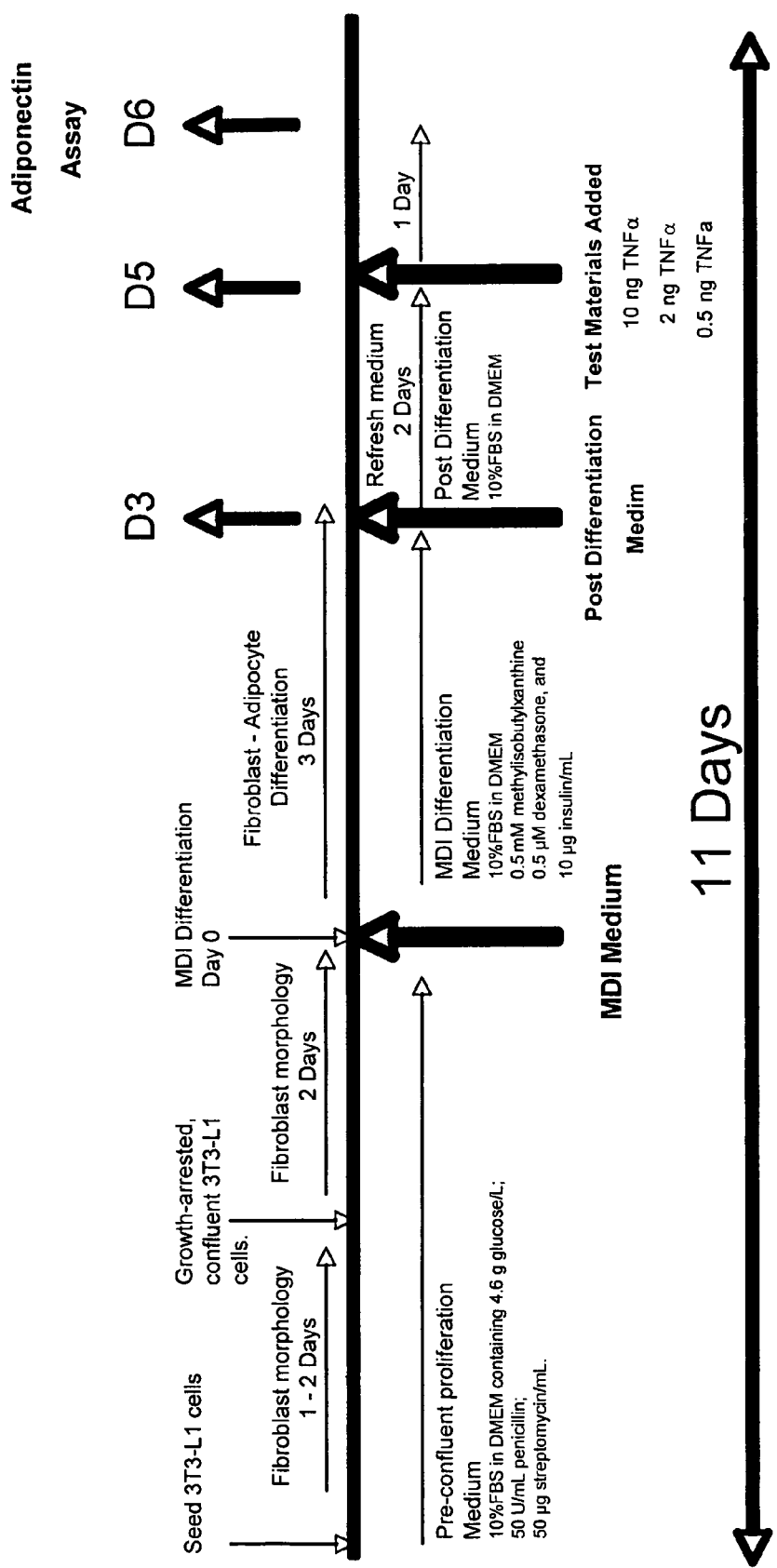
FIG. 14 is a schematic of a representative testing protocol for assessing the effect of a dimethyl sulfoxide-soluble fraction of an aqueous extract of *Acacia* sample #4909 on the secretion of adiponectin from 3T3-L1 adipocytes treated with test material plus 10, 2 or 0.5 ng TNFα/ml.

Cell culture and Treatment—Culture of the murine fibroblast cell line 3T3-L1 to produce Day 3 differentiated adipocytes was performed as described in Example 10. 3T3-L1 cells were seeded at an initial density of $1\times10^4$ cells/cm$^2$ in 96-well plates. For two days, the cells were allowed grow to reach confluence. Following confluence, the cells were forced to differentiate into adipocytes by the addition of differentiation medium; this medium consisted of (1) 10% FBS/DMEM (high glucose); (2) 0.5 mM methylisobutylxanthine; (3) 0.5 µM dexamethasone and (4) 10 µg/ml insulin (MDI medium). From Day 3 through Day 5, the medium was changed to post-differentiation medium consisting of 10% FBS in DMEM. On Day 5 the medium was changed to test medium containing 10, 2 or 0.5 ng TNFα/ml in 10% FBS/DMEM with or without indomethacin or *Acacia extract*. Indomethacin was dissolved in dimethyl sulfoxide and added to achieve concentrations of 5, 2.5, 1.25 and 0.625 µg/ml. The *Acacia* extract was tested at 50, 25, 12.5 and 6.25 µg/ml. On Day 6, the supernatant medium was sampled for adiponectin determination. The complete procedure for differentiation and treatment of cells with test materials is outlined schematically in FIG. 14.

Adiponectin Assay—The adiponectin secreted into the medium was quantified using the Mouse Adiponectin Quantikine® Immunoassay kit with no modifications (R&D Systems, Minneapolis, Minn.). Information supplied by the manufacturer indicated that recovery of adiponectin spiked in mouse cell culture media averaged 103% and the minimum detectable adiponectin concentration ranged from 0.001 to 0.007 ng/ml.

Statistical Calculations and Interpretation—All assays were preformed in duplicate. For statistical analysis, the effect of indomethacin or *Acacia catechu* on adiponectin secretion was computed relative to the solvent control. Differences among the doses and test agents were determined using the student's t-test without correction for multiple comparisons; the nominal five percent probability of a type I error was selected.

Figure 15A:
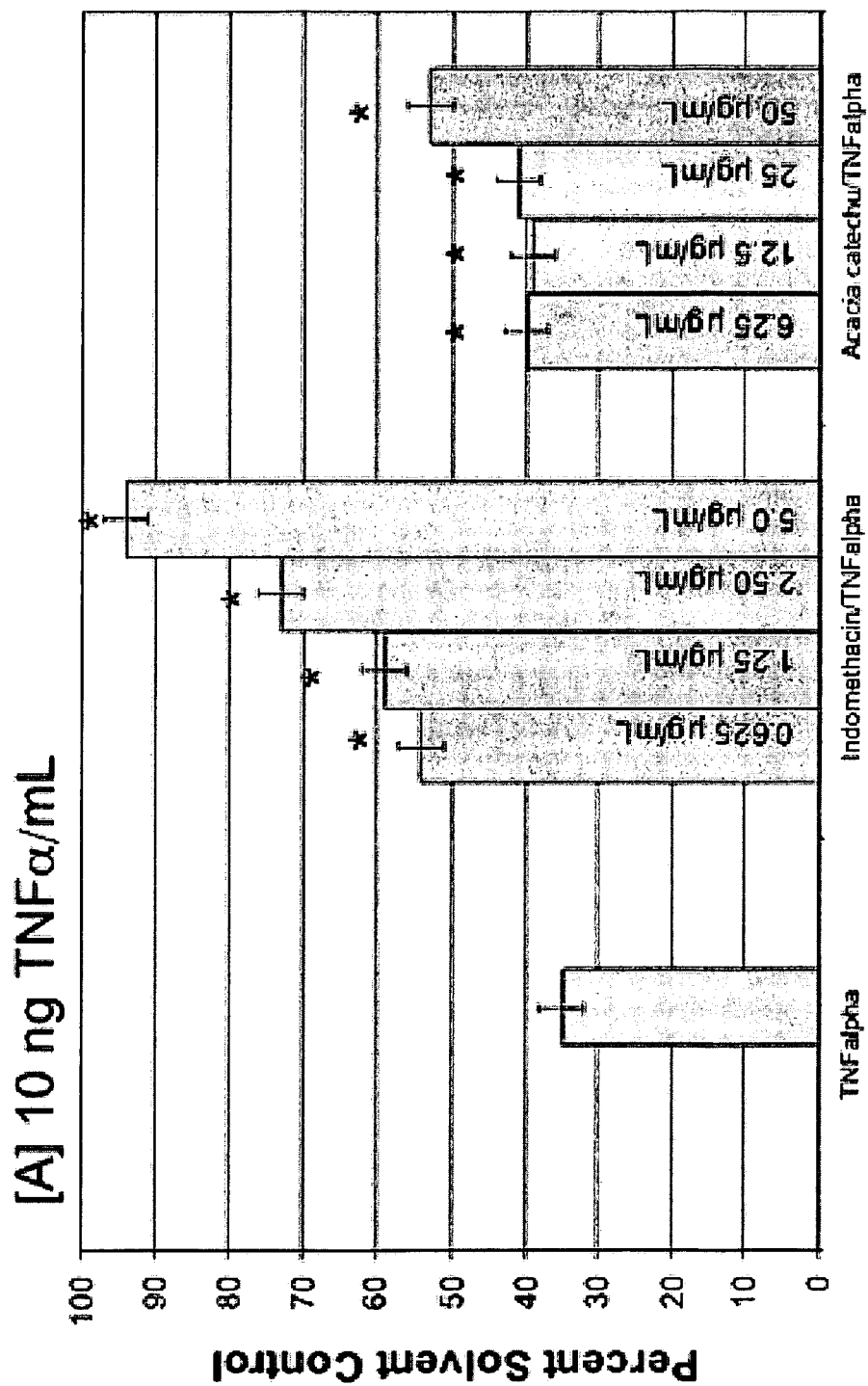
FIG. 15 depicts representative bar graphs representing adiponectin secretion by TNFα treated mature 3T3-L1 cells elicited by indomethacin or an *Acacia* sample #4909 extract. Values presented are percent relative to the solvent control; error bars represent 95% confidence intervals. *Significantly different from TNFα alone treatment (p<0.05).
Figure 15B:
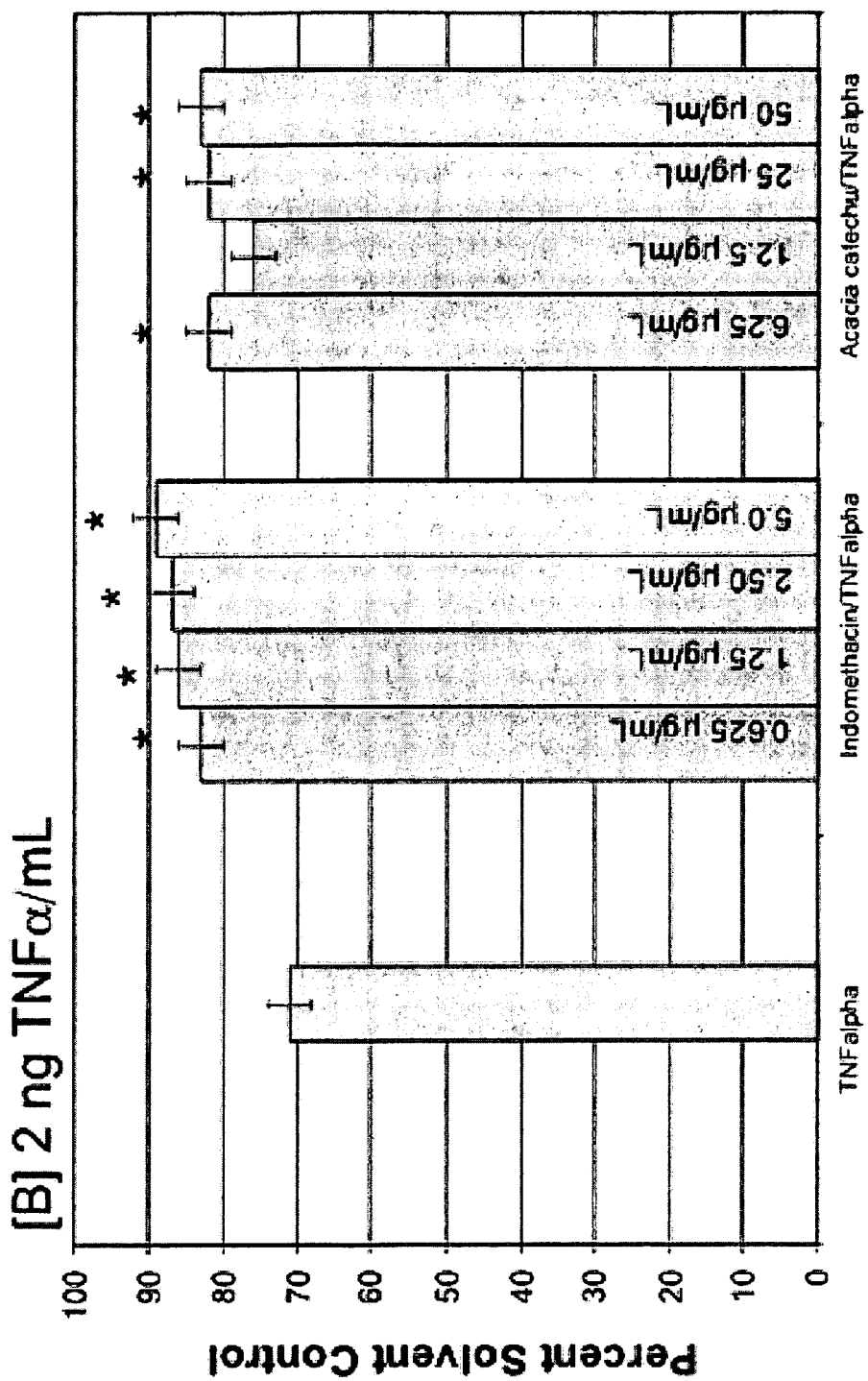
Figure 15C:
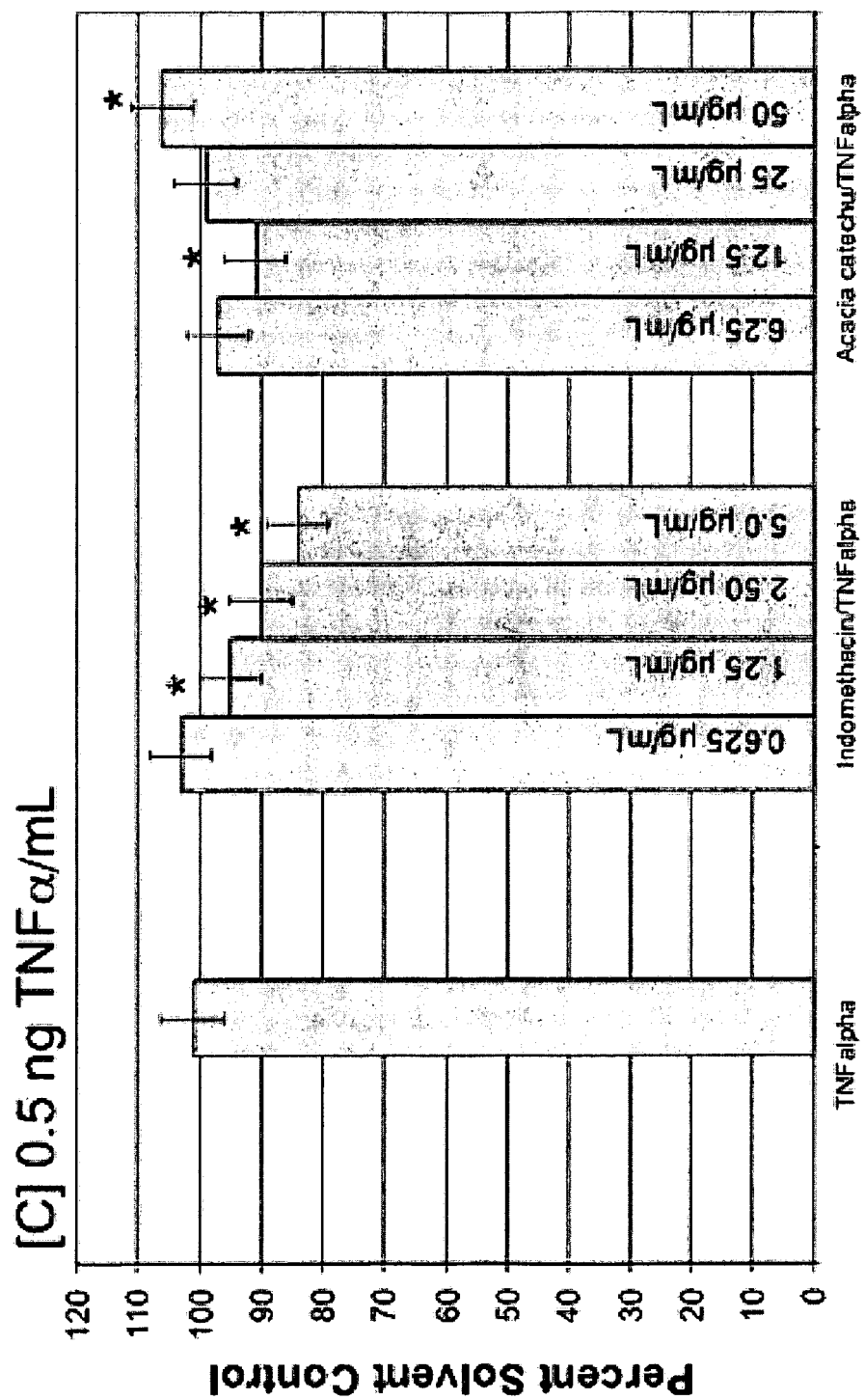

Results—TNFα significantly ($p<0.05$) depressed adiponectin secretion 65 and 29%, respectively, relative to the solvent controls in mature 3T3-L1 cells at the 10 and 2 ng/ml concentrations and had no apparent effect on adiponectin secretion at 0.5 ng/ml (FIG. 15). At 10 and 2 ng TNFα/ml, indomethacin enhanced ($p<0.05$) adiponectin secretion relative to TNFα alone at all doses tested, but failed to restore adiponectin secretion to the level of the solvent control. *Acacia* treatment in the presence of 10 ng TNFα/ml, produced a similar, albeit attenuated, adiponectin increase relative to that of indomethacin. The differences in adiponectin stimulation between *Acacia catechu* and indomethacin were 14, 20, 32, and 41%, respectively, over the four increasing doses. Since the multiple between doses was the same for indomethacin and *Acacia*, these results suggest that the potency of indomethacin was greater than the active material(s) in *Acacia* at restoring adiponectin secretion to 3T3-L1 cells in the presence of supraphysioloical concentrations of TNFα.

Treatment of 3T3-L1 cells with 2 ng TNFα and *Acacia* produced increases in adiponectin secretion relative to TNFα alone that were significant ($p<0.05$) at 6.25, 25 and 50 μg/ml. Unlike the 10 ng TNFα/ml treatments, however, the differences between *Acacia* and indomethacin were smaller and not apparently related to dose, averaging 5.5% over all four concentrations tested. As observed with indomethacin, *Acacia* did not restore adiponectin secretion to the levels observed in the solvent control.

At 0.5 ng TNFα/ml, indomethacin produced a dose-dependant decrease in adiponectin secretion that was significant ($p<0.05$) at the 2.5 and 5.0 μg/ml concentrations. Interestingly, unlike indomethacin, *Acacia catechu* increased adiponectin secretion relative to both the TNFα and solvent treated 3T3-L1 adipocytes at 50 μg/ml. Thus, at concentrations of TNFα approaching physiologic levels, *Acacia catechu* enhanced adiponectin secretion relative to both TNFα and the solvent controls and, surprisingly, was superior to indomethacin.

Based upon its ability to enhance adiponectin secretion in TNFα-treated 3T3-L1 cells, *Acacia catechu*, and/or apecatechin, would be expected to have a positive effect on all clinical pathologies in which TNFα levels are elevated and plasma adiponectin concentrations are depressed.

Example 13

A Variety of Commercial *Acacia* Samples Increase Lipogenesis in the 3T3-L1 Adipocyte Model The Model—The 3T3-L1 murine fibroblast model as described in Example 10 was used in these experiments. All chemicals and procedures used were as described in Example 10 with the exception that only the Oil Red O assay was performed to assess *Acacia catechu*-induced, cellular triglyceride content. *Acacia catechu* sample #5669 was obtained from Natural Remedies (364, 2nd Floor, 16th Main, 4th T Block Bangalore, Karnataka 560041 India); and samples #4909, 5667, and 5668 were obtained from Bayir Chemicals (No. 10, Doddanna Industrial Estate, Penya II Stage, Bangalore, 560091 Karnataka, India). *Acacia nilotica* samples #5639, 5640 and 5659 were purchased from KDN-Vita International, Inc. (121 Stryker Lane, Units 4 & 6 Hillsborough, N.J. 08844). Sample 5640 was described as bark, sample 5667 as a gum resin and sample 5669 as heartwood powder. All other samples unless indicated were described as proprietary methanol extracts of *Acacia catechu* bark.

Figure 16:
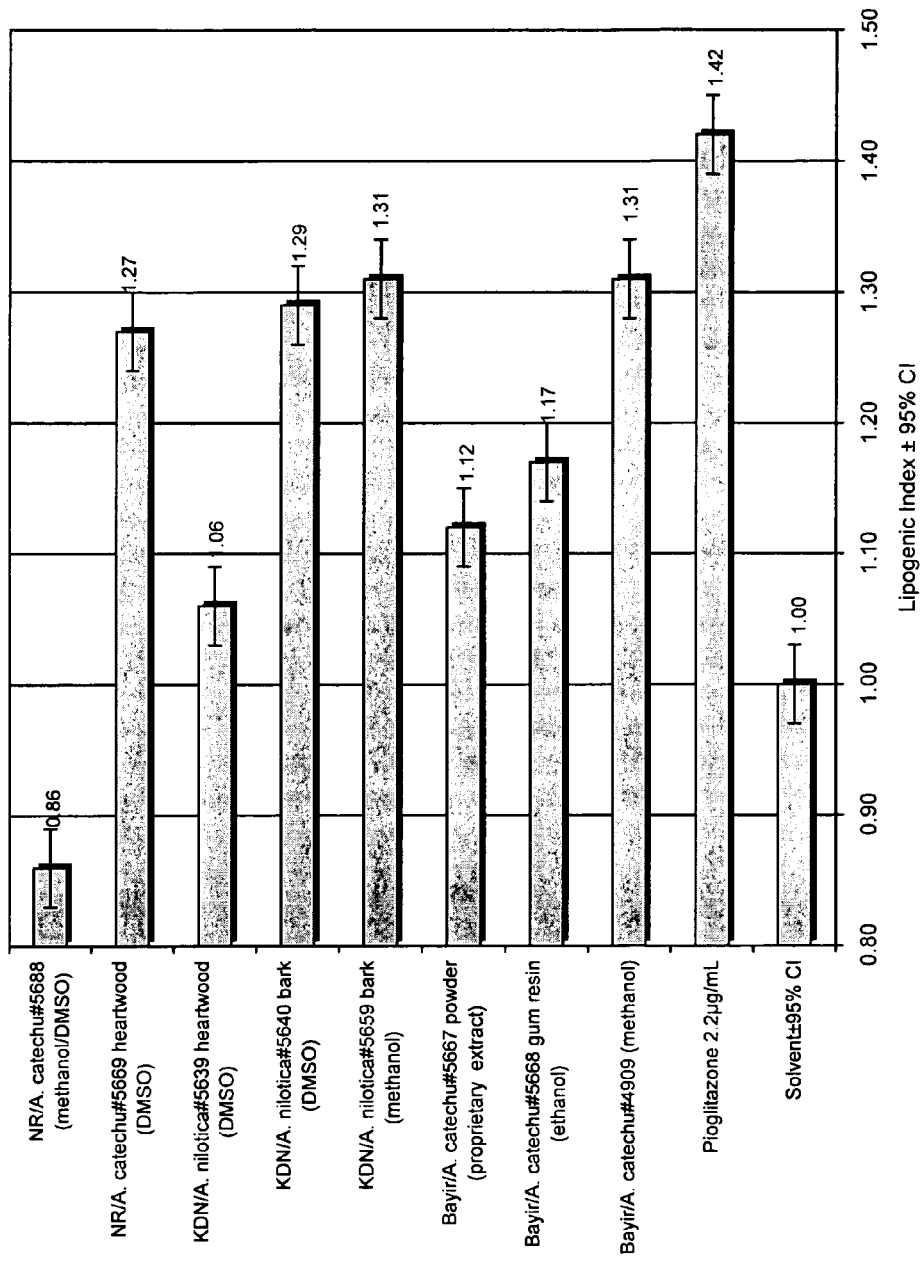
FIG. 16 graphically illustrates the relative increase in triglyceride content in insulin resistant 3T3-L1 adipocytes by various compositions of *Acacia catechu* and *A. nilotica* from different commercial sources. Values presented are percent relative to the solvent control; error bars represent 95% confidence intervals.

Results—All *Acacia* samples examined produced a positive lipogenic response (FIG. 16). The highest lipogenic responses were achieved from samples 5669 the heartwood powder (1.27), 5659 a methanol extract (1.31), 5640 a DMSO extract (1.29) and 4909 a methanol extract (1.31).

This example further demonstrates the presence of multiple compounds in *Acacia catechu* that are capable of positive modification of adipocyte physiology supporting increased insulin actions.

Example 14

A Variety of Commercial *Acacia* Samples Increase Adiponectin Secretion the TNFα-3T3-L1 Adipocyte Model The Model—The 3T3-L1 murine fibroblast model as described in Example 10 was used in these experiments. Standard chemicals used and treatment of cells was performed as noted in Examples 10 and 12. Treatment of 3T3-L1 adipocytes with TNFα differed from Example 12, however, in that cells were exposed to 2 or 10 ng TNFα/ml only. On Day 6 culture supernatant media were assayed for adiponectin as detailed in Example 12. Formulations of *Acacia* samples #4909, #5639, #5659, #5667, #5668, #5640, and #5669 were as described in Example 13.

Results—The 2 ng/ml TNFα reduced adiponectin secretion of 3T3-L1 adipocytes by 27% from the solvent control, while adiponectin secretion was maximally elevated 11% from the TNFα solvent control by 1.25 μg indomethacin/ml (Table 8). Only *Acacia* formulation #5559 failed to increase adiponectin secretion at any of the four doses tested. All other formulations of *Acacia* produced a similar maximum increase of adiponectin secretion ranging from 10 to 15%. Differences were observed, however, with regard to the concentrations at which maximum adiponectin secretion was elicited by the various *Acacia formulations*. The most potent formulation was #5640 with a maximal stimulation of adiponectin stimulation achieved at 12.5 μg/ml, followed by #4909 and #5668 at 25 μg/ml and finally #5639, #5667 and #5669 at 50 μg/ml.

TABLE 8

Relative maximum adiponectin secretion from 3T3-L1 adipocytes elicited by various formulations of Acacia in the presence of 2 ng TNFα/ml.

| Test Material | Concentration [μg/ml] | Adiponectin Index† |
|---|---|---|
| 2 ng TNFα/ml ± 95% CI | — | 1.00 ± 0.05 |
| Solvent control | — | 1.27* |

TABLE 8-continued

Relative maximum adiponectin secretion from 3T3-L1 adipocytes elicited by various formulations of Acacia in the presence of 2 ng TNFα/ml.

| Test Material | Concentration [μg/ml] | Adiponectin Index† |
|---|---|---|
| Indomethacin | 1.25 | 1.11* |
| Acacia catechu #4909 Bark (methanol extract) | 25.0 | 1.15* |
| Acacia nilotica #5639 Heartwood (DMSO extract) | 50.0 | 1.14* |
| Acacia nilotica #5659 Bark (methanol extract) | 25 | 1.02 |
| Acacia catechu #5667 Bark (methanol extract) | 50.0 | 1.10* |
| Acacia catechu #5668 (Gum resin) | 25.0 | 1.15* |
| Acacia nilotica #5640 Bark (DMSO extract) | 12.5 | 1.14* |
| Acacia catechu #5669 Heartwood powder (DMSO extract) | 50.0 | 1.14* |

†Adiponectin Index = [Adiponectin]$_{Test}$/[Adiponectin]$_{TNF\alpha\ control}$
*Significantly increased (p < 0.05) from TNFα solvent response.

The 10 ng/ml TNFα reduced adiponectin secretion of 3T3-L1 adipocytes by 54% from the solvent control, while adiponectin secretion was maximally elevated 67% from the TNFα solvent control by 5.0 μg indomethacin/ml (Table 9). Troglitazone maximally increased adiponectin secretion 51% at the lowest dose tested 0.625 μg/ml. Acacia formulation #5559 produced the lowest significant increase (p<0.05) of 12% at 25 μg/ml. All other formulations of Acacia produced a maximum increase of adiponectin secretion at 50 μg/ml ranging from 17 to 41%. The most potent formulations were #4909 and #5669 with increases in adiponectin secretion of 41 and 40%, respectively over the TNFα solvent control.

TABLE 9

Relative maximum adiponectin secretion from 3T3-L1 adipocytes elicited by various formulations of Acacia in the presence of 10 ng TNFα/ml.

| Test Material | Concentration [μg/ml] | Adiponectin Index† |
|---|---|---|
| 10 ng TNFα/ml ± 95% CI | — | 1.00 ± 0.10 |
| Solvent control | — | 1.54* |
| Indomethacin | 5.0 | 1.67* |
| Troglitazone | 0.625 | 1.51* |
| Acacia catechu #4909 Bark (methanol extract) | 50 | 1.41* |
| Acacia nilotica #5639 Heartwood (DMSO extract) | 50 | 1.26* |
| Acacia nilotica #5659 Bark (methanol extract) | 25 | 1.12* |
| Acacia catechu #5667 Bark (methanol extract) | 50 | 1.26* |
| Acacia catechu #5668 (Gum resin) | 50 | 1.30* |
| Acacia nilotica #5640 Bark (DMSO extract) | 50 | 1.17* |
| Acacia catechu #5669 Heartwood powder (DMSO extract) | 50 | 1.40* |

†Adiponectin Index = [Adiponectin]$_{Test}$/[Adiponectin]$_{TNF\alpha\ control}$
*Significantly increased (p < 0.05) from TNFα solvent response.

The observation that different samples or formulations of Acacia elicit similar responses in this second model of metabolic syndrome, further demonstrates the presence of multiple compounds in Acacia that are capable of positive modification of adipocyte physiology supporting increased insulin actions.

Example 15

Polar and Non-Polar Solvents Extract Compounds from Acacia catechu Capable of Increasing Adiponectin Secretion in the TNFα/3T3-L1 Adipocyte Model The Model—The 3T3-L1 murine fibroblast model as described in Example 10 was used in these experiments. Standard chemicals used are as noted in Examples 10 and 12. 3T3-L1 adipocytes were treated with 10 ng TNFα/ml as described in Example 12. Culture supernatant media were assayed for adiponectin on Day 6 as detailed in Example 12.

Test Materials—Large chips of Acacia catechu sample #5669 heartwood (each chip weighing between 5-10 grams) were subjected to drilling with a ⅝" metal drill bit using a standard power drill at low speed. The wood shavings were collected into a mortar, and ground into a fine powder while frozen under liquid $N_2$. This powder was then sieved through a 250 micron screen to render approximately 10 g of a fine free-flowing powder.

TABLE 10

Description of Acacia catechu extraction samples for 3T3-L1 adiponectin assay.

| Extraction solvent | Weight of extract [mg] | Percent Extracted |
|---|---|---|
| Gastric fluid[1] | 16 | 11 |
| Dimethyl sulfoxide | 40 | 27 |
| Chloroform | 0.2 | 0.13 |
| Methanol/water pH = 2 95:5 | 20 | 13 |
| Water | 10 | 6.7 |
| Ethyl acetate | 4 | 2.7 |

[1]Gastric fluid consisted of 2.90 g NaCl, 7.0 ml concentrated, aqueous HCl, 3.2 g pepsin (800-2500 activity units/mg) diluted to 1000 ml with water. Final pH was 1.2. For this extraction, the gastric fluid-heartwood suspension remained at 40 C. for one hour followed by removal of the gastric fluid in vacuo. The remaining residue was then dissolved in MeOH, filtered through a 0.45 micron PTFE syringe filter and concentrated in vacuo.

This powder was dispensed into six glass amber vials (150 mg/vial) and extracted at 40° C. for approximately 10 hr with 2 ml of the solvents listed in Table 10. Following this extraction, the heartwood/solvent suspensions were subjected to centrifugation (5800×g, 10 min.). The supernatant fractions from centrifugation were filtered through a 0.45 micron PTFE syringe filter into separate amber glass vials. Each of these samples was concentrated in vacuo. As seen in Table 2, DMSO extracted the most material from the Acacia catechu heartwood and chloroform extracted the least. All extract samples were tested at 50, 25, 12.5, and 6.25 μg/ml.

Pioglitazone was obtained as 45 mg pioglitazone tables from a commercial source as Actos® (Takeda Pharmaceuticals, Lincolnshire, Ill.). The tablets were ground to a fine powder and tested at 5.0, 2.5, 1.25 and 0.625 μg pioglitazone/ml. Indomethacin was also included as an additional positive control.

Figure 17:
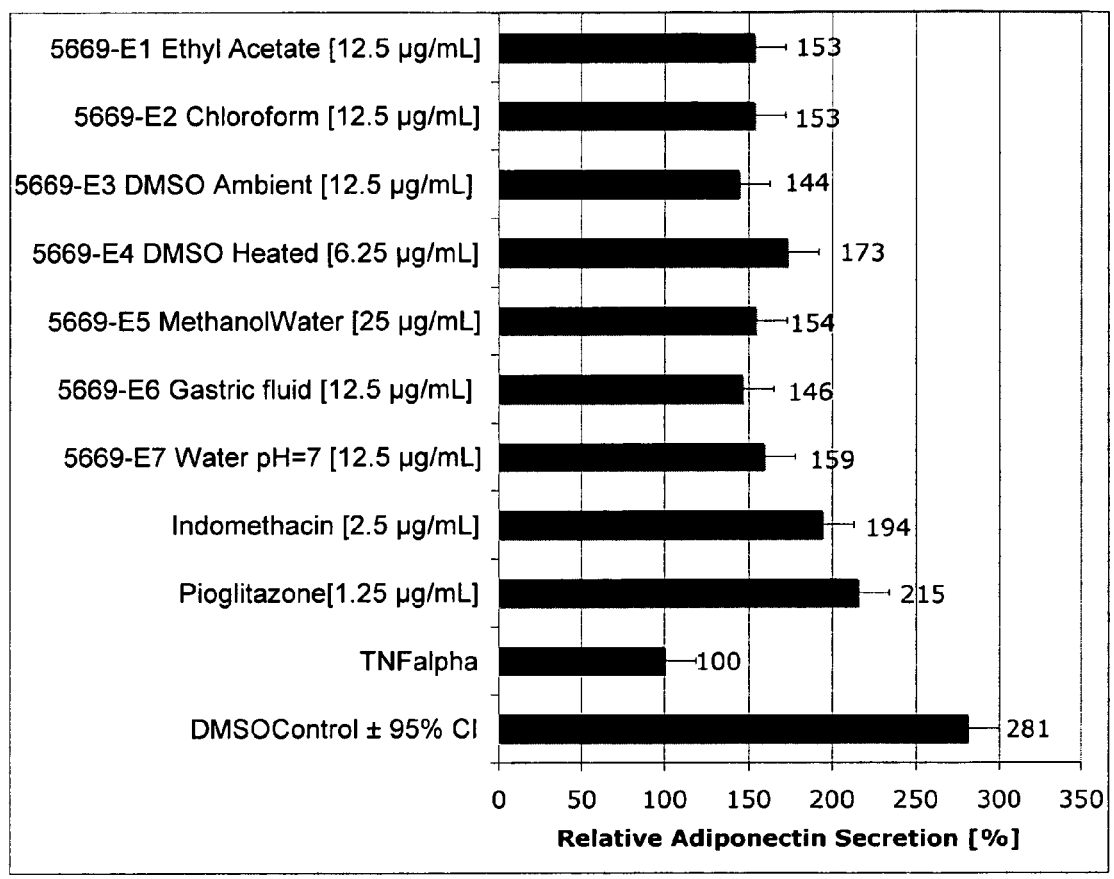
FIG. 17 graphically depicts a representation of the maximum relative adiponectin secretion elicited by various extracts of *Acacia catechu*. Values presented are percent relative to the solvent control; error bars represent 95% confidence intervals.

Results—Both positive controls pioglitazone and indomethacin increased adiponectin secretion by adipocytes in the presence of TNFα, 115 and 94% respectively (FIG. 17). Optimal pioglitazone and indomethacin concentrations were, 1.25 and 2.5 μg/ml respectively. All extracts of Acacia catechu sample #5669 increased adiponectin secretion relative to the TNFα treatment. Among the extracts, the DMSO extract was the most potent inducer of adiponectin secretion with maximal activity observed at 6.25 μg extract/ml. This result may be due to the ability of DMSO to extract a wide range of materials of varying polarity. An examination of FIG. 17 indicates that both the water extract (polar compounds) and the chloroform extract (nonpolar compounds)

were similar in their ability to increase adiponectin secretion in the TNFα/3T3-L1 adipocyte model. It is unlikely that these extracts contained similar compounds. This example illustrates the ability of solvents with differing polarities to extract compounds from *Acacia catechu* heartwood that are capable of increasing adiponectin secretion from adipocytes in the presence of a pro-inflammatory stimulus.

Example 16

*Acacia catechu* Acidic and Basic Fractions are Capable of Increasing Adiponectin Secretion in the TNFα/3T3-L1 Adipocyte Model The Model—The 3T3-L1 murine fibroblast model as described in Example 10 was used in these experiments. Standard chemicals used were as noted in Examples 10 and 12. 3T3-L1 adipocytes were treated with 10 ng TNFα/ml as described in Example 12. Culture supernatant media were assayed for adiponectin on Day 6 as detailed in Example 12.

Test Materials—*Acacia catechu* sample #5669 was extracted according to the following procedure: Alkaline isopropyl alcohol solution, (1% (v/v) 1.5N NaOH in isopropanol,) was added to approximately 50 mg of the dry *Acacia catechu* heartwood powder #5669 in a 50 ml Falcon® tube. The sample was then mixed briefly, sonicated for 30 minutes, and centrifuged for an hour to pellet the remaining solid material. The supernatant liquid was then filtered through 0.45 micron filter paper. The pH of the basic isopropanol used was 8.0, while the pH of the collected liquid was 7.0. A portion of the clear, filtered liquid was taken to dryness in vacuo and appeared as a white solid. This sample was termed the dried alkaline extract.

The remaining pelleted material was brought up in acidic isopropyl alcohol solution, (1% (v/v) 10% HCl in isopropanol,) as a red solution. This sample was mixed until the pellet material was sufficiently dispersed in the liquid and then centrifuged for 30 minutes to again pellet the remaining solid. The pale yellow supernatant fluid was passed through a 0.45 micron filter paper. The pH of the collected liquid was 3.0 and it was found that in raising the pH of the sample to 8-9 a reddish-brown precipitate was formed (dried precipitate). The precipitate was collected and dried, providing a reddish-brown solid. The supernatant liquid was again passed through a 0.45 micron filter to remove any remaining precipitate; this liquid was a deep yellow color. This remaining liquid was taken to dryness resulting in a solid brown sample and termed dried acidic extract. Recoveries for the three factions are listed in Table 11. All test materials were assayed at 50, 25, 12.5 and 6.25 µg/ml, while the pioglitazone positive control was tested at 5.0, 2.5, 1.25 and 0.625 µg/ml.

TABLE 11

Test material recovery from *Acacia catechu* heartwood powder.

| Test Material | mg collected (% *Acacia catechu* sample #5669) |
| --- | --- |
| Dried alkaline extract | 0.9 (1.8) |
| Dried precipitate | 1.2 (2.4) |
| Dried acidic extract | 1.5 (3.0) |

Results: TNFα reduced adiponectin secretion by 46% relative to the solvent control. Maximal restoration of adiponectin secretion by pioglitazone was 1.47 times the TNFα treatment observed at 1.25 µg/ml (Table 12). Of the test materials, only the dried precipitant failed to increase adiponectin secretion significantly above the TNFα only control. The acidic extract and heartwood powder (starting material) were similar in their ability to increase adiponectin secretion in the presence of TNFα, while the alkaline extract increased adiponectin secretion only at the highest dose of 50 µg/ml.

TABLE 12

Maximum adiponectin secretion elicited over four doses in TNFα/3T3-L1 model.

| Test Material | Concentration [µg/ml] | Adiponectin Index† |
| --- | --- | --- |
| DMSO Control | — | 1.86 |
| TNFα ± 95% CI | — | 1.00 ± 0.11†† |
| *Acacia catechu* sample #5669 heartwood powder | 6.25 | 1.14 |
| Dried alkaline extract | 50 | 1.19 |
| Dried precipitate | 6.25 | 1.09 |
| Dried acidic extract | 6.25 | 1.16 |
| Pioglitazone | 1.25 | 1.47 |

†Adiponectin Index = [Adiponectin]$_{Test}$/[Adiponectin]$_{TNF\alpha\ control}$
††Values >1.11 are significantly different (p < 0.05) from TNFα control.

Example 17

Decreased Interleukin-6 Secretion from TNFα-Treated 3T3-L1 Adipocytes by a Dimethyl Sulfoxide-Soluble Fraction of an Aqueous Extract of *Acacia*

Interleukin-6 (IL-6) is a multifunctional cytokine that plays important roles in host defense, acute phase reactions, immune responses, nerve cell functions, hematopoiesis and metabolic syndrome. It is expressed by a variety of normal and transformed lymphoid and nonlymphoid cells such as adipocytes. The production of IL-6 is up-regulated by numerous signals such as mitogenic or antigenic stimulation, lipopolysaccharides, calcium ionophores, cytokines and viruses [Hibi, M., Nakajima, K., Hirano T. IL-6 cytokine family and signal transduction: a model of the cytokine system. J Mol Med. 74(1):1-12, (January 1996)]. Elevated serum levels have been observed in a number of pathological conditions including bacterial and viral infection, trauma, autoimmune diseases, malignancies and metabolic syndrome [Amer, P. Insulin resistance in type 2 diabetes—role of the adipokines. Curr Mol Med.; 5(3):333-9, (May 2005)].

The Model—The 3T3-L1 murine fibroblast model as described in Example 10 was used in these experiments. Standard chemicals used were as noted in Examples 10 and 12. 3T3-L1 adipocytes were treated with 10 ng TNFα/ml as described in Example 12. Culture supernatant media were assayed for adiponectin on Day 6 as detailed in Example 12.

Test Materials—Indomethacin, methylisobutylxanthine, dexamethasone, and insulin were obtained from Sigma (St. Louis, Mo.). The test material was a dark brown powder produced from a 50:50 (v/v) water/alcohol extract of the gum resin of *Acacia catechu* sample #4909 and was obtained from Bayir Chemicals (No. 68, South Cross Road, Basavanagudi, India). The extract was standardized to contain not less than 20% apecatechin. Batch No. A Cat/2304 used in this example contained 20.8% apecatechin as determined by UV analysis. Penicillin, streptomycin, Dulbecco's modified Eagle's medium (DMEM) was from Mediatech (Herndon, Va.) and 10% FBS (fetal bovine serum) characterized from Mediatech and Hyclone (Logan, Utah). All other standard reagents, unless otherwise indicted, were purchased from Sigma.

Interleukin-6 Assay—The IL-6 secreted into the medium was quantified using the Quantikine® Mouse IL-6 Immunoassay kit with no modifications (R&D Systems, Minneapolis, Minn.). Information supplied by the manufacturer indicated that recovery of IL-6 spiked in mouse cell culture media averaged 99% with a 1:2 dilution and the minimum detectable IL-6 concentration ranged from 1.3 to 1.8 pg/ml. All supernatant media samples were assayed undiluted.

Statistical Calculations and Interpretation—All assays were preformed in duplicate. For statistical analysis, the effect of *Acacia* on adiponectin or IL-6 secretion was computed relative to the solvent control. Differences among the doses were determined using the student's t-test without correction for multiple comparisons; the nominal five percent probability of a type I error (one-tail) was selected.

Results—As seen in previous examples, TNFα dramatically reduced adiponectin secretion, while both indomethacin and the *Acacia catechu* extract increased adiponectin secretion in the presence of TNFα. Although both the indomethacin positive control and *Acacia catechu* extract demonstrated dose-related increases in adiponectin secretion, neither material restored adiponectin concentrations to those seen in the dimethyl sulfoxide controls with no TNFα (Table 13). The *Acacia catechu* extract demonstrated a potent, dose-related inhibition of IL-6 secretion in the presence of TNFα, whereas indomethacin demonstrated no anti-inflammatory effect.

An examination of the ratio of the anti-inflammatory adiponectin to the pro-inflammatory IL-6 resulted in an excellent dose-related increase in relative anti-inflammatory activity for both indomethacin and the *Acacia catechu* extract.

Example 18

Effect of a Dimethyl Sulfoxide-Soluble Fraction of an Aqueous *Acacia* Extract on Secretion of Adiponectin, IL-6 and Resistin from Insulin-Resistant 3T3-L1 Adipocytes The Model—The 3T3-L1 murine fibroblast model as described in Example 10 was used in these experiments. Standard chemicals and statistical procedures used were as noted in Examples 10 and 11. Il-6 was assayed as described in Example 17.

Resistin Assay—The amount of resistin secreted into the medium was quantified using the Quantikine® Mouse Resistin Immunoassay kit with no modifications (R&D Systems, Minneapolis, Minn.). Information supplied by the manufacturer indicated that recovery of resistin spiked in mouse cell culture media averaged 99% with a 1:2 dilution and the minimum detectable resistin concentration ranged from 1.3 to 1.8 pg/ml. All supernatant media samples were diluted 1:20 with dilution media supplied by the manufacturer before assay.

Statistical Calculations and Interpretation—All assays were preformed in duplicate. For statistical analysis, the effect of *Acacia catechu* on adiponectin or IL-6 secretion was computed relative to the solvent control. Differences among the doses were determined using the Student's t-test without correction for multiple comparisons; the nominal five percent probability of a type I error (one-tail) was selected.

TABLE 13

Decreased IL-6 and increased adiponectin secretion elicited by *Acacia catechu* sample #4909 in the TNFα/3T3-L1 model.

| Test Material | Concentration [µg/ml] | Adiponectin Index† | IL-6 Index†† | Adiponectin/IL-6 |
|---|---|---|---|---|
| DMSO control | — | 2.87* | 0.46* | 6.24* |
| TNFα control ± 95% CI | — | 1.00 ± 0.079 | 1.00 ± 0.08 | 1.00 ± 0.08 |
| Indomethacin | 5.00 | 2.69* | 1.10* | 2.45* |
| | 2.50 | 2.08* | 1.04 | 2.00* |
| | 1.25 | 1.71* | 1.01 | 1.69* |
| | 0.625 | 1.54* | 1.37* | 1.12* |
| *Acacia catechu* sample #4909 | 50.0 | 1.51* | 0.27* | 5.55* |
| | 25.0 | 1.19* | 0.71* | 1.68* |
| | 12.5 | 1.13* | 0.78* | 1.45* |
| | 6.25 | 1.15* | 0.93 | 1.23* |

The *Acacia catechu* test material or indomethacin was added in concert with 10 ng TNFα/ml to D5 3T3-L1 adipocytes. On the following day, supernatant media were sampled for adiponectin and IL-6 determination. All values were indexed to the TNFα control.
†Adiponectin Index = [Adiponectin]$_{Test}$/[Adiponectin]$_{TNF\alpha\ control}$
††IL-6 Index = [IL-6$_{Test}$ − IL-6$_{Control}$]/[IL-6$_{TNF\alpha}$ − IL-6$_{Control}$]
*Significantly different from TNFα control $p < 0.05$).

*Acacia catechu* sample #4909 demonstrated a dual anti-inflammatory action in the TNFα/3T3-L1 adipocyte model. Components of the *Acacia catechu* extract increased adiponectin secretion while decreasing IL-6 secretion. The overall effect of *Acacia catechu* was strongly anti-inflammatory relative to the TNFα controls. These results support the use of *Acacia catechu* for modification of adipocyte physiology to decrease insulin resistance weight gain, obesity, cardiovascular disease and cancer.

Results—Both troglitazone and the *Acacia* sample #4909 increased adiponectin secretion in a dose-related manner in the presence of high concentrations of insulin (Table 14). While *Acacia catechu* exhibited an anti-inflammatory effect through the reduction of IL-6 at only the 6.25 µg/ml, concentration, troglitazone was pro-inflammatory at the 5.00 and 1.25 µg/ml concentrations with no effect at the other two concentrations. Resistin secretion was increased in a dose-dependent fashion by troglitazone; however, *Acacia catechu* decreased resistin expression likewise in a dose-dependent manner.

As seen in Example 17, *Acacia catechu* sample #4909 again demonstrated a dual anti-inflammatory action in the hyperinsulemia/3T3-L1 adipocyte model. Components of the *Acacia catechu* extract increased adiponectin secretion while decreasing IL-6 secretion. Thus, the overall effect of *Acacia catechu* was anti-inflammatory relative to the high insulin controls. The effect of *Acacia catechu* on resistin secretion in the presence of high insulin concentrations was contrary to those of troglitazone: troglitazone increased resistin expression, while *Acacia catechu* further decreased resistin expression. These data suggest that the complex *Acacia catechu* extract are not functioning through PPARγ receptors. These results provide further support the use of *Acacia catechu* for modification of adipocyte physiology to decrease insulin resistance weight gain, obesity, cardiovascular disease and cancer.

TABLE 14

Effect of *Acacia catechu* extract on adiponectin. IL-6 and resistin secretion in the insulin resistant 3T3-L1 model.

| Test Material | Concentration [μg/ml] | Adiponectin Index† | IL-6 Index†† | Resistin Index††† |
|---|---|---|---|---|
| Insulin control | — | 1.00 ± 0.30* | 1.00 ± 0.23 | 1.00 ± 0.13 |
| Troglitazone | 5.00 | 1.47 | 1.31 | 1.43 |
| | 2.50 | 2.44 | 1.06 | 1.22 |
| | 1.25 | 1.87 | 1.46 | 1.28 |
| | 0.625 | 2.07 | 1.00 | 0.89 |
| *Acacia catechu* sample #4909 | 50.0 | 1.76 | 1.23 | 0.50 |
| | 25.0 | 1.70 | 0.96 | 0.61 |
| | 12.5 | 1.08 | 0.92 | 0.86 |
| | 6.25 | 1.05 | 0.64 | 0.93 |

The *Acacia catechu* test material or indomethacin was added in concert with 166 nM insulin to D5 3T3-L1 adipocytes. On the following day, supernatant media were sampled for adiponectin, IL-6 and resistin determination. All values were indexed to the insulin only control.
†Adiponectin Index = [Adiponectin]$_{Test}$/[Adiponectin]$_{Insulin\ Control}$
††IL-6 Index = [IL-6$_{Test}$]/[IL-6$_{Insulin\ Control}$]
†††Resistin Index = [Resistin$_{Test}$]/[Resistin$_{Insulin\ Control}$]
*Index values represent the mean ± 95% confidence interval computed from residual mean square of the analysis of variance. Values greater or less than Insulin control ± 95% CI are significantly different with $p < 0.05$.

Example 19

Increased Lipogenesis in Adipocytes by Phytochemicals Derived from Hops

The Model—The 3T3-L1 murine fibroblast model as described in Example 10 was used in these experiments. Standard chemicals and statistical procedures used were as noted in Example 10.

Test Materials—The hops phytochemicals used in this testing are described in Table 15 and were acquired from Betatech Hops Products (Washington, D.C., U.S.A.).

TABLE 15

Description of hops test materials.

| Hops Test Material | Description |
|---|---|
| Alpha acid solution | 82% alpha acids/2.7% beta acids/2.95% isoalpha acids by volume. Alpha acids include humulone, adhumulone, and cohumulone. |
| Rho isoalpha acids (RIAA) | Rho-isohumulone, rho-isoadhumulone, and rho-isocohumulone. |
| Isoalpha acids (IAA) | 25.3% isoalpha acids by volume. Includes cis & trans isohumulone, cis & trans isoadhumulone, and cis & trans isocohumulone. |
| Tetrahydroisoalpha acids (THIAA) | Complex hops—8.9% THIAA by volume. Includes cis & trans tetrahydro-isohumulone, cis & trans tetrahydro-isoadhumulone and cis & trans tetrahydro-isocohumulone |
| Hexahydroisoalpha acids (HHIAA) | 3.9% THIAA; 4.4% HHIAA by volume. The HHIAA isomers include hexahydro-isohumulone, hexahydro-isoadhumulone and hexahydro-isocohumulone. |
| Beta acid solution | 10% beta acids by volume; <2% alpha acids. The beta acids include lupulone, colupulone, adlupulone and prelupulone. |
| Xanthohumol (XN) | >80% xanthohumols by weight. Includes xanthohumol, xanthohumol A, xanthohumol B, xanthohumol C, xanthohumol D, xanthohumol E, xanthohumol G, xanthohumol H, desmethylxanthohumol, xanthogalenol, 4'-O-methylxanthohumol, 3'-geranylchalconaringenin, 3',5'diprenylchalconaringenin, 5'-prenylxanthohumol, flavokawin, ab-dihydroxanthohumol, and iso-dehydrocycloxanthohumol hydrate. |
| Spent hops | Xanthohumol, xanthohumol A, xanthohumol B, xanthohumol C, xanthohumol D, xanthohumol E, xanthohumol G, xanthohumol H, trans-hydroxyxanthohumol, 1",2"-dihydroxyxanthohumol C, desmethylxanthohumol B, desmethylxanthohumol J, xanthohumol I, desmethylxanthohumol, isoxanthohumol, ab dihydroxanthohumol, diprenylxanthohumol, 5"-hydroxyxanthohumol, 5'-prenylxanthohumol, 6,8-diprenylnaringenin, 8-preylnaringenin, 6-prenylnaringen, |

TABLE 15-continued

Description of hops test materials.

| Hops Test Material | Description |
|---|---|
| | isoxanthohumol, humulinone, cohumulinone, 4-hydroxybenzaldehyde, and sitosterol-3-O-b-glucopyranoside. |
| Hexahydrocolupulone | 1% hexahydrocolupulone by volume in KOH |

Cell Culture and Treatment—Hops compounds were dissolved in dimethyl sulfoxide (DMSO) and added to achieve concentrations of 10, 5, 4 or 2 µg/ml at Day 0 of differentiation and maintained throughout the maturation phase (Days 6 or 7). Spent hops was tested at 50 µg/ml. Whenever fresh media were added, fresh test material was also added. DMSO was chosen for its polarity and the fact that it is miscible with the aqueous cell culture media. As positive controls, indomethacin and troglitazone were added, respectively, to achieve final concentrations of 5.0 and 4.4 µg/ml. Differentiated, D6/D7 3T3-L1 cells were stained with 0.36% Oil Red O or 0.001% BODIPY.

Figure 18:
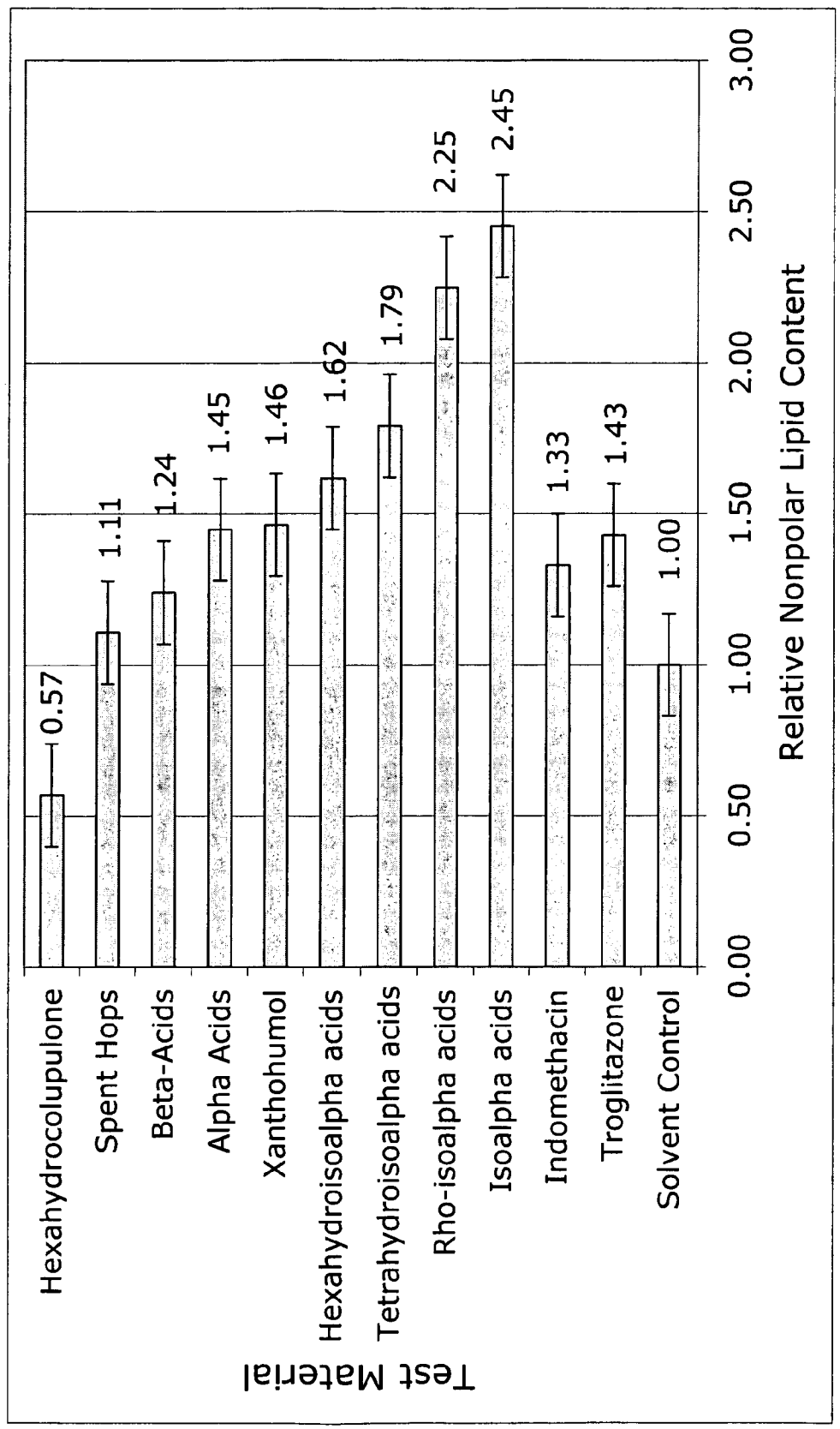
FIG. 18 graphically depicts the lipid content relative to the solvent control of 3T3-L1 adipocytes treated with hops compounds or the positive controls indomethacin and troglitazone. The 3T3-L1 murine fibroblast model was used to study the potential effects of the test compounds on adipocyte adipogenesis. Results are represented as relative nonpolar lipid content of control cells; error bars represent the 95% confidence interval.

Results—The positive controls indomethacin and troglitazone induced lipogenesis to a similar extent in 3T3-L1 cells (FIG. 18). Unexpectedly, four of the hops genera produced an adipogenic response in 3T3-L1 adipocytes greater than the positive controls indomethacin and troglitazone. These four genera included isoalpha acids, Rho-isoalpha acids, tetrahydroisoalpha acids, and hexahydroisoalpha acids. This finding is surprising in light of the published report that the binding of individual isohumulones with PPARγ was approximately one-third to one-fourth that of the potent PPARγ agonist pioglitazone [Yajima, H., Ikeshima, E., Shiraki, M., Kanaya, T., Fujiwara, D., Odai, H., Tsuboyama-Kasaoka, N., Ezaki, O., Oikawa, S., and Kondo, K. Isohumulones, bitter acids derived from hops, activate both peroxisome proliferator-activated receptor alpha and gamma and reduce insulin resistance. J Biol Chem, 279: 33456-33462, (2004)].

The adipogenic responses of xanthohumols, alpha acids and beta acids were comparable to indomethacin and troglitazone, while spent hops and hexahydrocolupulone failed to elicit a lipogenic response greater than the solvent controls.

Based upon their adipogenic potential in 3T3-L1 cells, the positive hops phytochemical genera in this stud, which included isomerized alpha acids, alpha acids and beta acids as well as xanthohumols, may be expected to increase insulin sensitivity and decrease serum triglycerides in humans or other animals exhibiting signs or symptoms of insensitivity to insulin.

Example 20

Hops Phytochemicals Increase Adiponectin Secretion in Insulin-Resistant 3T3-L1 Adipocytes The Model—The 3T3-L1 murine fibroblast model as described in Examples 10 and 11 were used in this example. Standard chemicals, hops compounds RIAA, IAA, THIAA, HHIAA, xanthohumols, hexahydrocolupulone, spent hops were as described, respectively, in Examples 11 and 19.

Cell Culture and Treatment—Cells were cultured as described in Example 11 and treated with hops phytochemicals as described in Example 33. Adiponectin assays and statistical interpretations were as described in Example 11. Potency of the test materials was estimated using a modification of the method of Hofstee for determination of the apparent Michaelis constants and maximum velocities. Substituting {relative adiponectin secretion/[concentration]} for the independent variable v/[S] and {relative adiponectin secretion} for the dependant variable {v}, produced a relationship of the form y=mx+b. Maximum adiponectin secretion relative to the solvent control was estimated from the y-intercept, while the concentration of test material necessary for half maximal adiponectin secretion was computed from the negative value of the slope.

Figure 19:
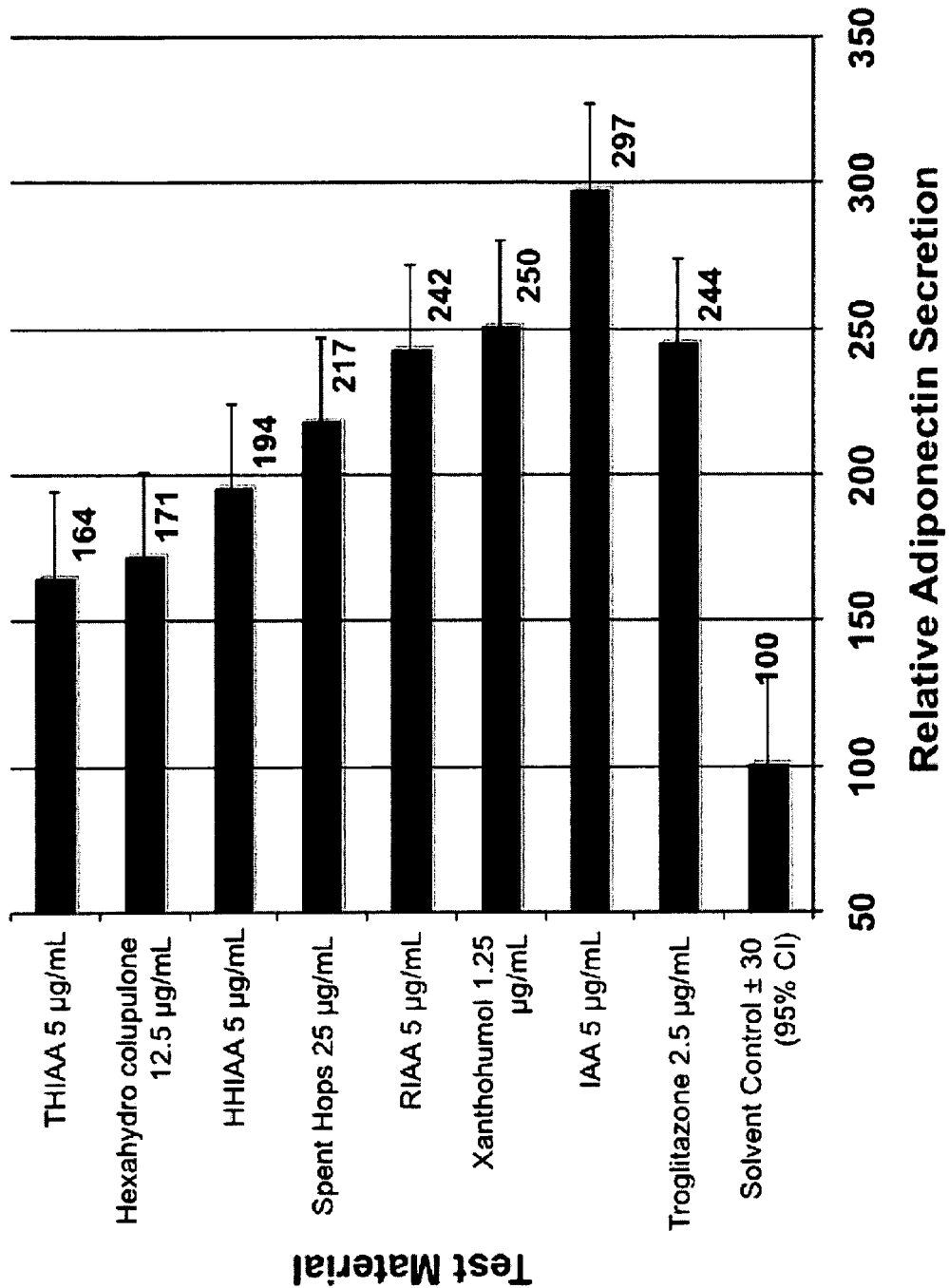
FIG. 19 is a representative bar graph of maximum adiponectin secretion by insulin-resistant 3T3-L1 cells in 24 hr elicited by the test material over four doses. Values presented are as a percent relative to the solvent control; error bars represent 95% confidence intervals. IAA=isoalpha acids, RIAA=Rho isoalpha acids, HHIA=hexahydroisoalpha acids, and THIAA=tetrahydroisoalpha acids.

Results—The positive control troglitazone maximally enhanced adiponectin secretion 2.44-fold at 2.5 µg/ml over the solvent control in insulin-resistant 3T3-L1 cells (FIG. 19). All hops phytochemicals demonstrated enhanced adiponectin secretion relative to the solvent control, with isoalpha acids producing significantly more adiponectin secretion than troglitazone (2.97-fold relative to controls). Of the four doses tested, maximal adiponectin secretion was observed at 5 µg/ml, the highest dose, for isoalpha acids, Rho isoalpha acids, hexahydroisoalpha acids and tetrahydroisoalpha acids. For xanthohumols, spent hops and hexahydro colupulone the maximum observed increase in adiponectin secretion was seen at 1.25, 25 and 12.5 µg/ml, respectively. Observed maximal relative adiponectin expression was comparable to troglitazone for xanthohumols, Rho isoalpha acids, and spent hops and less than troglitazone, but greater than control, for hexahydroisoalpha acids, hexahydro colupulone and tetrahydroisoalpha acids.

TABLE 16

Maximum adiponectin secretion and concentration of test material necessary for half maximal adiponectin secretion estimated, respectively, from the y-intercept and slope of Hofstee plots.

| Test Material | Maximum Adiponectin Secretion[1] [Fold relative to control] | Test Material at Half Maximal Secretion [µg/mL] |
|---|---|---|
| Isoalpha acids | 3.17 | 0.49 |
| Xanthohumol | 2.47 | 0.037 |
| Rho isoalpha acids | 2.38 | 0.10 |
| Troglitazone[2] | 2.29 | 0.085 |
| Spent hops | 2.21 | 2.8 |
| Hexahydroisoalpha acids[2] | 1.89 | 0.092 |
| Hexahydro colupulone[2] | 1.83 | 3.2 |
| Tetrahydroisoalpha acids | 1.60 | 0.11 |

[1]Estimated from linear regression analysis of Hofstee plots using all four concentrations tested
[2]One outlier omitted and three concentrations used for dose-response estimates As seen in Table 16, estimates of maximal adiponectin secretion derived from modified Hofstee plots (FIG. 20) supported the observations noted above. y-Intercept estimates of maximum adiponectin secretion segregated roughly into three groups: (1) isoalpha acids, (2) xanthohumols, Rho isoalpha acids, troglitazone, and spent hops, and (3) hexahydroisoalpha acids, hexahydro colupulone and tetrahydroisoalpha acids. The concentration of test material required for stimulation of half maximal adiponectin secretion in insulin-resistant 3T3-L1 cells, approximately 0.1 µg/ml, was similar for troglitazone, Rho isoalpha acids, tetrahydroisoalpha acid and hexahydroisoalpha acids. The concentration of isoalpha acids at half maximal adiponectin secretion 0.49 µg/ml was nearly 5-fold greater. Xanthohumols exhibited the lowest dose for half maximal adiponectin secretion estimated at 0.037 µg/ml. The highest concentrations for the estimated half maximal adiponectin secretion variable were seen for spent hops and hexahydro colupulone, respectively, 2.8 and 3.2 µg/ml.

Based upon their ability to enhance adiponectin secretion in insulin-resistant 3T3-L1 cells, the positive hops phytochemical genera seen in this study, isoalpha acids, Rho-isoalpha acids, tetrahydroisoalpha acids, hexahydroisoalpha acids, xanthohumols, spent hops and hexahydro colupulone, may be expected to have a positive effect on all clinical pathologies in which plasma adiponectin concentrations are depressed.

Example 21

Hops Phytochemicals Exhibit Anti-Inflammatory Activity Through Enhanced Adiponectin Secretion and Inhibition of Interleukin-6 Secretion in Insulin-Resistant 3T3-L1 Adipocytes The Model—The 3T3-L1 murine fibroblast model as described in Example 10 was used in these experiments. Adiponectin and IL-6 were assayed as described, respectively in Examples 11 and 17. Standard chemicals, hops compounds RIAA, IAA, THIAA, HHIAA, xanthohumols, hexahydrocolupulone, spent hops were as described in Examples 111 and 19.

Statistical Calculations and Interpretation—All assays were preformed in duplicate. For statistical analysis, the effect of hops derivatives on adiponectin or IL-6 secretion was computed relative to the solvent control. Differences among the doses were determined using analysis of variance without correction for multiple comparisons; the nominal five percent probability of a type I error was selected.

Results—Troglitazone and all hops derivatives tested increased adiponectin secretion in the presence of high concentrations of insulin (Table 17). Troglitazone did not decrease IL-6 secretion in this model. In fact, troglitazone, and HHCL exhibited two concentrations in which IL-6 secretion was increased, while THIAA and spent hops increased IL-6 at the highest concentration and had no effect at the other concentrations. The effect of other hops derivatives on IL-6 secretion was generally biphasic. At the highest concentrations tested, RIAA, HHIAA, and XN increased IL-6 secretion; only IAA did not. Significant decreases in IL-6 secretion were noted for RIAA, IAA, THIAA, and XN.

TABLE 17

Effect of hops compounds on adiponectin and interleukin-6 secretion insulin-resistant 3T3-L1 adipocytes.

| Test Material | Concentration [µg/ml] | Adiponectin Index† | IL-6 Index†† | Adiponectin/IL-6 |
|---|---|---|---|---|
| Insulin control±95% CI | — | 1.00 ± 0.30* | 1.00 ± 0.23 | 1.00 ± 0.30 |
| Troglitazone | 5.00 | 1.47# | 1.31# | 1.12 |
|  | 2.50 | 2.44# | 1.06 | 2.30# |
|  | 1.25 | 1.87# | 1.46# | 1.28 |
|  | 0.625 | 2.07# | 1.00 | 2.07# |
| Rho isoalpha acids (RIAA) | 5.0 | 2.42# | 1.28# | 1.89# |
|  | 2.5 | 2.27# | 0.83 | 2.73# |
|  | 1.25 | 2.07# | 0.67# | 3.09# |
|  | 0.625 | 2.09# | 0.49# | 4.27# |
| Isoalpha acids (IAA) | 5.0 | 2.97# | 0.78 | 3.81# |
|  | 2.5 | 2.49# | 0.63# | 3.95# |
|  | 1.25 | 2.44# | 0.60# | 4.07# |
|  | 0.625 | 1.73# | 0.46# | 3.76# |
| Tetrahydroisoalpha acids (THIAA) | 5.0 | 1.64# | 1.58# | 1.04 |
|  | 2.5 | 1.42# | 0.89 | 1.60# |
|  | 1.25 | 1.55# | 0.94 | 1.65# |
|  | 0.625 | 1.35# | 0.80 | 1.69# |
| Hexahydroisoalpha acids (HHIAA) | 5.0 | 1.94# | 1.49# | 1.30# |
|  | 2.5 | 1.53# | 0.74# | 2.07# |
|  | 1.25 | 1.64# | 0.67# | 2.45# |
|  | 0.625 | 1.69# | 0.73# | 2.32# |
| Xanthohumols (XN) | 5.0 | 2.41# | 1.23# | 1.96# |
|  | 2.5 | 2.11# | 0.96 | 2.20# |
|  | 1.25 | 2.50# | 0.92 | 2.72# |
|  | 0.625 | 2.29# | 0.64# | 3.58# |
| Hexahydrocolupulone (HHCL) | 50.0 | 1.65# | 2.77# | 0.60# |
|  | 25.0 | 1.62# | 1.19 | 1.36# |
|  | 12.5 | 1.71# | 0.94 | 1.82# |
|  | 6.25 | 1.05 | 1.00 | 1.05 |
| Spent Hops | 50.0 | 1.92# | 1.58# | 1.22# |
|  | 25.0 | 2.17# | 0.86 | 2.52# |
|  | 12.5 | 1.84# | 1.03 | 1.79# |
|  | 6.25 | 1.46# | 1.03 | 1.42# |

The *Acacia catechu* test material or indomethacin was added in concert with 166 nM insulin to D5 3T3-L1 adipocytes. On the following day, supernatant media were sampled for adiponectin, IL-6 and resistin determination. All values were indexed to the insulin only control.
†Adiponectin Index = [Adiponectin]$_{Test}$/[Adiponectin]$_{Insulin\ Control}$
††IL-6 Index = [IL-6$_{Test}$]/[IL-6$_{Insulin\ Control}$]
*Index value is mean ± 95% confidence interval computed from residual mean square of the analysis of variance. For adiponectin or adiponectin/IL-6, values <0.7 or >1.3 are significantly different from insulin control and for IL-6, values <0.77 or >1.23 are significantly different from insulin control.
Significantly different from insulin control p < 0.05.

The adiponectin/IL-6 ratio, a metric of overall anti-inflammatory effectiveness, was strongly positive (>2.00) for RIAA, IAA HHIA, and XN. THIAA, HHCL and spent hops exhibited positive, albeit lower, adiponectin/IL-6 ratios. For troglitazone the adiponectin/IL-6 ratio was mixed with a strongly positive response at 2.5 and 0.625 µg/ml and no effect at 5.0 or 1.25 µg/ml.

The pro-inflammatory effect of hyperinsulinemia can be attenuated in adipocytes by hops derivatives RIAA, IAA, HHIA, THIAA, XN, HHCL and spent hops. In general, the anti-inflammatory effects of hops derivatives in hyperinsulinemia conditions hyperinsulinemia uncomplicated by TNFα were more consistent than those of troglitazone.

Example 22

Hops Phytochemicals Increase Adiponectin Secretion in TNFα-Treated 3T3-L1 Adipocytes The Model—The 3T3-L1 murine fibroblast model as described in Example 10 was used in these experiments. Standard chemicals and hops compounds IAA, RIAA, HHIAA, and THIAA, were as described, respectively, in Examples 12 and 19. Hops derivatives were tested at concentrations of 0.625, 1.25, 2.5, and 5.0 µg/ml. Adiponectin was assayed as described in Example 11.

Figure 21A:
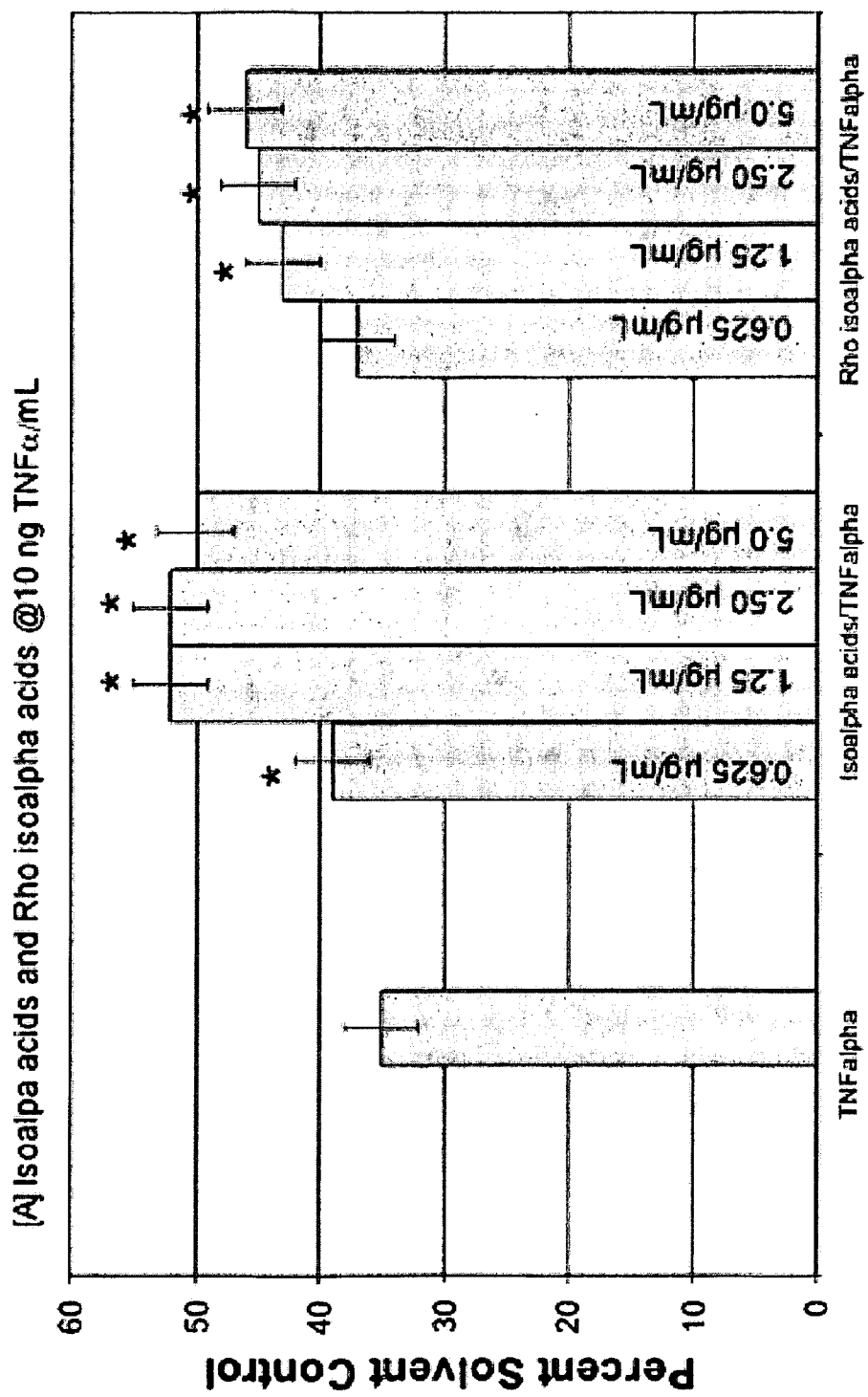
FIG. 21 displays two bar graphs representing relative adiponectin secretion by TNFα-treated, mature 3T3-L1 cells elicited by isoalpha acids and Rho isoalpha acids [panel A], and hexahydro isoalpha acids and tetrahydro isoalpha acids [panel B]. Values presented are percent relative to the solvent control; error bars represent 95% confidence intervals. *Significantly different from TNFα only treatment (p<0.05).
Figure 21B:
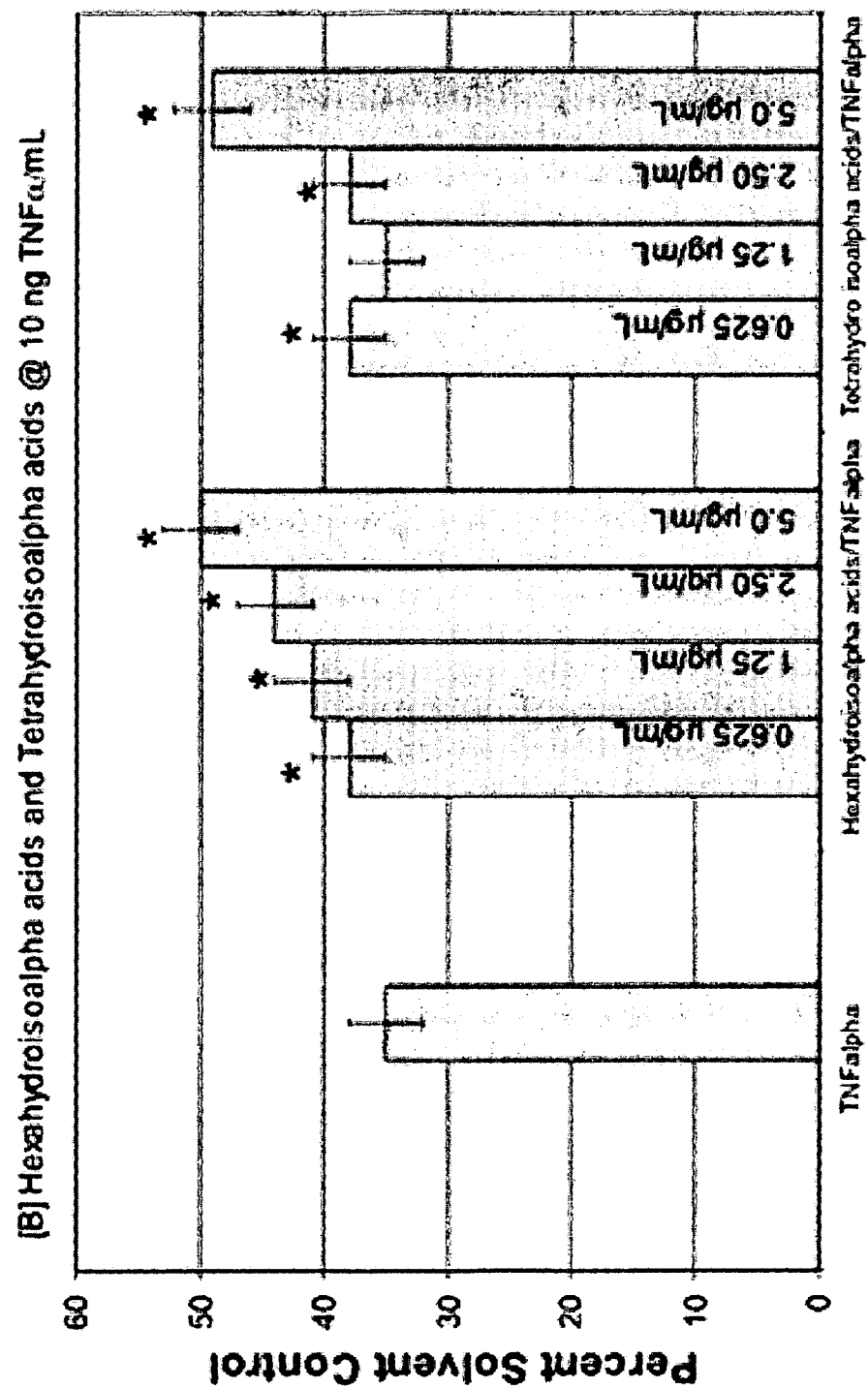

Results—Overnight treatment of D5 3T3-L1 adipocytes with 10 ng TNFα/ml markedly suppressed adiponectin secretion (FIG. 21). The hops derivatives IAA, RIAA, HHIAA and THIAA all increased adiponectin secretion relative to the TNFα/solvent control. Linear dose-response curves were observed with RIAA and HHIAA resulting in maximal inhibition at the highest concentration tested 5.0 µg/ml. IAA elicited maximal secretion of adiponectin at 1.25 µg/ml, while THIAA exhibited a curvilinear response with maximal adiponectin secretion at 5.0 µg/ml.

The ability of hops derivatives IAA, RIAA, HHIAA and THIAA to increase adipocytes adiponectin secretion in the presence of supraphysiological concentrations of TNFα supports the usefulness of these compounds in the prevention or treatment of inflammatory conditions involving suboptimal adipocyte functioning.

Example 23

Screening of Botanicals for Increased Lipogenesis in the 3T3-L1 Adipocyte Model

The Model—The 3T3-L1 murine fibroblast model as described in Example 10 was used in these experiments. Standard chemicals and statistical procedures used were as noted in Example 10.

Test Materials—The botanical products tested are described in Table 18.

Cell Culture and Treatment—Test materials were dissolved in dimethyl sulfoxide and added to achieve a concentration of 50 µg/ml at Day 0 of differentiation and maintained throughout the maturation phase (Days 6 or 7). As positive controls, indomethacin and troglitazone were added, respectively, to achieve final concentrations of 5.0 and 4.4 µg/ml. Differentiated, D6/D7 3T3-L1 cells were stained with 0.36% Oil Red O or 0.001% BODIPY.

Statistical Calculations and Interpretation—Test materials and indomethacin were assayed a minimum of three times in duplicate. Solvent and troglitazone controls were replicated eight times also in duplicate. Nonpolar lipid incorporation was represented relative to the nonpolar lipid accumulation of fully differentiated cells in the solvent controls. A positive response was defined as an increase in lipid accumulation assessed by Oil Red O or BODIPY staining greater than the respective upper 95% confidence interval of the solvent control (one-tail, Excel; Microsoft, Redmond, Wash.).

TABLE 18

Botanical products screened for lipogenic activity in the 3T3-L1 adipocyte model.

| Test Material | Source |
|---|---|
| *Momordica charantia* (Bitter Melon) | Naturex, Mamaroneck, NY |
| *Acacia catechu* sample #4909 | Kancor, Cincinnati, OH |
| *Aloe vera* | Naturex, Mamaroneck, NY |
| Germacrenes (A and D) | AM Todd, Montgomeryville, PA |
| Red raspberry seed oil | Regal Trade and Consult, Hoboken, NJ |
| *Wasabi japonica* (Wasabi) | B&D Nutritional Ingredients, Vista, CA |
| Davana oil (*Artemisia pallens*) | Kancor, Cincinnati, OH |
| *Bacopa monniera* | Suan Farma, Inc, Paramus, NJ |
| Oleoresin fennel (*Foeniculum vulgare*) | Kalsec, Kalamazoo, MI |
| *Centella asiatica* | Sabinsa, Piscataway, NJ |
| Neem (*Azadirachta indica*) | Kancor, Cincinnati, OH |
| Tea flavans (*Camellia sinensis*) | Hainan Groupforce Pharmaceutical Co. |

Results—The positive controls troglitazone and idomethacin increased nonpolar lipid incorporation, respectively, 43 and 33 percent relative to the solvent controls. All test botanical products also significantly increased nonpolar lipid incorporation at the screening concentrations of 50 or 25 µg/ml. Most active among the test materials were neem at 245 percent of controls followed by aloe vera and oleoresin fennel both at 226 percent of controls. Interestingly, while both the *Acacia catechu* and the tea sample contained flavans as putative active ingredients, the *Acacia catechu* sample at 166 percent of the solvent control was more potent in increasing triglyceride incorporation than the tea flavan sample at 133 percent (Table 19).

TABLE 19

Lipogenic activity of screened botanicals in the 3T3-L1 adipocyte model†.

| Test Material | Concentration [µg/ml] | Lipogenic Index†† [% Solvent Control] |
|---|---|---|
| *Momordica charantia* (Bitter Melon) | 50 | 173 |
| *Acacia catechu* sample #4909 | 50 | 166 |
| *Aloe vera* | 50 | 226 |
| Germacrenes (A and D) | 50 | 152 |
| Red raspberry seed oil | 50 | 162 |
| *Wasabi japonica* (Wasabi) | 50 | 174 |
| Davana oil (*Artemisia pallens*) | 25 | 153 |
| *Bacopa monniera* | 50 | 156 |
| Oleoresin fennel (*Foeniculum vulgare*) | 50 | 226 |
| *Centella asiatica* (Centellin ®) | 50 | 173 |
| Neem (*Azadirachta indica*) | 50 | 245 |
| Tea flavans (*Camellia sinensis*) | 50 | 136 |
| Indomethacin | 5.0 | 133 |
| Troglitazone | 4.4 | 143 |
| Solvent control ± 95% CI# | — | 100 ± 17 |

†All botanical products were tested a minimum of three times. Tabulated values are representative of the three independent experiments.
††Lipogenic Index = [OD]$_{Test}$/[OD]$_{DMSO\ control}$.
Lipogenic indexes >117 are significantly greater than the solvent control: least significant difference (p < 0.05) among treatments = 17.

The increased triglyceride incorporation seen in the 3T3-L1 model is an indication of the potential of the test material to increase insulin sensitivity. Physiologically, when the adipocyte pulls free fatty acids from the plasma, a concomitant loss of fat is seen in associated muscle tissue. This loss of fat in the muscle tissue results in increased sensitivity to insulin by the muscle.

Example 24

Screening of Botanicals for Increased Adiponectin Secretion in the TNFα/3T3-L1 Adipocyte Model The Model—The 3T3-L1 murine fibroblast model as described in Example 10 was used in these experiments.

Cell Culture and Treatment—Cell culture procedures, standard chemicals, adiponectin assays and statistical procedures used were as noted in Example 12. Test materials germacrenes, red raspberry seed oil, wasabi, davana oil, *Bacopa monniera*, *Centella asiatica*, and neem and were as described in Example 23. Graded doses of 50, 25, 12.5 and 6.25 μg test material/ml were prepared for all test materials except davana oil and neem. Davana oil was tested at 25, 12.5, 6.25 and 3.125 μg/ml, while concentrations for neem were 50, 10, 5 and 1 μg/ml. Concentrations for the positive control pioglitazone were 5.0, 2.5, 1.25 and 0.625 μg/ml.

Results—TNFα decreased adiponectin secretion nearly 50% relative to the DMSO control. Pioglitazone increased adiponectin secretion in the presence of TNFα by 41% at the lowest dose tested. Of the botanicals tested, only davana oil failed to significantly increase adiponectin secretion by 3T3-L1 adipocytes in the presence of TNFα. *Bacopa monniera* was most active in this assay with a 22% increase in adiponectin secretion over TNFα controls at 6.25 μg/ml (Table 20).

TABLE 20

Maximum adiponectin secretion elicited by test botanicals in the TNFα/3T3-L1 model.

| Test Material | Concentration† [μg/ml] | Adiponectin Index†† |
|---|---|---|
| DMSO control | — | 1.87 |
| TNFα control ± 95% CI | — | 1.00 ± 0.07 |
| Pioglitazone | 0.625 | 1.41* |
| Germacrenes | 6.25 | 1.14* |
| Red raspberry seed oil | 6.25 | 1.13* |
| Wasabi powder | 6.25 | 1.12* |
| Davana oil | 3.13 | 0.94 |
| *Bacopa monniera* | 6.25 | 1.22 |
| *Centella asiatica* | 6.25 | 1.12* |
| Neem | 50 | 1.19* |

The test materials or pioglitazone were added in concert with 10 ng TNFα/ml to D5 3T3-L1 adipocytes. On the following day, supernatant media were sampled for adiponectin determination. All values were indexed to the TNFα control.
†Concentration listed is that concentration for which maximum adiponectin secretion was observed.
††Adiponectin Index = [Adiponectin]$_{Test}$/[Adiponectin]$_{TNFα\ control}$
*Significantly greater than TNFα control.

The ability of germacrenes, red raspberry seed oil, wasabi powder, *Bacopa monniera*, *Centella asiatica*, and neem leaf extracts to increase adipocyte adiponectin secretion in the presence of supraphysiological concentrations of TNFα supports the usefulness of these botanical extracts and compounds for the prevention or treatment of inflammatory conditions involving suboptimal adipocyte functioning.

Example 25

*Acacia catechu* Formulation Synergistic Interaction with Hops Derivatives to Alter Lipogenesis and Adiponectin Secretion in 3T3-L1 Adipocytes The Model—The 3T3-L1 murine fibroblast model as described in Examples 10 and 12 was used in these experiments.

Test Chemicals and Treatment—Standard chemicals used were as noted in Examples 10 and 12. 3T3-L1 adipocytes were treated prior to differentiation as in Example 10 for computing the lipogenic index or with TNFα as described in Example 12 for assessing the adiponectin index. *Acacia catechu* sample #5669 as described in Example 13 was used with hops derivatives Rho-isoalpha acids and isoalpha acids as described in Example 23. *Acacia catechu* and the 5:1 and 10:1 combinations of *Acacia*:RIAA and *Acacia*:IAA were tested at 50, 10, 5.0 and 1.0 μg/ml. RIAA and IAA were tested independently at 5.0, 2.5, 1.25 and 0.625 μg/ml.

Calculations—Estimates of expected lipogenic response and adiponectin secretion of the *Acacia*/hops combinations and determination of synergy were made as described in Example 33.

Results—All combinations tested exhibited lipogenic synergy at one or more concentrations tested (Table 21). *Acacia*:RIAA combinations were generally more active than the *Acacia*:IAA combinations with *Acacia*:RIAA [5:1] demonstrating synergy at all doses and *Acacia*:RIAA [10:1] synergistic at 10 and 5.0 μg/ml and not antagonistic at any concentration tested. The *Acacia*:IAA [10:1] combination was also synergistic at the two mid-doses and showed no antagonism. While *Acacia*:IAA [5:1] was synergistic at the 50 μg/ml concentration, it was antagonistic at the 5.0 μg/ml dose.

Similarly, all combinations demonstrated synergy with respect to increasing adiponectin secretion at one or more concentrations tested (Table 22). *Acacia*:IAA [10:1] exhibited synergy at all doses, while *Acaca*:RIAA [5:1] and *Acacia*:RIAA [10:1] were synergistic at three doses and antagonistic at one concentration. The *Acacia*:IAA [5:1] combination was synergistic at 1.0 μg/ml and antagonistic at the higher 10 μg/ml.

TABLE 21

Observed and expected lipogenic response elicited by *Acacia catechu* and hops derivatives in the insulin-resistant 3T3-1 model.

| Test Material | Concentration [μg/ml] | Lipogenic Index† Observed | Expected | Result |
|---|---|---|---|---|
| *Acacia*/RIAA [5:1][1] | 50 | 1.05 | 0.98 | Synergy |
|  | 10 | 0.96 | 0.89 | Synergy |
|  | 5.0 | 0.93 | 0.90 | Synergy |
|  | 1.0 | 0.92 | 0.89 | Synergy |
| *Acacia*/IAA [5:1][2] | 50 | 1.06 | 0.98 | Synergy |
|  | 10 | 0.93 | 0.95 | No effect |
|  | 5.0 | 0.90 | 0.98 | Antagonism |
|  | 1.0 | 0.96 | 0.98 | No effect |
| *Acacia*/RIAA [10:1][3] | 50 | 0.99 | 1.03 | No effect |
|  | 10 | 1.00 | 0.90 | Synergy |
|  | 5.0 | 1.00 | 0.90 | Synergy |
|  | 1.0 | 0.94 | 0.89 | No effect |
| *Acacia*/IAA [10:1][4] | 50 | 1.37 | 1.29 | Synergy |
|  | 10 | 1.16 | 1.15 | No effect |
|  | 5.0 | 1.08 | 1.09 | No effect |
|  | 1.0 | 1.00 | 0.99 | No effect |

†Lipogenic Index = [OD]$_{Test}$/[OD]$_{DMSO\ control}$.
[1]Upper 95% confidence limit is 1.03 with least significant difference = 0.03.
[2]Upper 95% confidence limit is 1.03 with least significant difference = 0.03
[3]Upper 95% confidence limit is 1.07 with least significant difference = 0.07.
[4]Upper 95% confidence limit is 1.02 with least significant difference = 0.02.

TABLE 22

Observed and expected adiponectin secretion elicited by
Acacia catechu and hops derivatives in the TNFα/3T3-1 model.

| Test Material | Concentration [µg/ml] | Adiponectin Index† Observed | Expected | Result |
|---|---|---|---|---|
| Acacia/RIAA [5:1][1] | 50 | 1.27 | 1.08 | Synergy |
|  | 10 | 0.99 | 1.25 | Antagonism |
|  | 5.0 | 1.02 | 0.92 | Synergy |
|  | 1.0 | 1.19 | 1.07 | Synergy |
| Acacia/IAA [5:1][1] | 50 | 1.13 | 1.16 | No effect |
|  | 10 | 0.92 | 1.13 | Antagonism |
|  | 5.0 | 1.04 | 1.09 | No effect |
|  | 1.0 | 1.25 | 1.13 | Synergy |
| Acacia/RIAA [10:1][2] | 50 | 1.29 | 1.11 | Synergy |
|  | 10 | 1.07 | 0.95 | Synergy |
|  | 5.0 | 0.94 | 1.06 | Antagonism |
|  | 1.0 | 1.03 | 0.94 | Synergy |
| Acacia/IAA [10:1][2] | 50 | 1.28 | 0.82 | Synergy |
|  | 10 | 1.12 | 1.07 | Synergy |
|  | 5.0 | 1.11 | 0.99 | Synergy |
|  | 1.0 | 1.30 | 1.05 | Synergy |

†Adiponectin Index = [Adiponectin]$_{Test}$/[Adiponectin]$_{TNF\alpha\ control}$
[1]Upper 95% confidence limit is 1.07 with least significant difference = 0.07.
[2]Upper 95% confidence limit is 1.03 with least significant difference = 0.03

Combinations of *Acacia catechu* and the hops derivatives Rho isoalpha acids or isoalpha acids exhibit synergistic combinations and only few antagonistic combinations with respect to increasing lipid incorporation in adipocytes and increasing adiponectin secretion from adipocytes.

Example 26

Anti-Inflammatory Activity of Hops Derivatives in the Lipopolysaccharide/3T3-L1 Adipocyte Model The Model—The 3T3-L1 murine adipocyte model as described in Examples 10 and 12 was used in these experiments.

Test Chemicals and Treatment—Standard chemicals were as noted in Examples 10 and 12, however, 100 ng/ml of bacterial lipopolysaccharide (LPS, Sigma, St. Louis, Mo.) was used in place of TNFα on D5. Hops derivatives Rho-isoalpha acids and isoalpha acids used were as described in Example 19. The non-steroidal anti-inflammatory drugs (NSAIDs) aspirin, salicylic acid, and ibuprofen were obtained from Sigma. The commercial capsule formulation of celecoxib (Celebrex™, G.D. Searle & Co. Chicago, Ill.) was used and cells were dosed based upon content of active ingredient. Hops derivatives, ibuprofen, and celecoxib were dosed at 5.00, 2.50, 1.25 and 0.625 µg/ml. Indomethacin, troglitazone, and pioglitazone were tested at 10, 5.0, 1.0 and 0.50 µg/ml. Concentrations for aspirin were 100, 50.0, 25.0 and 12.5 µg/ml, while those for salicylic acid were 200, 100, 50.0 and 25.0 µg/ml. IL-6 and adiponectin were assayed and data were analyzed and tabulated as previously described in Example 17 for IL-6 and Example 12 for adiponectin.

Results—LPS provided a 12-fold stimulation of IL-6 in D5 adipocytes. All test agents reduced IL-6 secretion by LPS-stimulated adipocytes to varying degrees. Maximum inhibition of IL-6 and concentrations for which this maximum inhibition were observed are presented in Table 23A. Due to a relatively large within treatment variance, the extent of maximum inhibition of IL-6 did not differ among the test materials. The doses for which maximum inhibition occurred, however, did differ considerably. The rank order of potency for IL-6 inhibition was ibuprofen>RIAA=IAA>celecoxib>pioglitazone=indo methacin>troglitazone>aspirin>salicylic acid. On a qualitative basis, indomethacin, troglitazone, pioglitazone, ibuprofen and celecoxib inhibited IL-6 secretion at all concentrations tested, while RIAA, IAA, and aspirin did not significantly inhibit IL-6 at the lowest concentrations (data not shown).

LPS treatment of D5 3T3-L1 adipocytes decreased adiponectin secretion relative to the DMSO control (Table 23B). Unlike IL-6 inhibition in which all test compounds inhibited secretion to some extent, aspirin, salicylic acid and celecoxib failed to induce adiponectin secretion in LPS-treated 3T3-L1 adipocytes at any of the does tested. Maximum adiponectin stimulation of 15, 17, 20 and 22% was observed, respectively, for troglitazone, RIAA, IAA and ibuprofen at 0.625 µg/ml. Pioglitazone was next in order of potency with adiponectin stimulation of 12% at 1.25 µg/ml. With a 9% stimulation of adiponectin secretion at 2.50 µg/ml, indomethacin was least potent of the active test materials.

In the LPS/3T3-L1 model, hops derivatives RIAA and IAA as well as ibuprofen decreased IL-6 secretion and increased adiponectin secretion at concentrations likely to be obtained in vivo. The thiazolidinediones troglitazone and pioglitazone were less potent as inhibitors of IL-6 secretion, requiring higher doses than hops derivatives, but similar to hops derivatives with respect to adiponectin stimulation. No consistent relationship between anti-inflammatory activity in macrophage models and the adipocyte model was observed for the NSAIDs indomethacin, aspirin, ibuprofen and celecoxib.

TABLE 23A

Maximum inhibition of IL-6 secretion in LPS/3T3-L1 adipocytes by hops derivatives and selected NSAIDs

| Test Material | Concentration [µg/ml] | IL-6 Index† | % Inhibition |
|---|---|---|---|
| DMSO control | — | 0.09* | 91* |
| LPS control ± 95% CI | — | 1.00 ± 0.30 | 0 |
| Indomethacin | 5.00 | 0.47* | 53* |
| Troglitazone | 10.0 | 0.31* | 69* |
| Pioglitazone | 5.00 | 0.37* | 63* |
| Rho-isoalpha acids | 1.25 | 0.63* | 37* |
| Isoalpha acids | 1.25 | 0.61* | 39* |
| Aspirin | 25.0 | 0.61* | 39* |
| Salicylic acid | 50.0 | 0.52* | 48* |
| Ibuprofen | 0.625 | 0.46* | 54* |
| Celecoxib | 2.50 | 0.39* | 61* |

The test materials were added in concert with 100 ng LPS/ml to D5 3T3-L1 adipocytes. On the following day, supernatant media were sampled for IL-6 determination. All values were indexed to the LPS control as noted below. Concentrations presented represent dose providing the maximum inhibition of IL-6 secretion and those values less than 0.70 are significantly (p < 0.05) less than the LPS control.
†IL-6 Index = [IL-6$_{Test}$ − IL-6$_{Control}$]/[IL-6$_{LPS}$ − IL-6$_{Control}$]
*Significantly different from LPS control p < 0.05).

TABLE 23B

Maximum stimulation of adiponectin secretion in LPS/3T3-L1 adipocytes by hops derivatives and selected NSAIDs

| Test Material | Concentration [µg/ml] | Adiponectin Index† | % Stimulation |
|---|---|---|---|
| DMSO control | — | 1.24 |  |
| LPS control ± 95% CI | — | 1.00 |  |
| Indomethacin | 2.50 | 1.09* | 9 |
| Troglitazone | 0.625 | 1.15* | 15 |
| Pioglitazone | 1.25 | 1.12* | 12 |
| Rho-isoalpha acids | 0.625 | 1.17* | 17 |
| Isoalpha acids | 0.625 | 1.20* | 20 |
| Aspirin | 113 | 1.02 | NS |

TABLE 23B-continued

Maximum stimulation of adiponectin secretion in LPS/3T3-L1 adipocytes by hops derivatives and selected NSAIDs

| Test Material | Concentration [µg/ml] | Adiponectin Index† | % Stimulation |
|---|---|---|---|
| Salicylic acid | 173 | 0.96 | NS |
| Ibuprofen | 0.625 | 1.22* | 22 |
| Celecoxib | 5.00 | 1.05 | NS |

†Adiponectin Index = [Adiponectin]$_{Test}$/[Adiponectin]$_{LPS\ control}$
*Values greater than 1.07 are significantly different from LPS control p < 0.05).
NS = not significantly different from the LPS control.

Example 27

In Vitro Synergy of Lipogenesis by Hops Derivatives in Combination with Hypoglycemic Botanicals in the 3T3-L1 Adipocyte Model The Model—The 3T3-L1 murine fibroblast model as described in Example 10 was used in these experiments. Standard chemicals and statistical procedures used were as noted, respectively in Examples 10 and 33.

Test Materials and Treatment—Curcumin was obtained from Sabinsa (Piscataway, N.J.) and the hypoglycemic botanical products tested were as described in Example 16 Table 12. Rho isoalpha acids and isoalpha acids used were as described in Example 19. The botanical products were tested at 50, 10, 5.0 and 1.0 µg/ml individually and in 5:1 combinations with RIAA or IAA at the same concentrations. RIAA and IAA were tested independently at 5.0, 2.5, 1.25 and 0.625 µg/ml for calculation of expected lipogenic index as described in Example 33.

Results—Both RIAA and IAA exhibited synergy with all four of the hypoglycemic botanicals tested (Table 24). The bitter melon:RIAA and IAA mixtures were synergistic at three of the four concentrations tested. The hops derivatives differed in the dose lacking synergy with bitter melon in that RIAA was ineffective at the lowest dose and the bitter melon:IAA combination was not synergistic at the highest concentration tested. A somewhat similar response was observed for aloe vera:hops combinations, differing only in that the aloe vera:RIAA combination at 5.0 µg/ml also demonstrated no effect. The neem:RIAA combination was synergistic at one concentration (10 µg/ml) and the neem:IAA combinations increased lipogenesis synergistically at three of the four doses. Curcumin:RIAA mixtures exhibited synergy at the two lowest doses, while curcumin:IAA combinations were synergistic at three doses and strongly antagonistic at the highest concentration.

Combinations of RIAA or IAA with bitter melon, aloe vera, neem or curcumin exhibited synergistic increases in lipogenesis in insulin-resistant 3T3-L1 adipocytes over a range of concentrations with antagonism observed only at the highest concentration of the curcumin:IAA mixture.

TABLE 24

Synergy of lipogenesis by hops derivatives in combination with hypoglycemic botanicals in the insulin-resistant 3T3-L1 adipocyte model.

| Test Material | Concentration [µg/ml] | Lipogenic Index† Observed | Lipogenic Index† Expected | Interpretation |
|---|---|---|---|---|
| Bitter Melon/RIAA [5:1][1] | 50 | 1.19 | 0.85 | Synergy |
| | 10 | 1.05 | 0.96 | Synergy |
| | 5.0 | 1.05 | 1.00 | Synergy |
| | 1.0 | 1.04 | 1.02 | No effect |
| Bitter Melon/IAA [5:1][2] | 50 | 0.79 | 0.79 | No effect |
| | 10 | 1.06 | 0.94 | Synergy |
| | 5.0 | 0.99 | 0.94 | Synergy |
| | 1.0 | 0.95 | 0.92 | Synergy |
| Aloe vera/RIAA [5:1][3] | 50 | 1.30 | 1.03 | Synergy |
| | 10 | 1.06 | 1.03 | Synergy |
| | 5.0 | 1.00 | 1.00 | No effect |
| | 1.0 | 1.10 | 1.10 | No effect |
| Aloe vera/IAA [5:1][4] | 50 | 0.96 | 0.99 | No effect |
| | 10 | 1.20 | 1.02 | Synergy |
| | 5.0 | 1.18 | 1.08 | Synergy |
| | 1.0 | 1.14 | 1.07 | Synergy |
| Neem/RIAA [5:1][5] | 50 | 1.18 | 1.21 | No effect |
| | 10 | 1.22 | 1.02 | Synergy |
| | 5.0 | 1.06 | 1.06 | No effect |
| | 1.0 | 0.89 | 0.91 | No effect |
| Neem/IAA [5:1][6] | 50 | 1.24 | 1.18 | Synergy |
| | 10 | 1.25 | 1.15 | Synergy |
| | 5.0 | 111 | 1.11 | No effect |
| | 1.0 | 1.08 | 1.04 | Synergy |
| Curcumin/RIAA [1:1][7] | 10 | 0.47 | 0.52 | No effect |
| | 5.0 | 0.82 | 0.86 | No effect |
| | 1.0 | 1.11 | 1.07 | Synergy |
| | 0.5 | 1.08 | 1.01 | Synergy |
| Curcumin/IAA [1:1][8] | 10 | 0.27 | 0.84 | Antagonism |
| | 5.0 | 1.19 | 0.90 | Synergy |
| | 1.0 | 1.27 | 1.10 | Synergy |
| | 0.5 | 1.20 | 0.93 | Synergy |

†Lipogenic Index = [OD]$_{Test}$/[OD]$_{DMSO\ control}$.
[1]Upper 95% confidence limit is 1.03 with least significant difference = 0.03.
[2]Upper 95% confidence limit is 1.01 with least significant difference = 0.01.
[3]Upper 95% confidence limit is 1.01 with least significant difference = 0.01.
[4]Upper 95% confidence limit is 1.01 with least significant difference = 0.01.
[5]Upper 95% confidence limit is 1.03 with least significant difference = 0.03.
[6]Upper 95% confidence limit is 1.01 with least significant difference = 0.01.
[7]Upper 95% confidence limit is 1.02 with least significant difference = 0.02.
[8]Upper 95% confidence limit is 1.01 with least significant difference = 0.01.

Example 28

In Vitro Synergy of Lipogenesis by Rho Isoalpha Acids in Combination with Botanicals in the Insulin-Resistant 3T3-L1 Adipocyte Model The Model—The 3T3-L1 murine fibroblast model as described in Examples 10 and 12 was used in these experiments.

Test Chemicals and Treatment—Standard chemicals used were as noted in Example 1. 3T3-L1 adipocytes were treated prior to differentiation as in Example 10 for computing the lipogenic index. Botanical samples as described in Example 24 Table 18 were used in combination with hops derivative Rho-isoalpha acids as described in Example 19. Botanical samples, RIAA and the 5:1 combinations of botanical:RIAA were tested at 50, 10, 5.0 and 1.0 µg/ml. RIAA was tested independently at 5.0, 2.5, 1.25 and 0.625 µg/ml for calculation of expected lipogenic index as described in Example 33.

Results—RIAA synergistically increased triglyceride content in combination with each of the botanicals. Synergy was noted at all does with wasabi, at the three lower doses with Centella asiatica, at the two higher doses with germacrenes and red raspberry seed oil, and at only the highest dose with oleoresin fennel (Table 25).

Synergy between the hops derivative and botanicals was observed over a wide range of doses and potentially could be used to increase the insulin sensitizing potency of botanicals.

TABLE 25

Synergy of lipogenesis by Rho-isoalpha acids in combination with screened botanicals in the insulin-resistant 3T3-L1 adipocyte model.

| Test Material | Concentration [µg/ml] | Lipogenic Index† Observed | Expected | Interpretation |
|---|---|---|---|---|
| Germacrenes/RIAA [5:1][1] | 50 | 1.10 | 1.00 | Synergy |
| | 10 | 1.02 | 0.99 | Synergy |
| | 5.0 | 1.00 | 1.06 | Antagonism |
| | 1.0 | 0.96 | 1.02 | Antagonism |
| Red Raspberry Seed Oil/RIAA [5:1][2] | 50 | 1.14 | 1.04 | Synergy |
| | 10 | 1.07 | 1.04 | Synergy |
| | 5.0 | 1.04 | 1.02 | No effect |
| | 1.0 | 1.00 | 0.96 | No effect |
| Wasabi/RIAA [5:1][3] | 50 | 1.09 | 0.99 | Synergy |
| | 10 | 1.08 | 0.94 | Synergy |
| | 5.0 | 1.06 | 0.96 | Synergy |
| | 1.0 | 1.01 | 0.95 | Synergy |
| Oleoresin fennel/RIAA [5:1][4] | 50 | 1.42 | 1.09 | Synergy |
| | 10 | 1.11 | 1.14 | Antagonism |
| | 5.0 | 1.12 | 1.25 | Antagonism |
| | 1.0 | 1.06 | 1.17 | Antagonism |
| *Centella asiatica*/RIAA [5:1][5] | 50 | 1.10 | 1.10 | No effect |
| | 10 | 1.16 | 0.99 | Synergy |
| | 5.0 | 1.11 | 0.96 | Synergy |
| | 1.0 | 1.05 | 0.92 | Synergy |

†Lipogenic Index = $[OD]_{Test}/[OD]_{DMSO\ control}$.
[1]Upper 95% confidence limit is 1.01 with least significant difference = 0.01.
[2]Upper 95% confidence limit is 1.04 with least significant difference = 0.04.
[3]Upper 95% confidence limit is 1.02 with least significant difference = 0.02.
[4]Upper 95% confidence limit is 1.02 with least significant difference = 0.02.
[5]Upper 95% confidence limit is 1.03 with least significant difference = 0.03.

Example 29

Synergy of *Acacia catechu* or Hops Derivatives in Combination with Curcumin or Xanthohumols in the TNFα/3T3-1 Model The Model—The 3T3-L1 murine fibroblast model as described in Examples 10 and 12 was used in these experiments.

Test Chemicals and Treatment—Standard chemicals used were as noted in Example 10 and 12. 3T3-L1 adipocytes were stimulated with TNFα as described in Example 12 for assessing the adiponectin index. *Acacia catechu* sample #5669 as described in Example 13, hops derivatives Rho-isoalpha acids and xanthohumol as described in Example 19, and curcumin as described in Example 27 and were used in these experiments. *Acacia catechu* and the 5:1 combinations of *Acacia*:curcumin and *Acacia*:xanthohumol were tested at 50, 10, 5.0 and 1.0 µg/ml. RIAA and the 1:1 combinations with curcumin and XN were tested at 10, 5, 1.0 and 0.50 µg/ml.

Calculations—Estimates of expected adiponectin index of the combinations and determination of synergy were made as described in Example 33.

Results—TNFα reduced adiponectin secretion to about 50 percent of solvent only controls. The positive control pioglitazone increased adiponectin secretion by 80 percent (Table 26). Combinations of *Acacia* with curcumin or XN proved to be antagonistic at the higher concentrations and synergistic at the lower concentrations. Similarly, RIAA and curcumin were antagonistic at the three higher doses, but highly synergistic at the lowest dose 1.0 µg/ml. The two hops derivative RIAA and XN did not demonstrate synergy in adiponectin secretion from TNFα-stimulated 3T3-L1 cells.

In TNFα-treated 3T3-L1 adipocytes, both *Acacia* and RIAA synergistically increased adiponectin secretion, while only *Acacia* demonstrated synergy with XN.

TABLE 26

Synergy of *Acacia catechu* and hops derivatives in combinations with curcumin or xanthohumols in the TNFα/3T3-1 model.

| Test Material | Concentration [µg/ml] | Adiponectin Index† Observed | Expected | Interpretation |
|---|---|---|---|---|
| DMSO Control | — | 2.07 | — | — |
| TNFα ± 95% CI | — | 1.0 ± 0.049 | — | — |
| Pioglitazone | 1.0 | 1.80 | — | — |
| *Acacia*/Curcumin [5:1][1] | 50 | 0.56 | 0.94 | Antagonism |
| | 10 | 1.01 | 1.07 | Antagonism |
| | 5.0 | 1.19 | 1.02 | Synergy |
| | 1.0 | 1.22 | 1.16 | Synergy |
| *Acacia*/XN [5:1][1] | 50 | 0.54 | 0.85 | Antagonism |
| | 10 | 0.95 | 1.06 | Antagonism |
| | 5.0 | 0.97 | 1.01 | Antagonism |
| | 1.0 | 1.26 | 1.15 | Synergy |

TABLE 26-continued

Synergy of *Acacia catechu* and hops derivatives in combinations with curcumin or xanthohumols in the TNFα/3T3-1 model.

| Test Material | Concentration [μg/ml] | Adiponectin Index† | | Interpretation |
|---|---|---|---|---|
| | | Observed | Expected | |
| RIAA/Curcumin [1:1][1] | 5 | 0.46 | 0.79 | Antagonism |
| | 1 | 1.03 | 1.11 | Antagonism |
| | 5.0 | 1.12 | 1.28 | Antagonism |
| | 1.0 | 1.30 | 1.08 | Synergy |
| RIAA/XN [1:1][1] | 50 | 0.31 | 0.63 | Antagonism |
| | 10 | 0.81 | 1.06 | Antagonism |
| | 5.0 | 1.09 | 1.25 | Antagonism |
| | 1.0 | 1.09 | 1.06 | No effect |

†Adiponectin Index = [Adiponectin]$_{Test}$/[Adiponectin]$_{TNF\alpha\ control}$
[1] 95% confidence limits are 0.961 to 1.049 with least significant difference = 0.049.

Example 30

In Vitro Synergy of Lipogenesis by *Acacia catechu* in Combination with Botanicals in the Insulin-Resistant 3T3-L1 Adipocyte Model The Model—The 3T3-L1 murine fibroblast model as described in Examples 10 and 12 was used in these experiments.

Test Chemicals and Treatment—Standard chemicals used were as noted in Example 10. 3T3-L1 adipocytes were treated prior to differentiation as in Example 10 for computing the lipogenic index. Botanical samples as described in Example 24 Table 18 were used in combination with *Acacia catechu* sample #5669 as described in Example 13. Botanical samples, *Acacia catechu* and the 1:1 combinations of botanical:*Acacia catechu* were tested at 50, 10, and 5.0 μg/ml. Botanical samples and *Acacia catechu* were also tested independently at 50, 10, and 5.0 μg/ml for calculation of expected lipogenic index as described in Example 13.

Results—*Acacia catechu* synergistically increased triglyceride content in combination with both Germacrenes and *Centella asiatica*. Synergy was noted at all doses (Table 27).

Synergy between *Acacia catechu* and botanicals was observed over a wide range of doses and potentially could be used to increase the insulin sensitizing potency of botanicals.

TABLE 27

Synergy of lipogenesis by *Acacia catechu* in combination with screened botanicals in the insulin-resistant 3T3-L1 adipocyte model.

| Test Material | Concentration [μg/ml] | Lipogenic Index† | | Interpretation |
|---|---|---|---|---|
| | | Observed | Expected | |
| Germacrenes/ *Acacia catechu* [1:1][1] | 50 | 1.25 | 1.10 | Synergy |
| | 10 | 1.08 | 1.01 | Synergy |
| | 5.0 | 1.07 | 1.04 | Synergy |
| *Centella asiatica*/ *Acacia catechu* [1:1][2] | 50 | 1.18 | 1.08 | Synergy |
| | 10 | 1.07 | 1.01 | Synergy |
| | 5.0 | 1.06 | 0.99 | Synergy |

†Lipogenic Index = [OD]$_{Test}$/[OD]$_{DMSo\ control}$.
[1] Upper 95% confidence limit is 1.01 with least significant difference = 0.01.
[2] Upper 95% confidence limit is 1.03 with least significant difference = 0.03.

Example 31

In Vitro Synergy of Lipogenesis by Conjugated Linoleic Acid in Combination with Hops Derivative Rho-Isoalpha Acids in the Insulin-Resistant 3T3-L1 Adipocyte Model The Model—The 3T3-L1 murine fibroblast model as described in Examples 10 and 12 was used in these experiments.

Test Chemicals and Treatment—Standard chemicals used were as noted in Example 10. 3T3-L1 adipocytes were treated prior to differentiation as in Example 10 for computing the lipogenic index. Powdered CLA was obtained from Lipid Nutrition (Channahon, Ill.) and was described as a 1:1 mixture of the c9t11 t10c12 isomers. CLA and the 5:1 combinations of CLA:RIAA were tested at 50, 10, 5.0 and 1.0 μg/ml. RIAA was tested at 10, 1.0 and 0.1 μg/ml for calculation of expected lipogenic index as described in Example 33.

Results—RIAA synergistically increased triglyceride content in combination with CLA. Synergy was noted at all does (Table 28).

Synergy between CLA and RIAA was observed over a wide range of doses and potentially could be used to increase the insulin sensitizing potency of CLA.

TABLE 28

Synergy of lipogenesis by conjugated linoleic acid in combination Rho-isoalpha acids in the insulin-resistant 3T3-L1 adipocyte model.

| Test Material | Concentration [μg/ml] | Lipogenic Index† | | Interpretation |
|---|---|---|---|---|
| | | Observed | Expected | |
| CLA: RIAA[5:1][1] | 50 | 1.26 | 1.15 | Synergy |
| | 10 | 1.16 | 1.06 | Synerg |
| | 5.0 | 1.16 | 1.10 | Synergy |
| | 1.0 | 1.17 | 1.06 | Synergy |

†Lipogenic Index = [OD]$_{Test}$/[OD]$_{DMSO\ control}$.
[1] Upper 95% confidence limit is 1.05 with least significant difference = 0.05.

Example 32

Hops Phytochemicals Inhibit NF-kB Activation in TNFα-Treated 3T3-L1 Adipocytes The Model—The 3T3-L1 murine fibroblast model as described in Example 10 was used in these experiments.

Cell Culture and Treatment—Following differentiation 3T3-L1 adipocytes were maintained in post-differentiation medium for an additional 40 days. Standard chemicals, media and hops compounds RIAA and xanthohumol were as described in Examples 12 and 19. Hops derivatives and the positive control pioglitazone were tested at concentrations of 2.5, and 5.0 µg/ml. Test materials were added 1 hour prior to and nuclear extracts were prepared three and 24 hours following treatment with TNFα.

ELISA—3T3-L1 adipocytes were maintained in growth media for 40 days following differentiation. Nuclear NF-kBp65 was determined using the TransAM™ NF-kB kit from Active Motif (Carlsbad, Calif.) was used with no modifications. Jurkat nuclear extracts provided in the kit were derived from cells cultured in medium supplemented with 50 ng/ml TPA (phorbol, 12-myristate, 13 acetate) and 0.5 µM calcium ionophore A23187 for two hours at 37° C. immediately prior to harvesting.

Protein assay—Nuclear protein was quantified using the Active Motif Fluorescent Protein Quantificantion Kit.

Statistical Analysis—Comparisons were performed using a one-tailed Student's t-test. The probability of a type I error was set at the nominal five percent level.

Figure 22A:
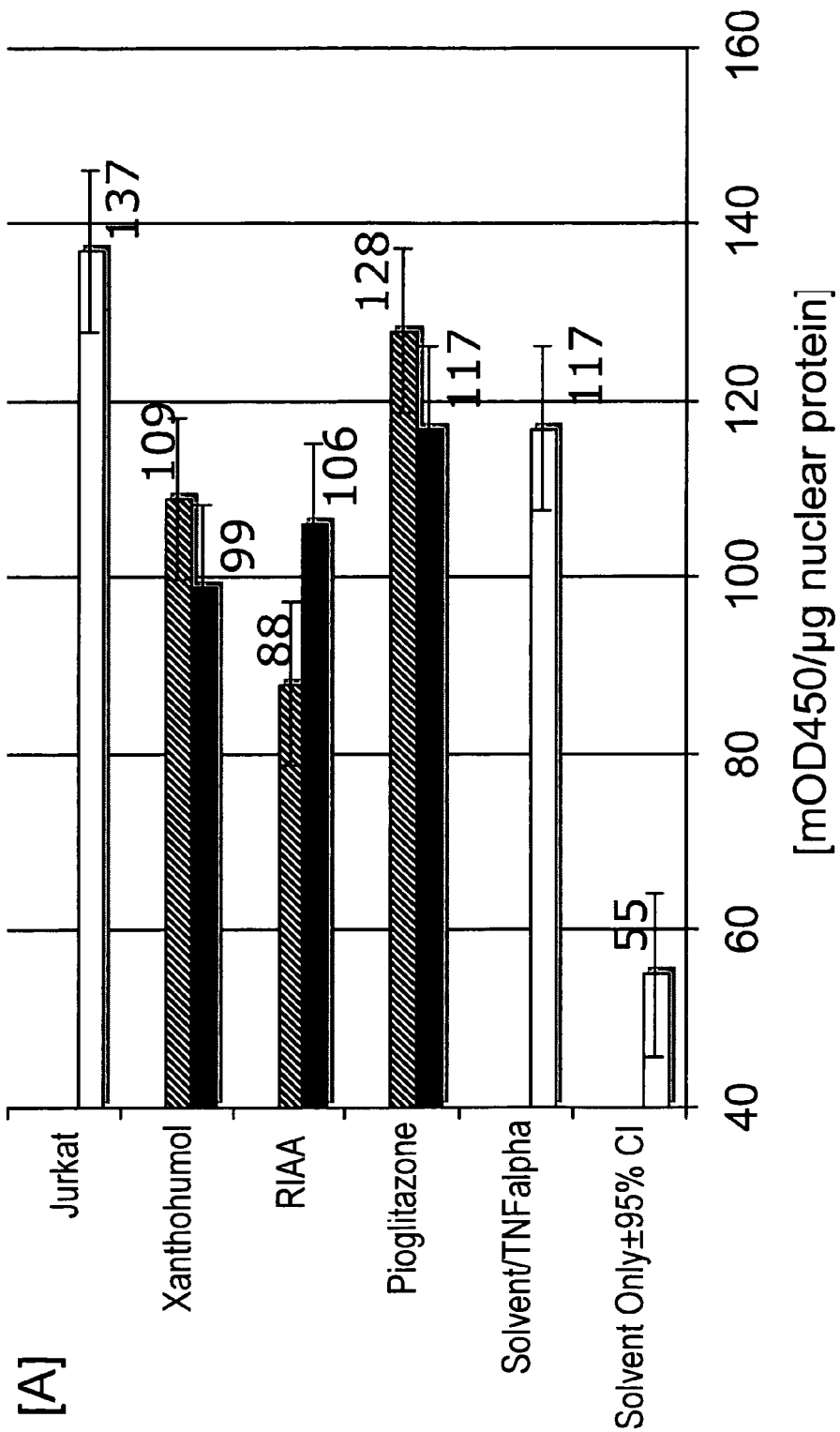
FIG. 22 depicts NF-kB nuclear translocation in insulin-resistant 3T3-L1 adipocytes [panel A] three and [panel B] 24 hr following addition of 10 ng TNFα/ml. Pioglitazone, RIAA and xanthohumols were added at 5.0 (black bars) and 2.5 (stripped bars) μg/ml. Jurkat nuclear extracts from cells cultured in medium supplemented with 50 ng/ml TPA (phorbol, 12-myristate, 13 acetate) and 0.5 μM calcium ionophore A23187 (CI) for two hours at 37° C. immediately prior to harvesting.
Figure 22B:
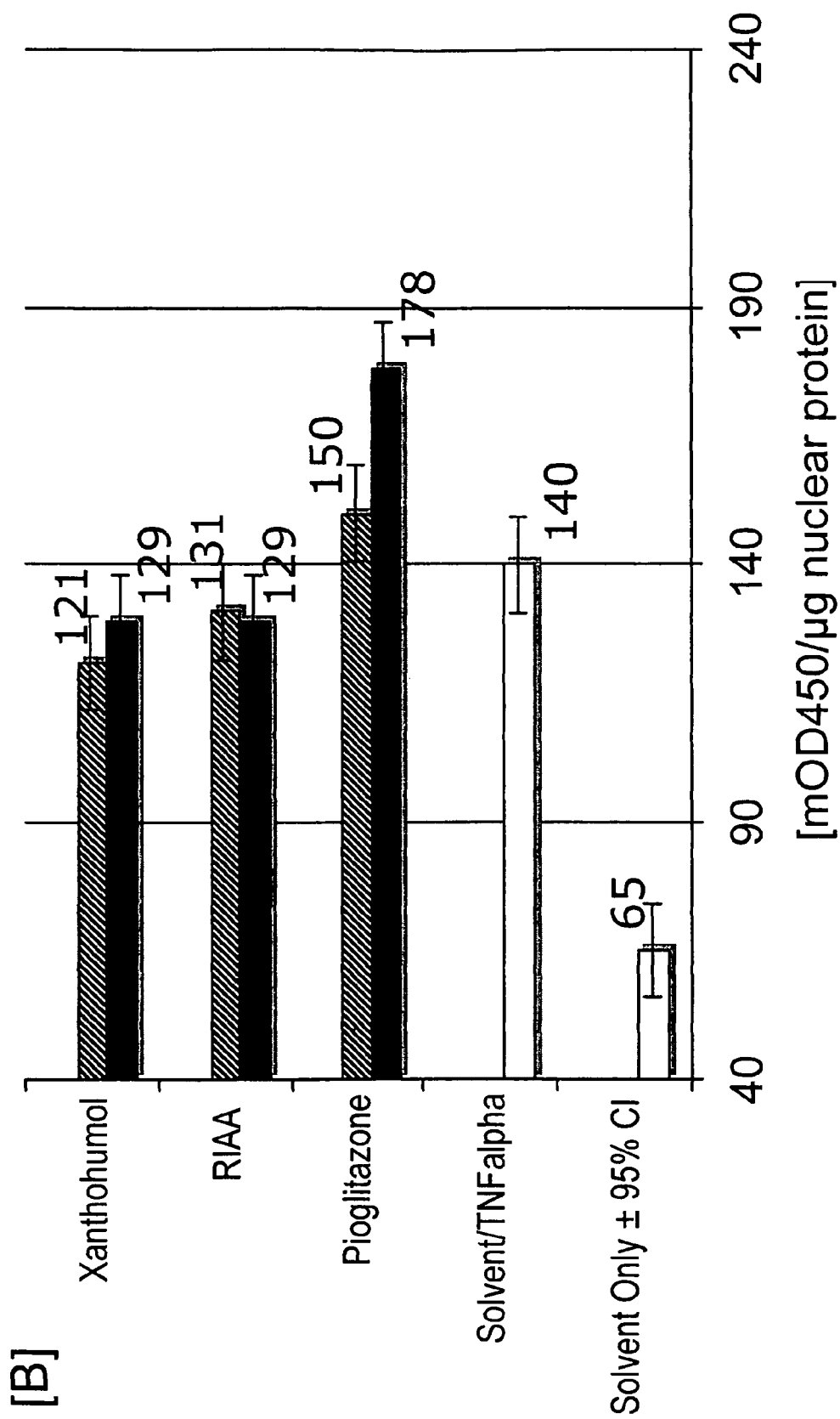

Results—The TPA-treated Jurkat nuclear extract exhibited the expected increase in NF-kBp65 indicating adequate performance of kit reagents (FIG. 22). Treatment of D40 3T3-L1 adipocytes with 10 ng TNFα/ml for three (FIG. 22A) or 24 hours (FIG. 22B), respectively, increased nuclear NF-kBp65 2.1- and 2.2-fold. As expected, the PPARγ agonist pioglitazone did not inhibit the amount of nuclear NF-kBp65 at either three or 24 hours following TNFα treatment. Nuclear translocation of NF-kBp65 was inhibited, respectively, 9.4 and 25% at 5.0 and 2.5 µg RIAA/ml at three hours post TNFα. At 24 hours, only the 5.0 RIAA/ml treatment exhibited significant ($p<0.05$) inhibition of NF-kBp65 nuclear translocation. Xanthohumols inhibited nuclear translocation of NF-kBp65, respectively, 15.6 and 6.9% at 5.0 and 2.5 µg/ml at three hours post-TNFα treatment and 13.4 and 8.0% at 24 hours.

Both RIAA and xanthohumols demonstrated consistent, albeit small, inhibition of nuclear translocation of NF-kBp65 in mature, insulin-resistant adipocytes treated with TNFα. This result differs from PPARγ agonists, which have not been shown to inhibit nuclear translocation of NF-kBp65 in 3T3-L1 adipocytes.

Example 33

*Acacia catechu* Extract and Metformin Synergistically Increase Triglyceride Incorporation in Insulin Resistant 3T3-L1 Adipocytes The Model—The 3T3-L1 murine fibroblast model as described in Example 10 was used in these experiments. All chemicals and procedures used were as described in Example 10.

Test Chemicals and Treatment—Metformin was obtained from Sigma (St. Louis, Mo.). Test materials were added in dimethyl sulfoxide at Day 0 of differentiation and every two days throughout the maturation phase (Day 6/7). As a positive control, troglitazone was added to achieve a final concentration of 4.4 µg/ml. Metformin, *Acacia catechu* sample #5669 and the metformin/Acacia combination of 1:1 were tested at 50 µg test material/ml. Differentiated 3T3-L1 cells were stained with 0.2% Oil Red O. The resulting stained oil droplets were dissolved with isopropanol and quantified by spectrophotometric analysis at 530 nm. Results were represented as a relative triglyceride content of fully differentiated cells in the solvent controls.

Calculations—An estimate of the expected adipogenic effect of the metformin/*Acacia catechu* extract was made using the relationship: $1/LI=X/LIx+Y/LIy$, where LI=the lipogenic index, X and Y were the relative fractions of each component in the test mixture and $X+Y=1$. Synergy was inferred if the mean of the estimated LI fell outside of the 95% confidence interval of the estimate of the corresponding observed fraction. This definition of synergy, involving comparison of the effects of a combination with that of each of its components, was described by Berenbaum [Berenbaum, M. C. What is synergy? Pharmacol Rev 41(2), 93-141, (1989)].

Figure 23:
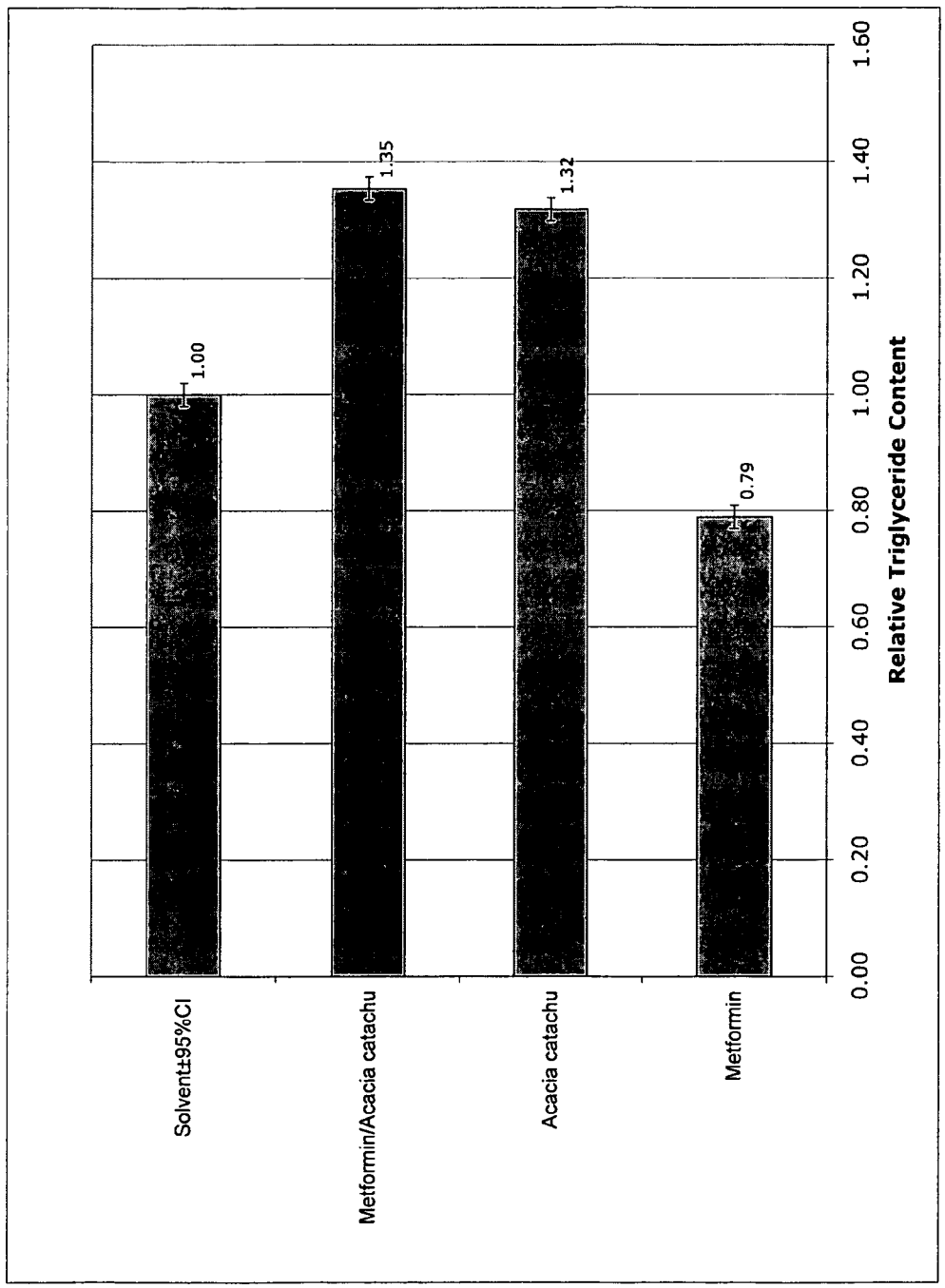
FIG. 23 graphically describes the relative triglyceride content of insulin resistant 3T3-L1 cells treated with solvent, metformin, an *Acacia* sample #5659 aqueous extract or a 1:1 combination of metformin/*Acacia catechu* extract. Results are represented as a relative triglyceride content of fully differentiated cells in the solvent controls.

Results—The *Acacia catechu* extract was highly lipogenic, increasing triglyceride content of the 3T3-L1 cells by 32 percent (FIG. 23) yielding a lipogenic index of 1.32. With a lipogenic index of 0.79, metformin alone was not lipogenic. The metformin/*Acacia catechu* extract combination demonstrated an observed lipogenic index of 1.35. With an expected lipogenic index of 98, the metformin/*Acacia catechu* extract demonstrated synergy as the observed lipogenic index fell outside of the two percent 95% upper confidence limit for the expected value.

Based upon the lipogenic potential demonstrated in 3T3-L1 cells, 1:1 combinations of metformin and *Acacia catechu* extract would be expected to behave synergistically in clinical use. Such combinations would be useful to increase the range of positive benefits of metformin therapy such as decreasing plasma triglycerides or extending the period of metformin efficacy.

Example 34

In Vitro Synergies of Lipogenesis by Hops Derivatives and Thiazolidinediones in the Insulin-Resistant 3T3-L1 Adipocyte Model The Model—The 3T3-L1 murine fibroblast model as described in Examples 10 and 12 was used in these experiments.

Test Chemicals and Treatment—Standard chemicals used were as noted in Example 10. 3T3-L1 adipocytes were treated prior to differentiation as in Example 10 for computing the lipogenic index. Troglitazone was obtained from Cayman Chemicals (Chicago, Ill.). Pioglitazone was obtained as the commercial, tableted formulation (ACTOSE®, Takeda Pharmaceuticals, Lincolnshire, Ill.). The tablets were crushed and the whole powder was used in the assay. All results were computed based upon active ingredient content. Hops derivatives Rho-isoalpha acids and isoalpha acids used were as described in Example 19. Troglitazone in combination with RIAA and IAA was tested at 4.0 µg/ml, while the more potent pioglitazone was tested in 1:1 combinations with RIAA and IAA at 2.5 µg/ml. All materials were also tested independently at 4.0 and 2.5 µg/ml for calculation of expected lipogenic index as described in Example 33.

Results—When tested at 4.0 and 2.5 µg/ml, respectively, with troglitazone or proglitazone, both Rho-isoalpha acids and isoalpha acids increased triglyceride synthesis synergistically with the thiazolidinediones in the insulin-resistant 3T3-L1 adipocyte model (Table 29).

Hops derivatives Rho-isoalpha acids and isoalpha acids could synergistically increase the insulin sensitizing effects of thiazolidinediones resulting in potential clinical benefits of dose-reduction or increased numbers of patients responding favorably.

TABLE 29

In vitro synergies of hops derivatives and thiazolidinediones in the insulin-resistant 3T3-L1 adipocyte model.

| Test Material | Concentration [μg/ml] | Lipogenic Index† Observed | Expected | Interpretation |
|---|---|---|---|---|
| Troglitazone/RIAA [1:1][1] | 4.0 | 1.23 | 1.06 | Synergy |
| Troglitazone/IAA [1:1][1] | 4.0 | 1.14 | 1.02 | Synergy |
| Pioglitazone/RIAA [1:1][2] | 2.5 | 1.19 | 1.00 | Synergy |
| Pioglitazone/IAA [1:1][2] | 2.5 | 1.16 | 0.95 | Synergy |

†Lipogenic Index = $[OD]_{Test}/[OD]_{DMSO\ control}$.
[1]Upper 95% confidence limit is 1.02 with least significant difference = 0.02.
[2]Upper 95% confidence limit is 1.05 with least significant difference = 0.05.

Results—TNFα provided a six-fold increase in IL-6 secretion in D5 adipocytes. Troglitazone at 1 μg/ml inhibited IL-6 secretion 34 percent relative to the controls, while 1 μg RIAA inhibited IL-6 secretion 24 percent relative to the controls (Table 30). Metformin in combination with 1 μg RIAA/ml demonstrated synergy at the 50 μg/ml concentration and strong synergy at the 1 μg/ml concentration. At 50 μg metformin/ml, 1 μg RIAA provided an additional 10 percent inhibition in the mixture; while at 1 μg metformin, 1 μg RIAA increased IL-6 inhibition by 35 percent. Antagonism and no effect, respectively, were seen of the metformin:RIAA combinations at the two mid-doses.

Combinations of metformin and Rho-isoalpha acids function synergistically at both high and low concentrations to reduce IL-6 secretion from TNFα-treated 3T3-L1 adipocytes.

TABLE 30

Synergistic inhibition of IL-6 secretion in TNFα/3T3-L1 adipocytes by hops Rho-isoalpha acids and metformin.

| Test Material | Concentration [μg/ml] | IL-6 Index† | % Inhibition | Interpretation |
|---|---|---|---|---|
| DMSO control | — | 0.16 | — | — |
| TNFα control ± 95% CI | — | 1.00 ± 0.07* | 0 | — |
| Troglitazone | 1.0 | 0.66 | 34 | — |
| RIAA | 1.0 | 0.76 | 24 | — |
| Metformin | 50 | 0.78 | 22 | — |
| Metformin/1 μg RIAA | 50 | 0.68 | 32 | Synergy |
| Metformin | 10 | 0.78 | 22 | — |
| Metformin/1 μg RIAA | 10 | 0.86 | 14 | Antagonism |
| Metformin | 5.0 | 0.96 | 4 | — |
| Metformin/1 μg RIAA | 5.0 | 0.91 | 9 | No effect |
| Metformin | 1.0 | 0.91 | 9 | — |
| Metformin/1 μg RIAA | 1.0 | 0.56 | 44 | Synergy |

The test materials were added in concert with 10 ng TNFα/ml to D5 3T3-L1 adipocytes at the stated concentrations. On the following day, supernatant media were sampled for IL-6 determination. All values were indexed to the TNFα control.
†IL-6 Index = $[IL\text{-}6_{Test} - IL\text{-}6_{Control}]/[IL\text{-}6_{TNF\alpha} - IL\text{-}6_{Control}]$
*Values less than 0.93 are significantly (p < 0.05) less than the TNFα control.

Example 35

In Vitro Synergies of Rho-Isoalpha Acids and Metformin in the TNFα/3T3-L1 Adipocyte Model The Model—The 3T3-L1 murine fibroblast model as described in Example 10 was used in these experiments. Standard chemicals used and treatment of adipocytes with 10 ng TNFα/ml were as noted, respectively, in Examples 10 and 12.

Test Materials and Cell Treatment—Metformin was obtained from Sigma (St. Louis, Mo.) and Rho-isoalpha acids were as described in Example 19. Metformin at 50, 10, 5.0 or 1.0 μg/ml without or with 1 μg RIAA/ml was added in concert with 10 ng TNFα/ml to D5 3T3-L1 adipocytes. Culture supernatant media were assayed for IL-6 on Day 6 as detailed in Example 17. An estimate of the expected effect of the metformin:RIAA mixtures on IL-6 inhibition was made as previously described in Example 33.

Example 36

In Vivo Hypoglycemic Action of *Acacia nilotica* and Hops Derivatives in the KK-A$^y$ Mouse Diabetes Model The Model—Male, nine-week old KK-A$^y$/Ta mice averaging 40±5 grams were used to assess the potential of the test materials to reduce fasting serum glucose or insulin concentrations. This mouse strain is the result of hybridization between the KK strain, developed in the 1940s as a model of diabetes and a strain of A$^y$/a genotype. The observed phenotype is the result of polygenic mutations that have yet to be fully characterized but at least four quantitative trait loci have been identified. One of these is linked to a missense mutation in the leptin receptor. Despite this mutation the receptor remains functional although it may not be fully efficient. The KK strain develops diabetes associated with insensitivity to insulin and glucose intolerance but not overt hyperglycemia. Introduction of the A$^y$ mutation induces obesity and hyperglycemia. The A$^y$ mutation is a 170 kb deletion of the Raly gene that is located 5' to the agouti locus and places the control for agouti under the Raly promoter. Homozygote animals die before implantation.

Test Materials—*Acacia nilotica* sample #5659 as described in Example 13 and hops derivatives Rho-isoalpha acids, isoalpha acids and xanthohumols as described in Example 19 were used. The *Acacia nilotica*, RIAA and IAA were administered at 100 mg/kg/day, while XN was dosed at 20 mg/kg. Additionally, 5:1 and 10:1 combinations of *Acacia nilotica* with RIAA, IAA and XN were formulated and dosed at 100 mg/kg/day.

Testing Procedure—Test substances were administered daily by gavage in 0.2% Tween-80 to five animals per group. Serum was collected from the retroorbital sinus before the initial dose and ninety minutes after the third and final dose. Non-fasting serum glucose was determined enzymatically by the mutarotase/glucose oxidase method and serum insulin was determined by a mouse specific ELISA (enzyme linked immunosorbent assay).

Data Analysis—To assess whether the test substances decreased either serum glucose or insulin relative to the controls, the post-dosing glucose and insulin values were first normalized relative to pre-dosing concentrations as percent pretreatment for each mouse. The critical value (one-tail, lower 95% confidence interval for the control mice) for percent pretreatment was computed for both the glucose and insulin variables. Each percent pretreatment value for the test materials was compared with the critical value of the control. Those percent pretreatment values for the test materials that were less than the critical value for the control were considered significantly different ($p<0.05$) from the control.

Results—During the three-day treatment period, non-fasting, serum glucose rose 2.6% while serum insulin decreased 6.7% in control mice. Rosigltiazone, *Acacia nilotica*, XN:*Acacia* [1:5], XN:*Acacia* [1:10], *Acacia*:RIAA [5:1], xanthohumols, *Acacia*:IAA [5:1], isomerized alpha acids and Rho-isoalpha acids all decreased non-fasting serum glucose relative to the controls with no effect on serum insulin. *Acacia*:RIAA [10:1] and *Acacia*:IAA [10:1] had no effect on either serum glucose or insulin (Table 31).

The rapid hypoglycemic effect of *Acacia nilotica* sample #5659, xanthohumols, isomerized alpha acids, Rho-isoalpha acids and their various combinations in the KK-Ay mouse model of type 2 diabetes supports their potential for clinical efficacy in the treatment of human diseases associated with hyperglycemia.

TABLE 31

Effect of *Acacia nilotica* and hops derivatives on non-fasting serum glucose and insulin in KK-Ay diabetic mice.

| Test Material | Dosing† [mg/kg-day] | Glucose [% Pretreatment] | Insulin [% Pretreatment] |
|---|---|---|---|
| Control (Critical Value) | — | 102.6 (98.7) | 93.3 (85.4) |
| Rosiglitazone | 1.0 | 80.3# | 88.7 |
| *Acacia nilotica* sample #5659 | 100 | 89.1# | 95.3 |
| XN:*Acacia* [1:5] | 100 | 91.5# | 106.5 |
| XN:*Acacia* [1:10] | 100 | 91.7# | 104.4 |
| *Acacia*:RIAA [5:1] | 100 | 92.6# | 104.8 |
| Xanthohumols | 20 | 93.8# | 106.4 |
| *Acacia*:IAA [5:1] | 100 | 98.0# | 93.2 |
| Isomerized alpha acids | 100 | 98.1# | 99.1 |
| Rho-isoalpha acids | 100 | 98.3# | 100 |
| *Acacia*:RIAA [10:1] | 100 | 101.6 | 109.3 |
| *Acacia*:IAA [10:1] | 100 | 104.3 | 106.4 |

†Dosing was performed once daily for three consecutive days on five animals per group.
Significantly less than control ($p < 0.05$).

Example 37

In Vivo Synergy of *Acacia nilotica* and Hops Derivatives in the Diabetic db/db Mouse Model The Model—Male, C57BLKS/J $m^+/m^+Lepr^{db}$ (db/db) mice were used to assess the potential of the test materials to reduce fasting serum glucose or insulin concentrations. This strain of mice is resistant to leptin by virtue of the absence of a functioning leptin receptor. Elevations of plasma insulin begin at 10 to 14 days and of blood sugar at 4 to 8 weeks. At the time of testing (9 weeks) the animals were markedly obese 50±5 g and exhibited evidence of islet hypertrophy.

Test Materials—The positive controls metformin and rosiglitazone were dosed, respectively, at 300 mg/kg-day and 1.0 mg/kg-day for each of three consecutive days. *Acacia nilotica* sample #5659, hops derivatives and their combinations were dosed as described in Example 36.

Testing Procedure—Test substances were administered daily by gavage in 0.2% Tween-80. Serum was collected from the retroorbital sinus before the initial dose and ninety minutes after the third and final dose. Non-fasting serum glucose was determined enzymatically by the mutarotase/glucose oxidase method and serum insulin was determined by a mouse specific ELISA.

Results—The positive controls metformin and rosiglitazone decreased both serum glucose and insulin concentrations relative to the controls (Table 32). Only RIAA and XN demonstrated acceptable results as single test materials. RIAA reduced serum insulin, while XN produced a reduction in serum glucose with no effect on insulin. *Acacia*:RIAA [5:1] was the most effective agent tested for reducing serum insulin concentrations, providing a 21 percent reduction in serum insulin levels versus a 17 percent reduction in insulin concentrations by the biguanide metformin and a 15 percent decrease by the thiazolidinedione rosiglitazone. The response of this *Acacia*:RIAA [5:1] combination was greater than the responses of either individual component thus exhibiting a potential for synergy. *Acacia nilotica* alone failed to reduce either serum glucose or insulin, while RIAA reduced serum insulin to a similar extent as metformin. Of the remaining test materials, the *Acacia*:IAA [10:1] combination was also effective in reducing serum insulin concentrations.

The rapid reduction of serum insulin affected by Rho-isoalpha acids and reduction of serum glucose by xanthohumols in the db/db mouse model of type 2 diabetes supports their potential for clinical efficacy in the treatment of human diseases associated with insulin insensitivity and hyperglycemia. Further, the 5:1 combination of Rho-isoalpha acids and *Acacia catechu* appeared synergistic in the db/db murine diabetes model. The positive responses exhibited by Rho-isoalpha acids, xanthohumols and the *Acacia*:RIAA [5:1] formulation in two independent animal models of diabetes and three in vitro models supports their potential usefulness in clinical situations requiring a reduction in serum glucose or enhance insulin sensitivity.

TABLE 32

Effect of *Acacia nilotica* and hops derivatives on non-fasting serum glucose and insulin in db/db diabetic mice.

| Test Material | Dosing† [mg/kg-day] | Glucose [% Pretreatment] | Insulin [% Pretreatment] |
|---|---|---|---|
| Control (Critical Value) | — | 103.6 (98.4) | 94.3 (84.9) |
| *Acacia*:RIAA [5:1] | 100 | 99.6 | 79.3# |
| Metformin | 300 | 67.6# | 83.3# |

TABLE 32-continued

Effect of *Acacia nilotica* and hops derivatives on non-fasting serum glucose and insulin in db/db diabetic mice.

| Test Material | Dosing† [mg/kg-day] | Glucose [% Pretreatment] | Insulin [% Pretreatment] |
|---|---|---|---|
| Rho-isoalpha acids | 100 | 102.3 | 83.8# |
| *Acacia*:IAA [10:1] | 100 | 104.3 | 84.4# |
| Rosiglitazone | 1.0 | 83.0# | 84.7# |
| XN:*Acacia* [1:10] | 100 | 101.5 | 91.1 |
| *Acacia nilotica* sample#5659 | 100 | 100.4 | 91.9 |
| *Acacia*:RIAA [10:1] | 100 | 101.6 | 93.5 |
| Isomerized alpha acids | 100 | 100.8 | 95.8 |
| Xanthohumols | 20 | 97.8# | 101.6 |
| XN:*Acacia* [1:5] | 100 | 104.1 | 105.6 |
| *Acacia*:IAA [5:1] | 100 | 102.7 | 109.1 |

†Dosing was performed once daily for three consecutive days on five animals per group.
Significantly less than respective control ($p < 0.05$).

The invention now having been fully described, it will be apparent to one of ordinary skill in the art that many changes and modifications can be made thereto without departing from the spirit or scope of the appended claims.

The invention claimed is:

1. An oral composition for treating an insulin related disorder in a subject in need thereof, said composition consisting essentially of a therapeutically effective amount of a compound selected from the group consisting of tetrahydro-isohumulone, tetrahydro-isocohumulone, and tetrahydro-isoadhumulone; and metformin, wherein the composition is in a dosage form for oral administration.

2. An oral composition for treating diabetes in a subject in need thereof, said composition consisting essentially of a therapeutically effective amount of a compound selected from the group consisting of tetrahydro-isohumulone, tetrahydro-isocohumulone, and tetrahydro-isoadhumulone; and metformin, wherein the composition is in a dosage form for oral administration.

3. An oral composition for treating obesity in a subject in need thereof, said composition consisting essentially of a therapeutically effective amount of a compound selected from the group consisting of tetrahydro-isohumulone, tetrahydro-isocohumulone, and tetrahydro-isoadhumulone; and metformin, wherein the composition is in a dosage form for oral administration.

4. An oral composition for treating a cardiovascular disease in a subject in need thereof, said composition consisting essentially of a therapeutically effective amount of a compound selected from the group consisting of tetrahydro-isohumulone, tetrahydro-isocohumulone, and tetrahydro-isoadhumulone; and metformin, wherein the composition is in a dosage form for oral administration.

* * * * *